US007220780B2

(12) United States Patent
Slusher et al.

(10) Patent No.: US 7,220,780 B2
(45) Date of Patent: May 22, 2007

(54) NAALADASE INHIBITORS FOR TREATING RETINAL DISORDERS AND GLAUCOMA

(75) Inventors: Barbara S. Slusher, Kingsville, MD (US); Krystyna Wozniak, Bel Air, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 1087 days.

(21) Appl. No.: 09/866,961

(22) Filed: May 30, 2001

(65) Prior Publication Data

US 2003/0036534 A1 Feb. 20, 2003

Related U.S. Application Data

(60) Provisional application No. 60/207,320, filed on May 30, 2000.

(51) Int. Cl.
*A61K 31/19* (2006.01)
(52) U.S. Cl. .................. 514/568; 514/557; 514/912; 514/913
(58) Field of Classification Search ................ 514/557, 514/568, 912, 913
See application file for complete search history.

(56) References Cited

U.S. PATENT DOCUMENTS

| 5,672,592 | A |   | 9/1997  | Jackson et al. |         |
|-----------|---|---|---------|----------------|---------|
| 5,795,877 | A |   | 8/1998  | Jackson et al. |         |
| 5,804,602 | A |   | 9/1998  | Slusher et al. |         |
| 5,824,662 | A |   | 10/1998 | Slusher et al. |         |
| 5,863,536 | A |   | 1/1999  | Jackson et al. |         |
| 5,880,112 | A |   | 3/1999  | Jackson et al. |         |
| 5,902,817 | A |   | 5/1999  | Jackson et al. |         |
| 5,962,521 | A |   | 10/1999 | Jackson et al. |         |
| 5,968,915 | A |   | 10/1999 | Jackson et al. |         |
| 5,977,090 | A |   | 11/1999 | Slusher et al. |         |
| 5,981,209 | A |   | 11/1999 | Slusher et al. |         |
| 5,985,855 | A |   | 11/1999 | Slusher et al. |         |
| 6,004,946 | A |   | 12/1999 | Slusher et al. |         |
| 6,011,021 | A |   | 1/2000  | Slusher et al. |         |
| 6,017,903 | A |   | 1/2000  | Slusher et al. |         |
| 6,025,344 | A |   | 2/2000  | Jackson et al. |         |
| 6,025,345 | A |   | 2/2000  | Jackson et al. |         |
| 6,028,216 | A |   | 2/2000  | Morales et al. |         |
| 6,046,180 | A |   | 4/2000  | Jackson et al. |         |
| 6,054,444 | A |   | 4/2000  | Jackson et al. |         |
| 6,071,965 | A |   | 6/2000  | Jackson et al. |         |
| 6,121,252 | A |   | 9/2000  | Jackson et al. |         |
| 6,159,958 | A | * | 12/2000 | Meyerhoff et al. | 514/148 |
| 6,228,888 | B1|   | 5/2001  | Slusher        |         |
| 6,265,609 | B1|   | 7/2001  | Jackson et al. |         |
| 6,271,245 | B1|   | 8/2001  | Jackson et al. |         |

FOREIGN PATENT DOCUMENTS

WO   WO 99/08521   8/1998

WO   WO 99/33849   7/1999
WO   WO 00/01668   1/2000
WO   WO 01/14390   3/2001

OTHER PUBLICATIONS

Jackson et al., "Design Synthesis and Biological Activity of a Potent Inhibitor of the Neuropeptidase N-Acetylated α-Linked Acidic Dipeptidase", Journal of Medicinal Chemistry, American Chemical Society, Washington, US, vol. 39, No. 2, 1996, pp. 619-622.
Ueda et al., Jun, "Experimental Glaucoma Model in the Rat Induced by Laser Travecular Photocoagulation After an Intracameral Injection of India Ink", Japan Journal Ophthalmology, vol. 42, 1998, pp. 337-344.
Neufeld et al., A.H., "Inhibition of nitric-oxide synthase 2 by aminoguanidine provides neuroprotection of retinal ganglion cells in a rat model of chronic glaucoma", Proc. Natl. Acad. Sci., vol. 96, Aug. 1999, pp. 9944-9948.
Morrison et al., J.C., "A Rat Model of Chronic Pressure-induced Optic Nerve Damage", Exp. Eye Res., vol. 64, No. 1, Jan. 1997, pp. 85-96.
Morrison et al., J.C., "Glaucoma Drops Control Intraocular Pressure and Protect Optic Nerves in a Rat Model of Glaucoma", Investigative Ophthalmology & Visual Science, vol. 39, No. 3, Mar. 1998, pp. 526-531.
Laver et al., N.M., "Novel Procedures for Isolating Intact Retinal Vascular Beds From Diabetic Humans and Animal Models", Investigative Ophthalmology & Visual Science, vol. 34, No. 6, May 1993, pp. 2097-2104.
Gundersen et al., H.J.G., "Optimizing sampling efficiency of stereological studies in biology: or 'Do more less well!'", Journal of Microscopy, vol. 121, Pt. 1, Jan. 1981, pp. 65-73.
Harada et al., C., "N-acetylated-α-linked-acidic dipeptidase inhibitor has a neuroprotective effect on mouse retinal ganglion cells after pressure-induced ischemia", Neuroscience Letters, vol. 286, 2000, pp. 1-3.
Quigley et al., D.J., "Naaladase Inhibitors Prevent Retinal Ganglion Cell Death In Experimental Glaucoma and After Optic Nerve Transection In The Rat", Glaucoma Service, Wilmer Institute, Johns Hopkins School of Medicine.
Kuwabara et al., T., "Studies of Retinal Vascular Patterns", Achives of Ophthalmology, vol. 64, No. 6, Dec. 1960, pp. 904-911.
Collman et al., J.P., "Dioxygen Binding in Iron and Cobalt Picnic Basket Porphyrins", J. Am. Chem. Soc., vol. 116, No. 14, 1994, pp. 6245-6251.
Cuthbertson et al., R.A., "Anatomy of the Mouse Retina. Endothelial Cell-Pericyte Ratio and Capillary Distribution", Investigative Ophthalmology & Visual Science, vol. 27, No. 11, Nov. 1986, pp. 1659-1664.
Bendayan, M., "Protein A-Gold Electron Microscopic Immunocytochemistry: Methods, Applications, and Limitations", Journal of Electron Microscopy Technique, vol. 1, 1984, pp. 243-270.

* cited by examiner

*Primary Examiner*—Zohreh Fay
(74) *Attorney, Agent, or Firm*—Arnold & Porter LLP

(57) ABSTRACT

The present invention relates to pharmaceutical compositions and methods for treating a retinal disorder or glaucoma using NAALADase inhibitors.

10 Claims, 3 Drawing Sheets

NAALADASE INHIBITORS FOR TREATING RETINAL DISORDERS AND GLAUCOMA

This application claims the benefit of U.S. Provisional Application No. 60/207,320 filed on May 30, 2000.

The present invention relates to pharmaceutical compositions and methods for treating glaucoma and retinal disorders using NAALADase inhibitors.

Glutamate has been implicated in the pathophysiology of various retinal disorders. For example, elevated vitreous glutamate levels have been detected in patients with proliferative diabetic retinopathy. Additionally, retinal detachment has been shown to induce rapid glutamatergic alterations in the neural retina. Abnormal formation and degradation of glutamate have also been observed in the retina during retinitis pigmentosa.

One source of glutamate is derived from the neuropeptide N-acetylated-aspartyl-glutamate (NAAG) through cleavage by N-acetylated-α-linked acidic dipeptidase (NAALADase), also known as prostate specific membrane antigen (PSM or PSMA) and human glutamate carboxypeptidase II (GCP II). Studies suggest that NAALADase inhibitors may block glutamate release pre-synaptically without interacting with post-synaptic glutamate receptors.

Glaucoma is a group of eye diseases characterized by optic disk excavation, retinal ganglion cell (RGC) loss and visual field loss. Since elevated intraocular pressure (IOP) is a major risk factor for glaucoma, pharmacological and surgical treatments of glaucoma have been aimed at lowering IOP. The drugs currently used in treating glaucoma include miotics (e.g., pilocarpine, carbachol, and acetylcholinesterase inhibitors), sympathomimetics (e.g., epinephrine and dipivalylepinephrine), beta-blockers (e.g., timolol, betaxolol, carteolol, levobunolol and metipranolol), alpha-2 agonists (e.g., para-amino clonidine) and carbonic anhydrase inhibitors (e.g., acetazolamide, methazolamide and ethoxzolamide). Miotics and sympathomimetics are believed to lower IOP by increasing the outflow of aqueous humor, while beta-blockers, alpha-2 agonists and carbonic anhydrase inhibitors are believed to lower IOP by decreasing the formation of aqueous humor. All five types of drugs have potential side effects. Miotics, such as pilocarpine, can cause blurring of vision and other visual side effects. Sympathomimetics have a fairly high incidence of allergic or toxic reactions. Carbonic anhydrase inhibitors can cause serious side effects that may decrease patient compliance and/or require termination of drug therapy. At least one beta-blocker, timolol, has become associated with serious pulmonary side effects attributable to its effect on beta-2 receptors in pulmonary tissue. Notwithstanding the side effects, some cases of glaucoma continue to worsen despite IOP lowering. Thus, a need exists for new glaucoma treatments.

SUMMARY OF THE INVENTION

The present inventors have surprisingly discovered that NAALADase inhibitors may be effective in slowing, if not preventing, retinal ganglion cell death associated with glaucoma. Thus, the present invention relates to a method for treating glaucoma comprising administering an effective amount of a NAALADase inhibitor to an animal or a mammal in need of such treatment.

The present invention further relates to a method for treating retinopathy, age-related macular degeneration or glaucoma comprising administering an effective amount of a NAALADase inhibitor to a mammal in need of such treatment.

The present invention also relates to a pharmaceutical composition comprising:
  (i) an effective amount of a NAALADase inhibitor for treating retinopathy, age-related macular degeneration or glaucoma; and
  (ii) a pharmaceutically acceptable carrier.

DETAILED DESCRIPTION OF THE INVENTION

Definitions

Figure 1:
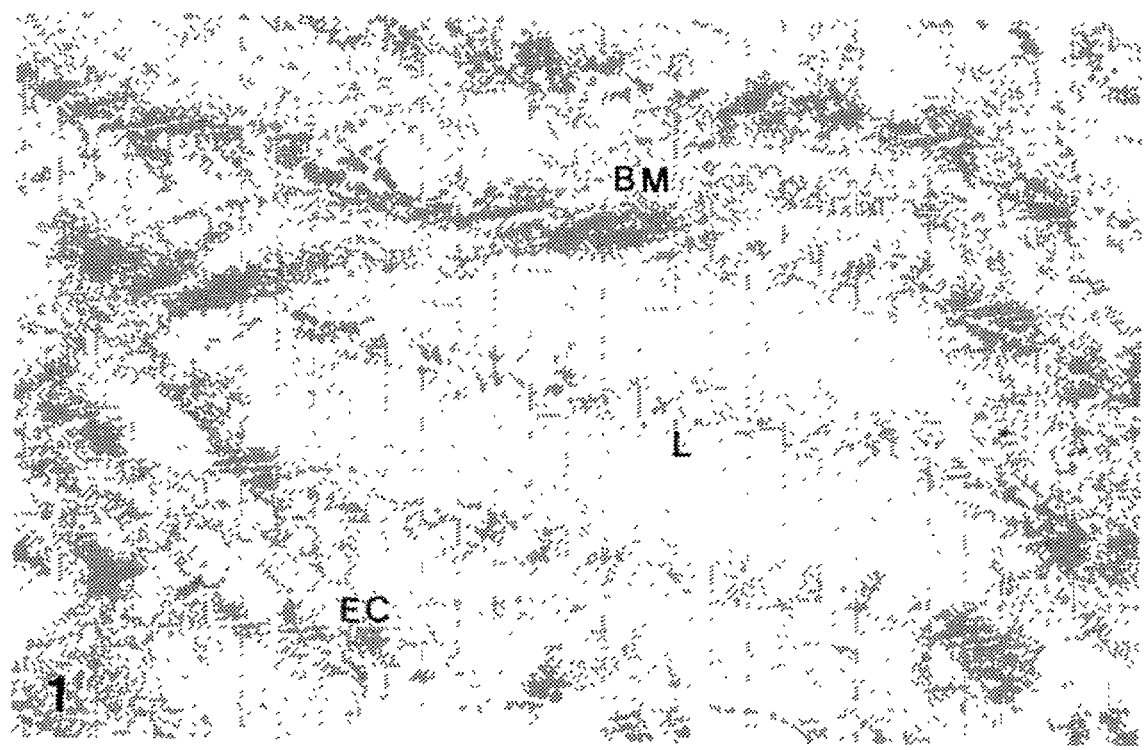
FIG. 1 is a 27,000× magnified photograph of a retinal blood vessel from a control, non-diabetic rat.

"Alkyl" refers to a branched or unbranched saturated hydrocarbon chain comprising a designated number of carbon atoms. For example, $C_1$-$C_9$ alkyl is a straight or branched hydrocarbon chain containing 1 to 9 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$-$C_9$ alkenyl is a straight or branched hydrocarbon chain containing 2 to 9 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 9 carbon atoms.

"Carbocycle" refers to a hydrocarbon, cyclic moiety having one or more closed ring(s) that is/are alicyclic, aromatic, fused and/or bridged. Examples include cyclopropane, cyclobutane, cyclopentane, cyclohexane, cycloheptane, cyclopentene, cyclohexene, cycloheptene, cycloctene, benzyl, naphthene, anthracene, phenanthracene, biphenyl and pyrene.

"Aryl" refers to an aromatic, hydrocarbon cyclic moiety having one or more closed ring(s). Examples include, without limitation, phenyl, naphthyl, anthracenyl, phenanthracenyl, biphenyl and pyrenyl.

"Heterocycle" refers to a cyclic moiety having one or more closed ring(s) that is/are alicyclic, aromatic, fused and/or bridged, with one or more heteroatom(s) (for example, sulfur, nitrogen or oxygen) in at least one of the rings. Examples include, without limitation, pyrrolidine, pyrrole, thiazole, thiophene, piperidine, pyridine, isoxazolidine and isoxazole.

"Heteroaryl" refers to an aromatic, cyclic moiety having one or more closed ring(s) with one or more heteroatom(s) (for example, sulfur, nitrogen or oxygen) in at least one of the rings. Examples include, without limitation, pyrrole, thiophene, pyridine and isoxazole.

"Linking group" refers to a moiety that connects the terminal group with the benzene ring in the compounds of formula VI, without compromising with the pharmacological or biological activity of the overall compound.

"Metal binding group" refers to a functional group capable of interacting with metal ion(s), such as $Co^{2+}$, $Ni^{2+}$, $Mn^{2+}$, $Cu^{2+}$, $Zn^{2+}$, $Mg^{2+}$, $Fe^{2+}$, $Fe^{3+}$, or $Al^{3+}$. Common metal binding groups include amines (e.g. ethylenediamine), aldehydes, ketones, carboxylic acids (e.g. ethylenediaminetetraacetic acid (EDTA)), thiols, phosphorus derivatives and hydroxamic acids.

"Derivative" refers to a substance produced from another substance either directly or by modification or partial substitution.

"Effective amount" refers to the amount required to produce the desired effect.

"Therapeutically effective amount" refers to the amount required to treat glaucoma in an animal or a mammal.

"Halo" refers to at least one fluoro, chloro, bromo or iodo moiety.

"Isosteres" refer to elements, functional groups, substitutents, molecules or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Ideally, isosteric compounds should be isomorphic and able to co-crystallize. Other physical properties that isosteric compounds usually share include boiling point, density, viscosity and thermal conductivity. However, certain properties are usually different: dipolar moments, polarity, polarization, size and shape since the external orbitals may be hybridized differently. The term "isosteres" encompass "bioisosteres".

"Bioisosteres" are isosteres that, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acyl-cyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus-derived acidic functions such as phosphinates, phosphonates, phosphonamides, sulphonates, sulphonamides, and acylsulphonamides.

"Metabolite" refers to an intermediate or product resulting from metabolism.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically mGluR3 receptors; when attached to a moiety capable of inhibiting NAALADase, it is expected that metabotropic glutamate receptor ligands will provide potent and specific NAALADase inhibitors.

"NAALADase" refers to N-acetylated α-linked acidic dipeptidase, a membrane bound metallopeptidase that catabolizes NAAG to N-acetylaspartate ("NAA") and glutamate ("GLU"):

Catabolism of NAAG by NAALADase

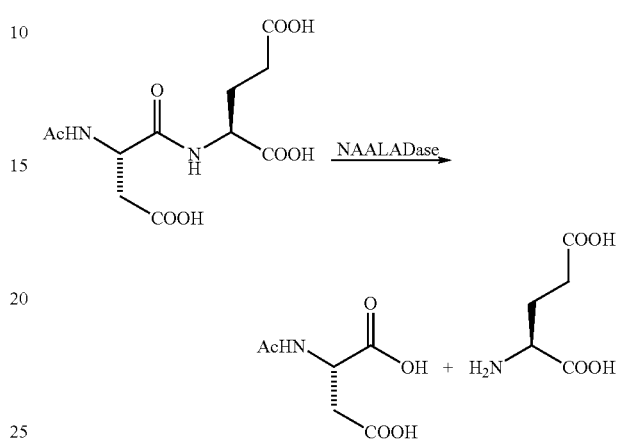

NAALADase has been assigned to the M28 peptidase family and is also called prostate specific membrane antigen (PSM) or human glutamate carboxypeptidase II (GCP II), EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably nontoxic, that would be suitable for use in a pharmaceutical composition.

"Pharmaceutically acceptable equivalent" includes, without limitation, pharmaceutically acceptable salts, hydrates, metabolites, prodrugs, and isosteres. Many pharmaceutically acceptable equivalents are expected to have the same or similar in vitro or in vivo activity as the inventive compounds.

"Pharmaceutically acceptable salt" refers to a salt of the inventive compounds that possesses the desired pharmacological activity and that is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quaternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172-178, 949-982 (1995).

"Inhibition," in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound that is required to cause a 50% inhibition of the target enzyme.

"NAALADase inhibitor" refers to any compound that inhibits NAALADase enzyme activity. Preferably, a NAALADase inhibitor exhibits a $K_i$ of less than 100 μM, more preferably less than 10 μM, and even more preferably less than 1 μM, as determined using any appropriate assay known in the art.

"Isomers" refer to compounds having the same number and kind of atoms, and hence the same molecular weight, but differing in respect to the arrangement or configuration of the atoms.

"Optical isomers" refer to enantiomers or diastereoisomers.

"Stereoisomers" are isomers that differ only in the arrangement of the atoms in space.

"Diastereoisomers" are stereoisomers that are not mirror images of each other. Diastereoisomers occur in compounds having two or more asymmetric carbon atoms; thus, such compounds have $2^n$ optical isomers, where n is the number of asymmetric carbon atoms "Enantiomers" are a pair of stereoisomers that are non-superimposable mirror images of each other. Enantiomers result, for example, from the presence of one or more asymmetric carbon atom(s) in the compound (e.g., glyceraldehyde, lactic acid, sugars, tartaric acid, amino acids).

"Enantiomer-enriched" refers to a mixture in which one enantiomer predominates.

"Racemic mixture" means a mixture containing equal amounts of enantiomers.

"Non-racemic mixture" is a mixture containing unequal amounts of enantiomers.

"Animal" refers to a living organism having sensation and the power of voluntary movement, and which requires for its existence oxygen and organic food. Examples include, without limitation, members of the human, equine, porcine, bovine, murine, canine, or feline species. In the case of a human, an "animal" may also be referred to as a "patient".

"Mammal" refers to a warm-blooded vertebrate animal.

"Glaucoma" includes without limitation chronic (idiopathic) open-angle glaucomas (e.g., high-pressure, normal-pressure); pupillary block glaucomas (e.g., acute angle-closure, subacute angle-closure, chronic angle-closure, combined-mechanism); developmental glaucomas (e.g., congenital (infantile), juvenile, Anxenfeld-Rieger syndrome, Peters' anomaly, Aniridia); glaucomas associated with other ocular disorders (e.g., glaucomas associated with disorders of the corneal endothelium, iris, ciliary body, lens, retina, choroid and vitreous); glaucomas associated with elevated episcleral venous pressure (e.g., systemic diseases with associated elevated intraocular pressure and glaucoma, corticosteroid-induced glaucoma); glaucomas associated with inflammation and trauma (e.g., glaucomas associated with keratitis, episcleritis, scleritis, uveitis, ocular trauma and hemorrhage); glaucomas following intraocular surgery (e.g., ciliary block (malignant) glaucoma, glaucomas in aphakia and pseudophakia, glaucomas associated with corneal surgery, glaucomas associated with vitreoretinal surgery).

"Treating" refers to:

(i) preventing a disease, disorder or condition from occurring in an animal that may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

"Treating a retinal disorder" refers to:

(i) preventing a retinal disorder from occurring in an animal that may be predisposed to a retinal disorder but has not yet been diagnosed as having it;

(ii) inhibiting or slowing a retinal disorder, e.g. arresting its development; and/or (iii) relieving a retinal disorder, e.g. causing its regression.

"Retinal disorder" refers to vascular retinopathy, for example, hypertensive retinopathy, diabetic retinopathy (nonproliferative or proliferative), central retinal artery occlusion, or central retinal vein occlusion; age-related macular degeneration; retinal detachment; or retinitis pigmentosa.

One of ordinary skill in the art would recognize that there are alternative nomenclatures, nosologies and classification systems for the diseases, disorders and conditions defined above, and that such systems evolve with medical scientific progress.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Methods of the Present Invention

The present invention relates to a method for treating a retinal disorder comprising administering an effective amount of a NAALADase inhibitor to an animal or a mammal in need of such treatment.

The present invention further relates to a method for treating glaucoma comprising administering an effective amount of a NAALADase inhibitor to an animal or a mammal in need of such treatment.

Pharmaceutical Compositions of the Present Invention

The present invention further relates to a pharmaceutical composition comprising:
 (i) an effective amount of a NAALADase inhibitor for treating a retinal disorder or glaucoma; and
 (ii) a pharmaceutically acceptable carrier.

NAALADase Inhibitors

NAALADase inhibitors that can be used in the inventive methods and pharmaceutical compositions include without limitation metallopeptidase inhibitors such as o-phenanthroline, metal chelators such as EGTA and EDTA, and peptide analogs such as quisqualic acid and β-NAAG.

While the pathophysiology of retinal disorders or neuronal death in glaucoma is not well understood, there is evidence that it may involve glutamate excitotoxicity. Thus, a preferred NAALADase inhibitor is one that is capable of reducing or preventing glutamate-induced excitotoxicity, thereby reducing or preventing neuronal or retinal ganglion cell (RGC) damage or death resulting from such excitotoxicity. A particularly preferred NAALADase inhibitor for treating a retinal disorder is one that is capable of reducing or preventing RGC damage or death through a mechanism that does not modulate aqueous humor dynamics or intraocular pressure (IOP). While the foregoing attributes are preferred, the NAALADase inhibitors used in the inventive methods and pharmaceutical compositions may exert their therapeutic effects through other mechanisms of action.

Another preferred NAALADase inhibitor is an acid containing a metal binding group.

Formula I

Another preferred NAALADase inhibitor is a compound of formula I:

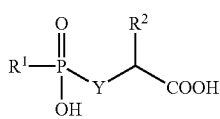

or an enantiomer or a pharmaceutically acceptable equivalent of said compound, wherein:

Y is $CR^3R^4$, $NR^5$ or O;

$R^1$ is hydrogen, $C_1$-$C_9$ alkyl, $C_2$-$C_9$ alkenyl, $C_3$-$C_8$ cycloalkyl, $C_5$-$C_7$ cycloalkenyl, Ar, $COOR^6$, $NR^6R^7$ or $OR^6$, wherein said alkyl, alkenyl, cycloalkyl and cycloalkenyl are independently unsubstituted or substituted with one or more substituent(s), preferably, independently selected from the group consisting of carboxy, $C_3$-$C_8$ cycloalkyl, $C_5$-$C_7$ cycloalkenyl, halo, hydroxy, nitro, trifluoromethyl, $C_1$-$C_6$ alkyl, $C_2$-$C_6$ alkenyl, $C_1$-$C_9$ alkoxy, $C_2$-$C_9$ alkenyloxy, phenoxy, benzyloxy, $COOR^6$, $NR^6R^7$ and Ar;

$R^2$ is hydrogen, $C_1$-$C_6$ alkyl, $C_2$-$C_6$ alkenyl, $C_3$-$C_8$ cycloalkyl, $C_5$-$C_7$ cycloalkenyl, Ar, halo or carboxy, wherein said alkyl, alkenyl, cycloalkyl and cycloalkenyl are independently unsubstituted or substituted with one or more substituent(s), preferably, independently selected from the group consisting of carboxy, $C_3$-$C_8$ cycloalkyl, $C_5$-$C_7$ cycloalkenyl, halo, hydroxy, nitro, trifluoromethyl, $C_1$-$C_6$ alkyl, $C_2$-$C_6$ alkenyl, $C_1$-$C_9$ alkoxy, $C_2$-$C_9$ alkenyloxy, phenoxy, benzyloxy, $NR^6R^7$ and Ar;

$R^3$ and $R^4$ are independently hydrogen or $C_1$-$C_3$ alkyl;

$R^5$ is hydrogen or $C_1$-$C_3$ alkyl;

$R^6$ and $R^7$ are independently hydrogen, $C_1$-$C_9$ alkyl, $C_2$-$C_9$ alkenyl, $C_3$-$C_8$ cycloalkyl, $C_5$-$C_7$ cycloalkenyl or Ar, wherein said alkyl, alkenyl, cycloalkyl and cycloalkenyl are independently unsubstituted or substituted with one or more substituent(s), preferably, independently selected from the group consisting of carboxy, $C_3$-$C_8$ cycloalkyl, $C_5$-$C_7$ cycloalkenyl, halo, hydroxy, nitro, trifluoromethyl, $C_1$-$C_6$ alkyl, $C_2$-$C_6$ alkenyl, $C_2$-$C_9$ alkoxy, $C_2$-$C_9$ alkenyloxy, phenoxy, benzyloxy and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent(s), preferably, independently selected from the group consisting of halo, hydroxy, nitro, trifluoromethyl, $C_1$-$C_6$ alkyl, $C_2$-$C_6$ alkenyl, $C_1$-$C_6$ alkoxy, $C_2$-$C_6$ alkenyloxy, phenoxy, benzyloxy, carboxy and $N^6R^7$.

In one embodiment of formula I, Y is $CH_2$.

In another embodiment, $R^2$ is —$(CH_2)_2COOH$.

In a further embodiment, $R^1$ is hydrogen, $C_1$-$C_4$ alkyl, $C_2$-$C_4$ alkenyl, $C_3$-$C_8$ cycloalkyl, $C_5$-$C_7$ cycloalkenyl, benzyl, phenyl or $OR^6$, wherein said alkyl, alkenyl, cycloalkyl, cycloalkenyl, benzyl and phenyl are independently unsubstituted or substituted with one or more substituent(s) independently selected from the group consisting of carboxy, $C_3$-$C_8$ cycloalkyl, $C_5$-$C_7$ cycloalkenyl, halo, hydroxy, nitro, trifluoromethyl, $C_1$-$C_6$ alkyl, $C_2$-$C_6$ alkenyl, $C_1$-$C_6$ alkoxy, $C_2$-$C_6$ alkenyloxy, phenoxy, benzyloxy, $NR^6R^7$, benzyl and phenyl.

Preferred compounds of formula I are selected from the group consisting of:
 2-(phosphonomethyl)pentanedioic acid;
 2-[[(2-carboxyethyl)hydroxyphosphinyl]methyl]-pentanedioic acid;
 2-[(benzylhydroxyphosphinyl)methyl]pentanedioic acid;
 2-[(phenylhydroxyphosphinyl)methyl]pentanedioic acid;
 2-[[((hydroxy)phenylmethyl)hydroxyphosphinyl]-methyl]pentanedioic acid;
 2-[(butylhydroxyphosphinyl)methyl]pentanedioic acid;
 2-[[(3-methylbenzyl)hydroxyphosphinyl]methyl]-pentanedioic acid;
 2-[(3-phenylpropylhydroxyphosphinyl)methyl]-pentanedioic acid;
 2-[[(4-fluorophenyl)hydroxyphosphinyl]methyl]-pentanedioic acid;
 2-[(methylhydroxyphosphinyl)methyl]pentanedioic acid;
 2-[(phenylethylhydroxyphosphinyl)methyl]pentanedioic acid;

2-[[(4-methylbenzyl)hydroxyphosphinyl]methyl]-pentanedioic acid;
2-[[(4-fluorobenzyl)hydroxyphosphinyl]methyl]-pentanedioic acid;
2-[[(4-methoxybenzyl)hydroxyphosphinyl]methyl]-pentanedioic acid;
2-[[(3-trifluoromethylbenzyl)hydroxyphosphinyl]-methyl]pentanedioic acid;
2-[[4-trifluoromethylbenzyl)hydroxyphosphinyl]-methyl]pentanedioic acid;
2-[[(2-fluorobenzyl)hydroxyphosphinyl]methyl]-pentanedioic acid;
2-[[(2,3,4,5,6-pentafluorobenzyl)hydroxy-phosphinyl]methyl]pentanedioic acid; and
enantiomers and pharmaceutically acceptable equivalents.

Formula II

Another preferred NAALADase inhibitor is a compound of formula II

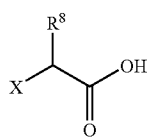

or an enantiomer or a pharmaceutically acceptable equivalent of said compound, wherein:
X is a moiety of formula III, IV or V

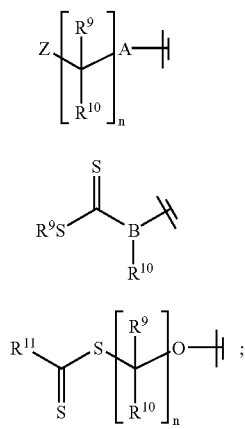

Z is SH, SO$_{3H}$, SO$_2$H, SOH, SO(NH)R$^{12}$ or S(NHR$^{12}$)$_2$R$^{13}$;
B is N or CR$^{14}$;
A is O, S, CR$^{15}$R$^{16}$ or (CR$^{15}$R$^{16}$)$_m$S;
m and n are independently 0, 1, 2, 3 or 4;
R$^8$, R$^9$, R$^{10}$, R$^{11}$, R$^{12}$, R$^{14}$, R$^{15}$ and R$^{16}$ are independently hydrogen, C$_1$-C$_9$ alkyl, C$_2$-C$_9$ alkenyl, C$_3$-C$_8$ cycloalkyl, C$_5$-C$_7$ cycloalkenyl, Ar$^1$, hydroxy, carboxy, carbonyl, amino, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent (s); and Ar$^1$ is a carbocyclic or heterocyclic moiety, which is unsubstituted or substituted with one or more substituent(s);
provided that when X is a moiety of formula III and A is O, then n is 2, 3 or 4; when X is a moiety of formula III and A is S, then n is 2, 3 or 4; and when X is a moiety of formula III and A is (CR$^{15}$R$^{16}$)$_m$S, then n is 0, 2, 3 or 4.

In one embodiment of formula II, X is a moiety of formula III; n is 0, 1, 2 or 3; Z is SH, SO$_3$H, SO$_2$H, SOH or S(NHR$^{12}$)$_2$R$^{13}$; and A is O, S or CR$^{15}$R$^{16}$.

In another embodiment, R$^8$ is —(CH$_2$)$_2$COOH.
In a further embodiment, Z is SH.
Preferred compounds of formula II are selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
enantiomers and pharmaceutically acceptable equivalents.

Formula VI

Another preferred NAALADase inhibitor is a compound of formula VI

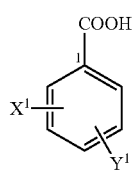

or an enantiomer or a pharmaceutically acceptable equivalent of said compound, wherein:
X$^1$ is —W—Z$^1$;
W is a bond or a linking group;
Z$^1$ is a terminal group; and
Y$^1$ is —COOH oriented meta or para relative to C-1.

Linking groups include, without limitation, divalent hydrocarbon chains, ethers, sulfides and amines, wherein the hydrocarbon chain, whether alone or part of the ether, sulfide or amine, may be saturated or unsaturated, straight or branched, open or closed, unsubstituted or substituted with one or more substituent(s), preferably, independently selected from the group consisting of C$_1$-C$_6$ alkoxy, C$_2$-C$_6$ alkenyloxy, phenoxy, benzyloxy, hydroxy, carboxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitro, nitroso, isonitroso, nitrosamino, imino, nitrilo, isonitrilo, nitrosimino, oxo, C$_1$-C$_6$ alkylthio, sulfamino, sulfamoyl, sulfeno, sulfhydryl, sulfinyl, sulfo, sulfonyl, sulfoxy, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, diselanyl, siloxy, silyl and silylene.

Preferably, W is a bond, —$(CR^{17}R^{18})_n$—, —$(CR^{17}R^{18})_n$ $O(CR^{19}R^{20})_m$—, —$(CR^{17}R^{18})_n S(CR^{19}R^{20})_m$— or —$(CR^{17}R^{18})_n NR^{21}(CR^{19}R^{20})_m$—, wherein m and n are independently 0-9, and $R^{17}$, $R^{18}$, $R^{19}$, $R^{20}$ and $R^{21}$ are independently hydrogen, $C_1$-$C_6$ alkyl, $C_2$-$C_6$ alkenyl, $C_2$-$C_6$ alkynyl, $C_6$-$C_{14}$ aryl, heteroaryl, C6-$C_{14}$ carbocycle, heterocycle, halo, hydroxy, sulfhydryl, nitro, amino or $C_1$-$C_6$ alkoxy, and said alkyl, alkenyl, alkynyl, aryl, heteroaryl, carbocycle, heterocycle and alkoxy are independently unsubstituted or substituted with one or more substituent(s). More preferably, $R^{17}$, $R^{18}$, $R^{19}$, $R^{20}$ and $R^{21}$ are each hydrogen and the total number of carbon atoms in W is 2-6.

Preferably, $Z^1$ is a metal binding group. More preferably, $Z^1$ is —COOH, —$COR^{22}$, —$OR^{22}$, —$CF_3$, —CN, —F, —Cl, —Br, —I, —NO, —$NO_2$, —C(O) ($NR^{22}OR^{23}$), —C(O) ($NR^{22}PO_3H_2$), —C(O)($NR^{22}R^{23}$), =NOH, —$NR^{22}$ (P(O) ($R^{23}$)OH), =$NR^{22}$, —N=$NR^{22}$, —N($R^{22}$)CN, —$NR^{22}(CR^{23}R^{24})_p$COOH, —$NR^{22}$ (CO) $NR^{23}R^{24}$, —$NR^{22}$ ($COOR^{23}$) —$NR^{22}(CO)R^{23}$, —$NR^{22}(OR^{23})$, —$NR^{22}R^{23}$, —$NR^{22}(SO_2R^{23})$, —$O(CO)R^{22}$, —$OR^{22}$, —$SO_2(OR^{22})$, —$SO_2(NR^{22}R^{23})$, —$SO_2R^{22}$, —$SO_3R^{22}$, —$SNR^{22}(OR^{23})$, —$S(NR^{22}R^{23})_2$, —$SR^{22}$, —$SSR^{22}$, —P(O)(OH)$OR^{22}$, —P(O)(OH)$R^{22}$ or —$PR^{22}R^{23}$, wherein p is 0-6, and $R^{22}$, $R^{23}$ and $R^{24}$ are independently hydrogen, $C_1$-$C_9$ alkyl, $C_2$-$C_9$ alkenyl, $C_2$-$C_9$ alkynyl, $C_6$-$C_{14}$ aryl, heteroaryl, $C_6$-$C_{14}$ carbocycle, heterocycle, halo, hydroxy, sulfhydryl, nitro, amino or $C_1$-$C_9$ alkoxy, and said alkyl, alkenyl, alkynyl, aryl, heteroaryl, carbocycle, heterocycle and alkoxy are independently unsubstituted or substituted with one or more substituent (s). Even more preferably, $Z^1$ is —$NH(CR^{23}R^{24})_p$ COOH, —PO(OH)$OR^{22}$, —PO(OH)$R^{22}$, —$NR^{22}$(P(O) ($R^{23}$)OH), —CON($R^{22}$)(OH) or —SH.

In one embodiment of formula VI:

$X^1$ is —$(CR^{17}R^{18})_n$NH $(CR^{19}R^{20})_m$COOH, —PO(OH) $OR^{22}$, —$(CR^{17}R^{18})_n$P(O) (OH) $R^{22}$, —NH—$(CR^{19}R^{20})_m$— heteroaryl, —NH(P(O)($R^{23}$)OH), —$(CR^{17}R^{18})_n$NH(P(O) (OH)$R^{23}$), —CON($R^{22}$) (OH) —$(CR^{17}CR^{18})_n$CON($R^{22}$) (OH), —$(CR^{17}R^{18})_n$SH or —$O(CR^{19}R^{20})_m$SH, —$SO_2$NH—aryl, —N(C=O)—$CH_2$(C=O)—aryl, —$SO_2$NH—aryl, —N(C=O)—$CH_2$(C=O)—aryl, —O—aryl wherein aryl in —O—aryl is substituted by at least one of nitro, carboxy or

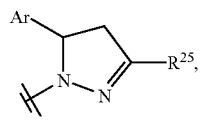

wherein $X^1$ is oriented meta or para relative to C-1;

m and n are independently 1-3, provided that when $X^1$ is —$O(CR^{19}R^{20})_m$SH, then m is 2 or 3;

$R^{17}$, $R^{18}$, $R^{19}$, $R^{20}$, $R^{22}$, $R^{23}$ and $R^{25}$ are independently hydrogen, $C_1$-$C_6$ alkyl, $C_2$-$C_6$ alkenyl, $C_2$-$C_6$ alkynyl, aryl, heteroaryl, carbocycle, heterocycle, halo, hydroxy, sulfhydryl, nitro, amino or $C_1$-$C_6$ alkoxy, wherein said alkyl, alkenyl, alkynyl, aryl, heteroaryl, carbocycle, heterocycle and alkoxy are independently unsubstituted or substituted with one or more substituent(s); and $Y^1$ is —COOH oriented meta or para relative to C-1.

Preferably, when X is —PO(OH)$OR^{22}$ or —$(CR^{17}R^{18})_n$P (O) (OH)$OR^{22}$, then $R^{22}$ is not H or methyl; when X is —NH(P(O)($R^{23}$)OH or —$(CR^{17}R^{18})_n$NH(P(O) (OH)$R^{23}$), then $R^{23}$ is not benzyl unsubstituted or substituted with amino; and when X is —CON($R^{22}$)(OH), then $R^{22}$ is not H or methyl In another embodiment of formula VI, $X^1$ is oriented meta relative to C-1, and $Y^1$ is oriented ortho relative to $X^1$ and para relative to C-1. Preferably, W is a bond, —$(CH_2)_n$— NH—$(CH_2)_m$— or —$(CH_2)_n$—; m is 1-3; n is 0-3; and $Z^1$ is —$CO_2$H, —$NO_2$, —$SO_3$H, halo, $C_5$-$C_6$ heteroaryl, carboxyphenylthio, or mono- or di-carboxyphenylsulfonyl.

Examples of this embodiment are:
2-[(4-carboxyphenyl)sulfonyl]-1,4-benzene-dicarboxylic acid;
2-[(2,5-dicarboxyphenyl)sulfonyl]-1,4-benzene-dicarboxylic acid;
1,2,4-benzenetricarboxylic acid;
2-[(2-carboxyphenyl)thio]-1,4-benzenedicarboxylic acid;
2-nitro-1,4-benzenedicarboxylic acid;
2-bromo-1,4-benzenedicarboxylic acid;
2-amino-1,4-benzenedicarboxylic acid;
2-sulfoterephthalic acid, monosodium salt;
2-carboxymethyl-1,4-benzenedicarboxylic acid;
2-[(2-furanylmethyl)-amino]-1,4-benzenedicarboxylic acid;
2-[(carboxymethyl)amino]-1,4-benzenedicarboxylic acid; and
enantiomers and pharmaceutically acceptable equivalents.

In another embodiment of formula VI, $X^1$ is oriented ortho relative to C-1, and $Y^1$ is oriented para relative to $X^1$ and meta relative to C-1. Preferably, (1) when W is a bond, then $Z^1$ is —$CO_2$H, —OH, —$NO_2$, —C(O) (NH$R^{23}$), —$SR^{23}$, —$COR^{23}$ or —NH ($CH_2R^{23}$), and $R^{23}$ is an aryl or a heteroaryl wherein said aryl and heteroaryl are independently unsubstituted or substituted with one or more alkyl, nitro or carboxy group(s); and (2) when W is —$(CH_2)_n$— and n is 1-3, then $Z^1$ is —SH.

Examples of this embodiment are:
4-(4-nitrobenzoyl)-1,3-benzenedicarboxylic acid;
4-[4-(2,4-dicarboxybenzoyl)phenoxy]-1,2-benzene-dicarboxylic acid;
4-[[(2,4,6-trimethylphenyl)amino]carbonyl]-1,3-benzenedicarboxylic acid;
4-nitro-1,3-benzenedicarboxylic acid;
4-[(1-naphthalenylamino)-carbonyl]-1,3-benzene-dicarboxylic acid;
1,2,4-benzenetricarboxylic acid;
4-[(2-carboxyphenyl)thio]-1,3-benzenedicarboxylic acid;
4-[3-[[3-(2,4-dicarboxyphenoxy)propyl]dithio]-propoxy]-1,3-benzenedicarboxylic acid;
4-hydroxy-1,3-benzenedicarboxylic acid;
4-[(2-furanylmethyl)amino]-1,3-benzenedicarboxylic acid;
4-(2-mercaptoethyl)-1,3-benzenedicarboxylic acid; and
enantiomers and pharmaceutically acceptable equivalents.

In another embodiment of formula VI, $X^1$ is oriented meta relative to C-1, and $Y^1$ is oriented meta relative to $X^1$ and meta relative to C-1. Preferably, (1) when W is a bond, —$(CH_2)_n$— or —$O(CH_2)_m$— and m and n are independently 0-3, then $Z^1$ is —$SO_3$H, —$NO_2$, —$NH_2$, —$CO_2$H, —OH, —$PO_3$H, —CO(NHOH) or —SH; (2) when W is —$(CH_2)_n$NH$(CH_2)_m$— and m and n are independently 0-3, then $Z^1$ is —$CO_2$H or $C_5$-$C_6$ heteroaryl; and (3) when W is a bond, then $Z^1$ is either (a) a heteroaryl that is unsubstituted or substituted with an aryl that is unsubstituted or substituted with one or more $C_1$-$C_3$ alkyl, halo, nitro or hydroxy group(s), or (b) —$SO_2$(NHR$^{24}$) or —NH (COR$^{24}$), wherein $R^{24}$ is an aryl that is unsubstituted or substituted with one or more nitro, amino, halo or hydroxy group(s).

Examples of this embodiment are:

5-[4,5-dihydro-5-(4-hydroxyphenyl)-3-phenyl-1H-pyrazol-1-yl]-1,3-benzenedicarboxylic acid;

5-(4,5-dihydro-3-methyl-5-phenyl-1H-pyrazol-1-yl)-1,3-benzenedicarboxylic acid;

5-[[(4-chloro-3-nitrophenyl)amino]sulfonyl]-1,3-benzenedicarboxylic acid;

5-[[[4-chloro-3-[[3-(2-methoxyphenyl)-1,3-dioxopropyl]amino]phenyl]amino]sulfonyl-1,3-benzenedicarboxylic acid;

5-[[3-[4-(acetylamino)phenyl]-1,3-dioxopropyl]amino]-1,3-benzenedicarboxylic acid;

5-acetylamino-1,3-benzenedicarboxylic acid;

5-[[(1-hydroxy-2-naphthalenyl)carbonyl]-methylamino]-1,3-benzenedicarboxylic acid;

5-(4-carboxy-2-nitrophenoxy)-1,3-benzenedicarboxylic acid;

enantiomers and pharmaceutically acceptable equivalents.

Formula VII

Another preferred NAALADase inhibitor is a compound of formula VII

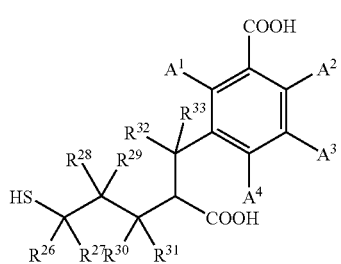

or an enantiomer or a pharmaceutically acceptable equivalent of said compound, wherein:

$R^{26}$, $R^{27}$, $R^{28}$, $R^{29}$, $R^{30}$, $R^{31}$, $R^{32}$ and $R^{33}$ are independently hydrogen or $C_1$-$C_3$ alkyl;

$A^1$, $A^2$, $A^3$ and $A^4$ are independently hydrogen, $C_1$-$C_6$ alkyl, $C_1$-$C_6$ alkoxy, halo, nitro, phenyl, phenoxy, benzyl, benzyloxy or —COOH, or any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

In one embodiment, $R^{26}$, $R^{27}$, $R^{28}$, $R^{29}$, $R^{30}$, $R^{31}$, $R^{32}$ and $R^{33}$ are independently hydrogen or methyl; and $A^1$, $A^2$, $A^3$ and $A^4$ are independently hydrogen, $C_1$-$C_4$ alkyl, $C_1$-$C_2$ alkoxy, halo, nitro, phenyl, phenoxy, benzyloxy, nitro or —COOH.

In another embodiment, any adjacent two of $A^2$, $A^3$ and $A^4$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

Formula VIII

Another preferred NAALADase inhibitor is a compound of formula VIII

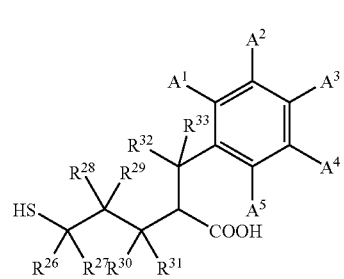

or an enantiomer or a pharmaceutically acceptable equivalent of said compound, wherein:

$R^{26}$, $R^{27}$, $R^{28}$, $R^{29}$, $R^{30}$, $R^{31}$, $R^{32}$, $R^{33}$ are independently hydrogen or $C_1$-$C_3$ alkyl; and $A^1$, $A^2$, $A^3$, $A^4$ and $A^5$ are independently hydrogen, $C_1$-$C_6$ alkyl, $C_1$-$C_6$ alkoxy, $C_1$-$C_3$ perhaloalkyl, phenyl, phenoxy, benzyl, benzyloxy, hydroxy, halo, cyano, nitro, —$SO_2R^{34}$, —(C=O)NR$^{34}$R$^{35}$, —(C=O)NR$^{34}$(CH$_2$)$_n$COOH, —NR$^{34}$(C=O)R$^{35}$, —(CH$_2$)$_n$COOH 5-sulfo-1,3-benzenedicarboxylic acid;

5-nitro-1,3-benzenedicarboxylic acid;

5-amino-1,3-benzenedicarboxylic acid;

1,3,5-benzenetricarboxylic acid;

5-[[(3-amino-4-chlorophenyl)amino]sulfonyl]-1,3-benzenedicarboxylic acid;

5-(3-mercaptopropoxy)-1,3-benzenedicarboxylic acid;

5-hydroxy-1,3-benzenedicarboxylic acid;

5-(2-mercaptoethoxy)-1,3-benzenedicarboxylic acid;

5-[(hydroxyamino)carbonyl]-1,3-benzenedicarboxylic acid;

5-phosphono-1,3-benzenedicarboxylic acid;

5-mercaptomethyl-1,3-benzenedicarboxylic acid;

5-phosphonomethyl-1,3-benzenedicarboxylic acid;

5-[[(carboxymethyl)amino]-methyl]-1,3-benzene-dicarboxylic acid;

5-[(carboxymethyl)amino]-1,3-benzenedicarboxylic acid;

5-[[(2-furanylmethyl)amino]-methyl]-1,3-benzene-dicarboxylic acid;

5-[2-(hydroxyamino)-2-oxoethyl]-1,3-benzene-dicarboxylic acid;

5-(2-mercaptoethyl)-1,3-benzenedicarboxylic acid; and or —COOH, or any adjacent two of $A^1$, $A^2$, $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s);

$R^{34}$ and $R^{35}$ are independently hydrogen, $C_1$-$C_6$ alkyl, phenyl or benzyl; and n is 1-3.

Preferably, if $A^1$, $A^3$ and $A^5$ are independently hydrogen, $C_1$-$C_6$ alkyl, $C_1$-$C_6$ alkoxy, halo, nitro, phenyl, phenoxy, benzyl, benzyloxy or -COOH, then neither $A^2$ nor $A^4$ are —COOH; and if any adjacent two of $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s), then $A^2$ is not —COOH.

In one embodiment, $R^{26}$, $R^{27}$, $R^{28}$, $R^{29}$, $R^{30}$, $R^{31}$, $R^{32}$ and $R^{33}$ are each hydrogen; $A^1$, $A^2$, $A^3$, $A^4$ and $A^5$ are independently hydrogen, $C_1$-$C_4$ alkyl, $C_1$-$C_2$ alkoxy, $C_1$-$C_2$ perhaloalkyl, phenyl, phenoxy, hydroxy, halo, cyano, nitro, —$SO_2R^{34}$, —(C=O)$NR^{34}R^{35}$, —(C=O)$NR^{34}$(CH$_2$)COOH, —$NR^{34}$(C=O)$R^{35}$ or —(CH$_2$)COOH; and $R^{34}$ and $R^{35}$ are independently hydrogen, methyl or benzyl.

In another embodiment, any adjacent two of $A^1$, $A^2$, $A^3$, $A^4$ and $A^5$ form with the benzene ring a fused 5- or 6-membered carbocyclic or heterocyclic aromatic ring, said heterocyclic aromatic ring containing 1 or 2 oxygen, nitrogen and/or sulfur heteroatom(s).

Formula IX

Another preferred NAALADase inhibitor is a compound of formula IX

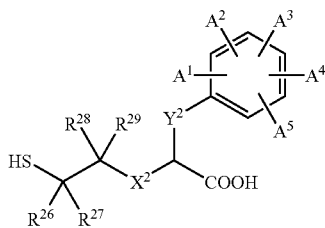

IX or an enantiomer or a pharmaceutically acceptable equivalent of said compound, wherein:

$X^2$ and $Y^2$ are independently —$CR^{30}R^{31}$, —O—, —S— or —$NR^{30}$—, provided that at least one of $X^2$ and $Y^2$ is/are —$CR^{30}R^{31}$—;

$A^1$, $A^2$, $A^3$, $A^4$ and $A^5$ are independently hydrogen, $C_1$-$C_9$ alkyl, $C_2$-$C_9$ alkenyl, $C_2$-$C_9$ alkynyl, aryl, heteroaryl, carbocycle, heterocycle, $C_1$-$C_9$ alkoxy, $C_2$-$C_9$ alkenyloxy, phenoxy, benzyloxy, hydroxy, halo, nitro, cyano, isocyano, —$COOR^{34}$, —$COR^{34}$, —$NR^{34}R^{35}$, —$SR^{34}$, —$SOR^{34}$, —$SO_2R^{34}$, —$SO_2(OR^{34})$, —(C=O)$NR^{34}R^{35}$, —(C=O)$NR^{34}$(CH$_2$)$_n$COOH, —$NR^{34}$ (C=O)$R^{35}$ or —(CH$_2$)$_n$COOH, or any adjacent two of $A^1$, $A^2$, $A^3$, $A^4$ and $A^5$ form with the benzene ring a fused ring that is saturated or unsaturated, aromatic or non-aromatic, and carbocyclic or heterocyclic, said heterocyclic ring containing 1 or 2 oxygen, nitrogen and/or sulfur heteroatom(s);

n is 1-3; and $R^{26}$, $R^{27}$, $R^{28}$, $R^{29}$, $R^{30}$, $R^{31}$, $R^{34}$ and $R^{35}$ are independently hydrogen, $C_1$-$C_9$ alkyl, $C_2$-$C_9$ alkenyl, $C_2$-$C_9$ alkynyl, aryl, heteroaryl, carbocycle or heterocycle; and said alkyl, alkenyl, alkynyl, aryl, heteroaryl, carbocycle, heterocycle, alkoxy, alkenyloxy, phenoxy, benzyloxy, and fused ring are independently unsubstituted or substituted with one or more substituent(s).

Preferably, if $A^1$, $A^2$ and $A^3$ are each hydrogen, and $A^4$ and $A^5$ are each —COOH, then $A^4$ is ortho to $A^5$; and if $Y^3$ is —$CR^{30}R^{31}$—, then at least one of $A^1$, $A^2$, $A^3$, $A^4$ and $A^5$ is/are independently phenoxy, benzyloxy, aryl, heteroaryl, carbocycle or heterocycle that is substituted with one or more substituent(s).

In one embodiment, $Y^2$ is —O—, —S— or —$NR^{30}$—; $A^1$, $A^2$, $A^3$, $A^4$ and $A^5$ are independently hydrogen, $C_1$-$C_4$ alkyl, $C_1$-$C_2$ alkoxy, hydroxy, halo, —COOH, —$COR^{34}$ —$NR^{34}$ (C=O)$R^{35}$ or —(CH$_2$)COOH; and $R^{34}$ and $R^{35}$ are independently hydrogen or methyl.

In another embodiment, $Y^2$ is —$CR^{30}R^{31}$—; $A^1$, $A^2$, $A^3$ and $A^4$ are each hydrogen; and As is phenoxy, benzyloxy, aryl, heteroaryl, carbocycle or heterocycle, wherein said phenoxy and benzyloxy are substituted with —COOH, and said aryl, heteroaryl, carbocycle and heterocycle are independently substituted with one or more substituent(s) selected from the group consisting of cyano and —COOH.

Formula X

Another preferred NAALADase inhibitor is a compound of formula X

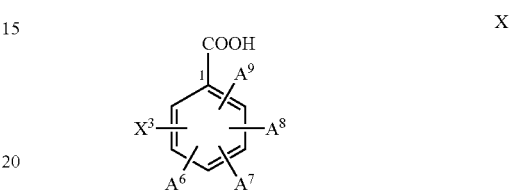

X or an enantiomer or a pharmaceutically acceptable equivalent of said compound, wherein:

$X^3$ is —(CR$^{36}$R$^{37}$)$_n$SH, —O(CR$^{36}$R$^{37}$)$_2$SH, —S(CR$^{36}$R$^{37}$)$_2$SH or —NR(CR$^{36}$R$^{37}$)$_2$SH;

n is 1-3; and

R, $R^{36}$, $R^{37}$, $A^6$, $A^7$, $A^8$ and $A^9$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkylsulfonyl, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenoxy, phenoxy and benzyloxy are independently unsubstituted or substituted with one or more substituent(s).

Preferred compounds of formula X are selected from the group consisting of:

3-(2-mercaptoethyl)-benzoic acid;
3-(mercaptomethyl)-benzoic acid;
2-(mercaptomethyl)-benzoic acid;
5-hydroxy-2-(2-mercaptoethyl)-benzoic acid;
2-(2-mercaptoethyl)-benzoic acid;
5-[(4-carboxyphenyl)methoxy]-2-(2-mercaptoethyl)-benzoic acid;
2-(2-mercaptoethyl)-5-(phenylmethoxy)-benzoic acid;
2-(carboxymethoxy)-6-(2-mercaptoethyl)-benzoic acid;
5-[(3-carboxyphenyl)methoxy]-2-(2-mercaptoethyl)-benzoic acid;
2-(2-mercaptoethyl)-6-(phenylmethoxy)-benzoic acid;
2-[(2-carboxyphenyl)methoxy]-6-(2-mercaptoethyl)-benzoic acid;
2-[(4-carboxyphenyl)methoxy]-6-(2-mercaptoethyl)-benzoic acid;
3-(2-mercaptoethyl)-[1,1'-biphenyl]-2,3'-dicarboxylic acid;
2-(3,3-dimethylbutoxy)-6-(2-mercaptoethyl)-benzoic acid;
2-(2-mercaptoethyl)-6-(2-phenylethoxy)-benzoic acid;
2-[(2-chlorophenyl)methoxy]-6-(2-mercaptoethyl)-benzoic acid;
2-[[3-carboxy-5-(1,1-dimethylethyl)phenyl]methoxy]-6-(2-mercaptoethyl)-benzoic acid;
2-(2-mercaptoethyl)-6-phenoxy-benzoic acid;
2-(2-mercaptoethyl)-6-phenylamino-benzoic acid;

2-(2-mercaptoethyl)-6-(phenylthio)-benzoic acid;

5'-(1,1-dimethylethyl)-3-(2-mercaptoethyl)-[1,1'-biphenyl]-2,3'-dicarboxylic acid;

3-(2-mercaptoethyl)-[1,1'-biphenyl]-2,4'-dicarboxylic acid;

2-[(4-carboxy-2-methoxyphenyl)methoxy]-6-(2-mercaptoethyl)-benzoic acid;

2-[(4-carboxy-3-methoxyphenyl)methoxy]-6-(2-mercaptoethyl)-benzoic acid;

2-[(2-bromo-4-carboxyphenyl)methoxy]-6-(2-mercaptoethyl)-benzoic acid;

2-[(3-bromo-4-carboxyphenyl)methoxy]-6-(2-mercaptoethyl)-benzoic acid;

2-[(4-chlorophenyl)methoxy]-6-(2-mercaptoethyl)-benzoic acid;

2-(biphenyl-2-ylmethoxy)-6-(2-mercaptoethyl)-benzoic acid;

2-[(3-bromo-5-carboxyphenyl)methoxy]-6-(2-mercaptoethyl)-benzoic acid;

2-[(2-bromo-5-carboxyphenyl)methoxy]-6-(2-mercaptoethyl)-benzoic acid;

2-(2-mercaptoethyl)-6-[(4-methoxyphenyl)methoxy]-benzoic acid;

2-(2-mercaptoethyl)-6-[(4-methylphenyl)methoxy]-benzoic acid;

2-[(4-bromo-3-carboxyphenyl)methoxy]-6-(2-mercaptoethyl)-benzoic acid;

2-[(2-carboxy-5-methoxyphenyl)methoxy]-6-(2-mercaptoethyl)-benzoic acid;

5-(mercaptomethyl)-2-(2-phenylethoxy)-benzoic acid;

2-bromo-5-(mercaptomethyl)-benzoic acid;

4-(mercaptomethyl)-[1,1'-biphenyl]-2,3'-dicarboxylic acid;

5-(mercaptomethyl)-2-(phenylmethoxy)-benzoic acid; and 4-bromo-3-(mercaptomethyl)-benzoic acid; and enantiomers and pharmaceutically acceptable equivalents.

Formula XI

Another preferred NAALADase inhibitor is a compound of formula XI

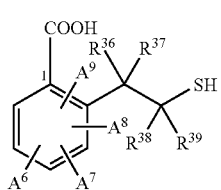

or an enantiomer or a pharmaceutically acceptable equivalent of said compound, wherein:

$R^{37}$, $R^{38}$, $R^{39}$ and $R^{40}$ are independently hydrogen or $C_1$-$C_3$ alkyl; and $A^6$, $A^7$, $A^8$ and $A^9$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkylsulfonyl, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenoxy, phenoxy and benzyloxy are independently unsubstituted or substituted with one or more substituent(s).

In one embodiment, $R^{36}$, $R^{37}$, $R^{38}$ and $R^{39}$, $A^7$, $A^8$ and $A^9$ are each hydrogen; $A^6$ is hydrogen, —$(CH_2)_n$—$W^1$, or —$Y^3$—$(CH_2)_n$—$W^1$; n is 0-3; $Y^3$ is O, S or $NR^{40}$; $R^{40}$ is hydrogen or $C_1$-$C_4$ alkyl; $W^1$ is $C_1$-$C_6$ alkyl or phenyl, wherein $W^1$ is unsubstituted or substituted with $C_1$-$C_4$ alkyl, $C_1$-$C_4$ alkoxy, carboxy or halo.

Formula XII

Another preferred NAALADase inhibitor is a compound of formula XII

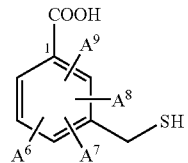

or an enantiomer or a pharmaceutically acceptable equivalent of said compound, wherein:

$A^6$, $A^7$, $A^8$ and $A^9$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkylsulfonyl, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenoxy, phenoxy and benzyloxy are independently unsubstituted or substituted with one or more substituent(s).

Preferably, at least one of $A^6$, $A^7$, $A^8$ and $A^9$ is/are not hydrogen; and if $A^6$ is chloro, fluoro, amino or thiomethyl, then at least one of $A^7$, $A^8$ and $A^9$ is/are not hydrogen.

In one embodiment, $A^7$, $A^8$ and $A^9$ are each hydrogen; $A^6$ is —$(CH_2)_n$—$Ar^2$ or —$Y^3$—$(CH_2)_n$—$Ar^2$; n is 0-3; $Y^3$ is O, S or $NR^{41}$; $R^{41}$ is hydrogen or $C_1$-$C_4$ alkyl; and $Ar^2$ is phenyl, wherein $Ar^2$ is unsubstituted or substituted with $C_1$-$C_4$ alkyl, carboxy or halo.

Formula XIII

Another preferred NAALADase inhibitor is a compound of formula XIII

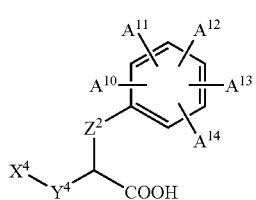

or an enantiomer pharmaceutically acceptable equivalent of said compound, wherein:

$X^4$ is —(CO)NHOH or —N(OH)COH;

$Y^4$ is a bond or a divalent linking group having from 1 to 9 carbon atom(s) and from 0 to 5 heteroatom(s) independently selected from the group consisting of oxygen, sulfur and nitrogen;

$X^2$ is —$CR^{41}R^{42}$—, —$NR^{41}$—, —O— or —S—;

$A^{10}$, $A^{11}$, $A^{12}$, $A^{13}$ and $A^{14}$ are independently hydrogen, $C_1$-$C_9$ alkyl, $C_2$-$C_9$ alkenyl, $C_2$-$C_9$ alkynyl, aryl, heteroaryl, carbocycle, heterocycle, $C_1$-$C_9$ alkoxy, $C_2$-$C_9$ alkenyloxy, phenoxy, benzyloxy, hydroxy, halo, nitro, cyano, isocyano, —$COOR^{43}$, —$COR^{43}$, —$NR^{43}R^{44}$, —$SR^{43}$, —$SOR^{43}$, —$SO_2R^{43}$, —$SO_2(OR^{43})$, —$(CO)NR^{43}R^{43}$, —$(CO)NR^{43}(CH_2)_nCOOH$, —$NR^{43}(CO)R^{44}$ or —$(CH_2)_nCOOH$, or any adjacent two of $A^{10}$, $A^{11}$, $A^{12}$ and $A^{13}$ form with the benzene ring a fused ring that is saturated or unsaturated, aromatic or non-aromatic, and carbocyclic or heterocyclic, said heterocyclic ring containing 1 or 2 oxygen, nitrogen and/or sulfur heteroatom(s);

n is 1-3;

$R^{41}$, $R^{42}$, $R^{43}$ and $R^{44}$ are independently hydrogen, $C_1$-$C_9$ alkyl, $C_2$-$C_9$ alkenyl, $C_2$-$C_9$ alkynyl, aryl, heteroaryl, carbocycle or heterocycle; and said alkyl, alkenyl, alkynyl, aryl, heteroaryl, carbocycle, heterocycle, alkoxy, alkenyloxy, phenoxy, benzyloxy, and fused ring are independently unsubstituted or substituted with one or more substituent(s).

In one embodiment, $Y^4$ is —$(CR^{45}R^{46})_p$—$W^2$—$(CR^{47}R^{48})_q$—; $W^2$ is —$CR^{49}R^{50}$—, —$NR^{49}$—, —O—, —S— or —$SO_2$—; p and q are independently 0-4, provided that when q is 0 and $W^2$ is —$NR^{49}$—, —O—, —S— or —$SO_2$—, then $Z^2$ is —$CR^{41}R^{42}$—; $R^{45}$, $R^{46}$, $R^{47}$, $R^{48}$, $R^{49}$ and $R^{50}$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenyloxy, phenoxy and benzyloxy are independently unsubstituted or substituted with one or more substituent (s); and $A^{10}$, $A^{11}$ and $A^{12}$ are each hydrogen.

In another embodiment, $Y^4$ is —$(CR^{45}R^{46})_p$—$W^2$—$(CR^{47}R^{48})_q$—; $W^2$ is —$CR^{49}R^{50}$—; p is 0-4; q is 0; $R^{45}$, $R^{46}$, $R^{47}$, $R^{48}$, $R^{49}$ an $R^{50}$ are each hydrogen; $A^{10}$, $A^{11}$ and $A^{12}$ are each hydrogen; $A^{13}$ is hydrogen, —$COOR^{43}$, $C_1$-$C_4$ alkyl, $C_2$-$C_4$ alkenyl or $C_2$-$C_4$ alkynyl; and $A^{14}$ is —$COR^{43}$.

In another embodiment, $Y^4$ is —$(CR^{45}R^{46})_p$—$W^2$—$(CR^{47}R^{48})_q$—; $W^2$ is —S—; p and q are independently 1-4; $R^{45}$, $R^{46}$, $R^{47}$, $R^{48}$, $R^{49}$ and $R^{50}$ are independently hydrogen, $C_1$-$C_4$ alkyl, $C_2$-$C_4$ alkenyl, $C_2$-$C_4$ alkynyl or phenyl; $A^{10}$, $A^{11}$ and $A^{12}$ are each hydrogen; $A^{13}$ is hydrogen, $C_1$-$C_4$ alkyl, $C_2$-$C_4$ alkenyl, $C_2$-$C_4$ alkynyl, phenyl, benzyl, phenoxy, benzyloxy or halo, wherein said alkyl, alkenyl, alkynyl, phenyl, benzyl, phenoxy and benzyloxy are independently unsubstituted or substituted with carboxy; and $A^{14}$ is —COOH.

In another embodiment, $Y^4$ is —$(CR^{45}R^{46})_p$—$W^2$—$(CR^{47}R^{48})_q$—; $W^2$ is —$CR^{49}R^{50}$—, —$NR^{49}$—, —O—, —S— or —$SO_2$—; p and q are independently 0-4, provided that when q is 0 and $W^2$ is —$NR^{49}$—, —O—, —S— or —$SO_2$—, then $Z^2$ is —$CR^{41}R^{42}$—; $R^{44}$, $R^{46}$, $R^{47}$, $R^{48}$, $R^{49}$ and $R^{50}$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenyloxy, phenoxy and benzyloxy are independently unsubstituted or substituted with one or more substituent (s); $A^{10}$, $A^{11}$ and $A^{12}$ are each hydrogen; is hydrogen; and $A^{14}$ is benzyl or carboxybenzyl.

Formula XIV

Another preferred NAALADase inhibitor is a compound of formula XIV

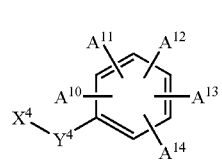

or an enantiomer or a pharmaceutically acceptable equivalent of said compound, wherein:

$X^4$ is —(CO)NHOH or —N(OH)COH;

$Y^4$ is a bond or a divalent linking group having from 1 to 9 carbon atom(s) and from 0 to 5 heteroatom(s) independently selected from the group consisting of oxygen, sulfur and nitrogen;

$A^{10}$, $A^{11}$, $A^{12}$, $A^{13}$ and $A^{14}$ are independently hydrogen, $C_1$-$C_9$ alkyl, $C_2$-$C_9$ alkenyl, $C_2$-$C_9$ alkynyl, aryl, heteroaryl, carbocycle, heterocycle, $C_1$-$C_9$ alkoxy, $C_2$-$C_9$ alkenyloxy, phenoxy, benzyloxy, hydroxy, halo, nitro, cyano, isocyano, —$COOR^{43}$, —$COR^{43}$, —$NR^{43}R^{44}$, —$SR^{43}$, —$SOR^{43}$, —$SO_2R^{43}$, —$SO_2(OR^{43})$, —$(CO)NR^{43}R^{44}$, —(CO) $NR^{43}(CH_2)_nCOOH$, —$NR^{43}(CO)R^{44}$ or —$(CH_2)_nCOOH$, or any adjacent two of $A^{10}$, $A^{11}$, $A^{12}$ and $A^{13}$ form with the benzene ring a fused ring that is saturated or unsaturated, aromatic or non-aromatic, and carbocyclic or heterocyclic, said heterocyclic ring containing 1 or 2 oxygen, nitrogen and/or sulfur heteroatom(s);

n is 1-3;

$R^{43}$ and $R^{44}$ are independently hydrogen, $C_1$-$C_9$ alkyl, $C_2$-$C_9$ alkenyl, $C_2$-$C_9$ alkynyl, aryl, heteroaryl, carbocycle or heterocycle; and said alkyl, alkenyl, alkynyl, aryl, heteroaryl, carbocycle, heterocycle, alkoxy, alkenyloxy, phenoxy, benzyloxy, and fused ring are independently unsubstituted or substituted with one or more substituent(s).

In one embodiment, $Y^4$ is a bond or —$(CR^{45}R^{46})_p$—$W^2$—$(CR^{47}R^{48})_q$—; $W^2$ is —$CR^{49}R^{50}$—, —$NR^{49}$—, —O—, —S— or —$SO_2$—; p and q are independently 0-4; $R^{45}$, $R^{46}$, $R^{47}$, $R^{48}$, $R^{49}$ and $R^{50}$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulhydryl, nitro, amino, cyano, isocyano, thiocyano, isothiocyano, formamido, thioformamido, sulfo, sulfino, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenyloxy, phenoxy and benzyloxy are independently unsubstituted or substituted with one or more substituent (s); and $A^{10}$, $A^{11}$ and $A^{12}$ are each hydrogen.

In another embodiment, $Y^4$ is a bond; $A^{10}$, $A^{11}$ and $A^{12}$ are each hydrogen; $A^{13}$ is hydroxy, phenoxy, benzyloxy, —$COOR^{43}$ or —$(CO)NHR^{44}$; $A^{14}$ is —$COOR^{43}$; $R^{43}$ is hydrogen, $C_1$-$C_4$ alkyl, $C_2$-$C_4$ alkenyl or $C_2$-$C_4$ alkynyl; $R^{44}$ is benzyl; and said benzyl, phenoxy and benzyloxy are independently unsubstituted or substituted with —$COOR^{43}$.

In another embodiment, $Y^4$ is —$(CR^{45}R^{46})_p$—$W^2$—$(CR^{47}R^{48})_q$—; $W^2$ is —O— or —S—; $R^{45}$, $R^{46}$, $R^{47}$ and $R^{48}$ are each hydrogen; $A^{10}$, $A^{11}$ and $A^{12}$ are each hydrogen; and $A^{13}$ is hydrogen, —COOH, phenyl or benzyloxy, wherein said phenyl and benzyloxy are independently unsubstituted or substituted with —$COOR^{43}$; and $A^{14}$ is —$COOR^{43}$.

In another embodiment, $Y^4$ is a bond or —$(CR^{45}R^{46})_p$—$W^2$—$(CR^{47}R^{48})_q$—; $W^2$ is —$CR^{49}R^{50}$—, —$NR^{49}$—, —O—, —S— or —$SO_2$—; p and q are independently 0-4; $R^{45}$, $R^{46}$, $R^{47}$, $R^{48}$, $R^{49}$ and $R^{50}$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenyloxy, phenoxy and benzyloxy are independently unsubstituted or substituted with one or more substituent(s); $A^{10}$, $A^{11}$ and $A^{12}$ are each hydrogen; $A^{13}$ is hydrogen, nitro or $C_1$-$C_4$ alkoxy; $A^{14}$ is hydroxy, phenoxy, benzyloxy, benzoyl or $C_1$-$C_4$ alkoxy, wherein said phenoxy, benzyloxy, benzoyl and alkoxy are independently unsubstituted or substituted with one or more substituent(s).

Formula XV

Another preferred NAALADase inhibitor is a compound of formula XV

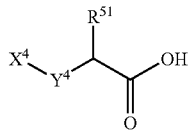

XV or an enantiomer or a pharmaceutically acceptable equivalent of said compound, wherein:

$X^4$ is —(CO)NHOH or —N(OH)COH;

$Y^4$ is a bond or a divalent linking group having from 1 to 9 carbon atom(s) and from 0 to 5 heteroatom(s) independently selected from the group consisting of oxygen, sulfur and nitrogen; and $R^{51}$ is hydrogen, $C_1$-$C_9$ alkyl, $C_2$-$C_9$ alkenyl, $C_2$-$C_9$ alkynyl, $C_1$-$C_9$ alkoxy or $C_2$-$C_9$ alkenoxy, wherein said alkyl, alkenyl, alkynyl, alkoxy and alkenoxy are independently unsubstituted or substituted with one or more substituent(s); provided that when Y is methylene, amine or oxygen, then $R^{51}$ is not carboxyethyl.

In one embodiment, $Y^4$ is —$(CR^{45}R^{46})_p$—$W^2$—$(CR^{47}R^{48})_q$—; $W^2$ is —$CR^{49}R^{50}$—, —$NR^{49}$—, —O—, —S— or —$SO_2$—; p and q are independently 0-4; and $R^{45}$, $R^{46}$, $R^{47}$, $R^{48}$, $R^{49}$ and $R^{50}$ are independently hydrogen, $C_1$-$C_9$ alkyl, $C_2$-$C_9$ alkenyl, $C_2$-$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$-$C_9$ alkoxy, $C_2$-$C_9$ alkenoxy, phenoxy or benzyloxy, wherein said alkyl, alkenyl, alkynyl, aryl, heteroaryl, carbocycle, heterocycle, alkoxy, alkenyloxy, phenoxy and benzyloxy are independently unsubstituted or substituted with one or more substituent(s).

In another embodiment, $Y^4$ is —$(CR^{45}R^{46})_p$—$W^2$—$(CR^{47}R^{48})_q$—; $W^2$ is —$CR^{49}R^{50}$— or —S—; p is 0-1; q is 0-3; and $R^{45}$, $R^{46}$, $R^{47}$, $R^{48}$, $R^{49}$ and $R^{50}$ are each hydrogen.

Representative compounds of formulas XIII-XV are set forth below in TABLE I.

TABLE I

| Structure | Name |
|---|---|
| (structure of 3-tert-butyl benzoic acid with hydroxycarbamoyl-propyl substituent) | 3-tert-Butyl-5-(2-carboxy-3-hydroxycarbamoyl-propyl)-benzoic acid |
| (structure of 3-tert-butyl benzoic acid with hydroxycarbamoyl-butyl substituent) | 3-tert-Butyl-5-(2-carboxy-4-hydroxycarbamoyl-butyl)-benzoic acid |

TABLE I-continued

| Structure | Name |
|---|---|
| 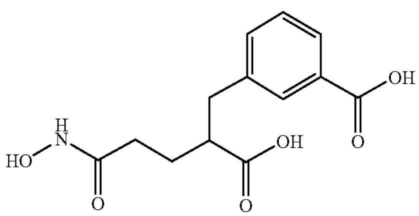 | 3-(2-Carboxy-4-hydroxycarbamoyl-butyl)-benzoic acid |
| 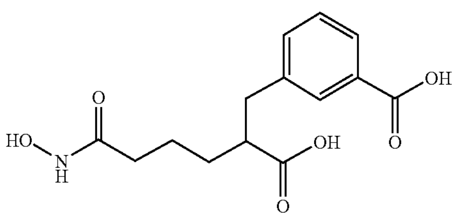 | 3-(2-Carboxy-5-hydroxycarbamoyl-pentyl)-benzoic acid |
| 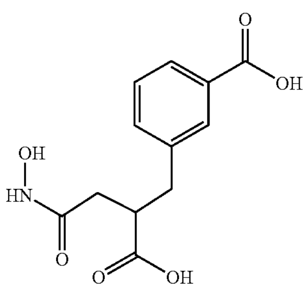 | 3-(2-Carboxy-3-hydroxycarbamoyl-propyl)-benzoic acid |
| 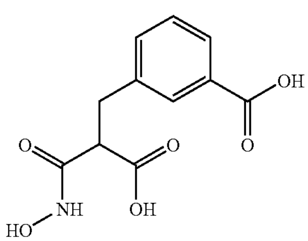 | 3-(2-Carboxy-2-hydroxycarbamoyl-ethyl)-benzoic acid |
| 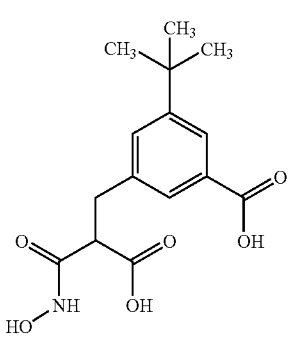 | 3-tert-Butyl-5-(2-carboxy-2-hydroxycarbamoyl-ethyl)-benzoic acid |

TABLE I-continued

| Structure | Name |
|---|---|
| 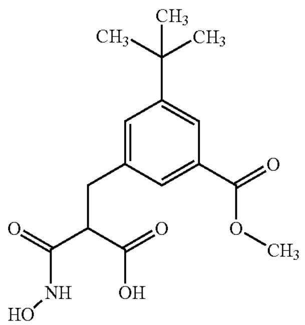 | 3-tert-Butyl-5-(2-carboxy-2-hydroxycarbamoyl-ethyl)-benzoic acid methyl ester |
| 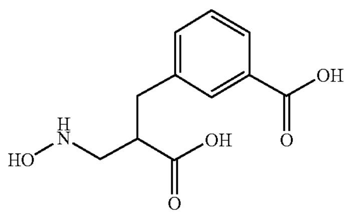 | 3-(2-Carboxy-2-hydroxyamino-propyl)-benzoic acid |
| 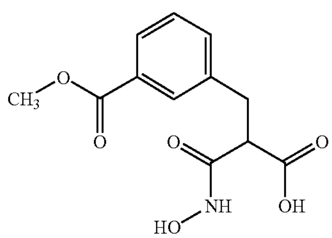 | 3-(2-Carboxy-2-hydroxycarbamoyl-ethyl)-benzoic acid methyl ester |
|  |  |
|  |  |

TABLE I-continued
| Structure | Name |
|---|---|
| 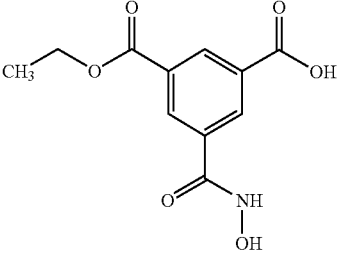 | 5-Hydroxycarbamoyl-isophthalic acid monoethyl ester |
| 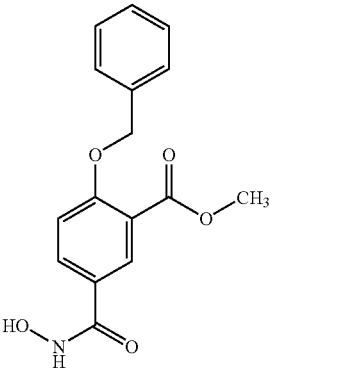 | 6-Benzyloxy-N-hydroxy-isophthalamic acid methyl ester |
| 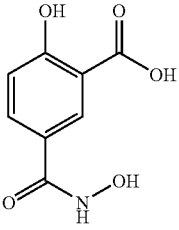 | 6,N-Dihydroxy-isophthalamic acid |
| 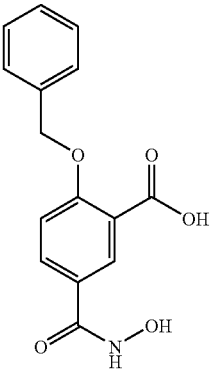 | 6-Benzyloxy-N-hydroxy-isophthalamic acid |
| 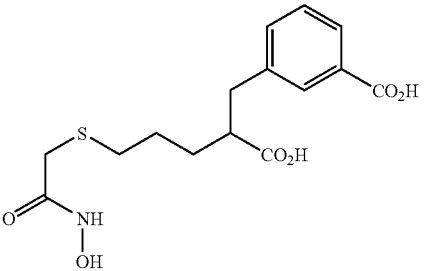 | 3-(2-Carboxy-5-hydroxycarbamoylmethyl-sulfanylpentyl)-benzoic acid |

TABLE I-continued

| Structure | Name |
|---|---|
| 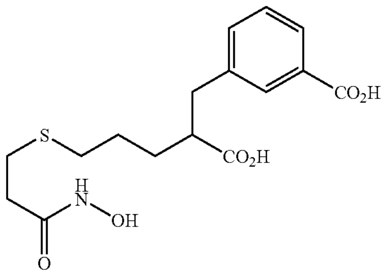 | 3-[2-Carboxy-5-(2-hydroxycarbamoyl-ethylsulfanyl)-pentyl]-benzoic acid |
| 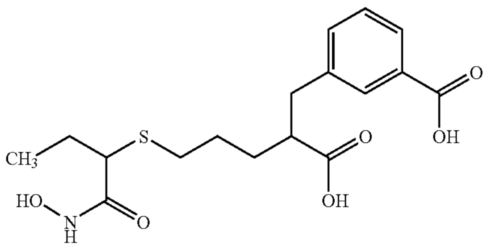 | 3-[2-Carboxy-5-(1-hydroxycarbamoyl-propylsulfanyl)-pentyl]-benzoic acid |
| 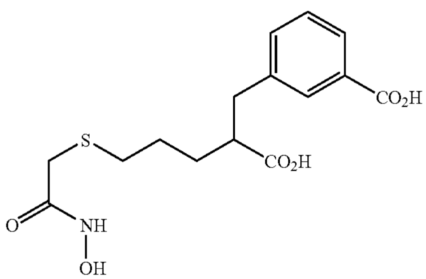 | 3-(2-Carboxy-5-hydroxycarbamoylmethyl-sulfanylpentyl)-benzoic acid |
| | 3-(2-Carboxy-5-hydroxycarbamoylmethylsulfanyl-pentyl)-benzoic acid |
| 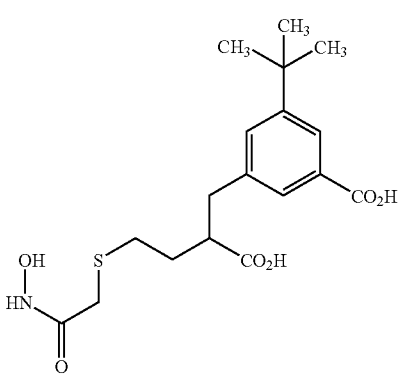 | 3-tert-Butyl-5-(2-carboxy-4-hydroxycarbamoylmethyl-sulfanylbutyl)-benzoic acid |

TABLE I-continued

| Structure | Name |
|---|---|
| 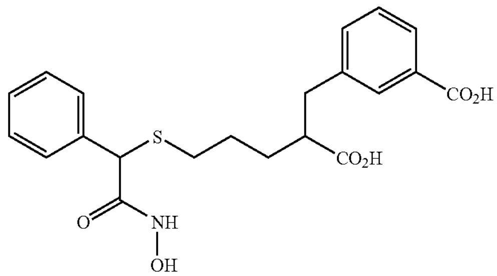 | 3-[2-Carboxy-5-(hydroxycarbamoyl-phenyl-methylsulfanyl)-pentyl]-benzoic acid |
| 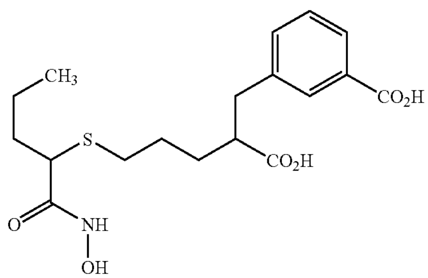 | 3-[2-Carboxy-5-(1-hydroxycarbamoyl-butylsulfanyl)-pentyl]-benzoic acid |
| 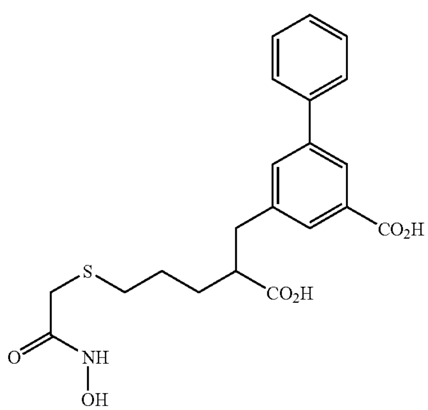 | 5-(2-Carboxy-5-hydroxycarbamoylmethyl-sulfanylpentyl)-biphenyl-3-carboxylic acid |
| 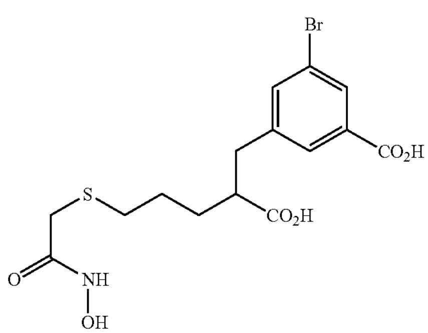 | 3-Bromo-5-(2-carboxy-5-hydroxycarbamoylmethyl-sulfanylpentyl)-benzoic acid |

TABLE I-continued

| Structure | Name |
|---|---|
| 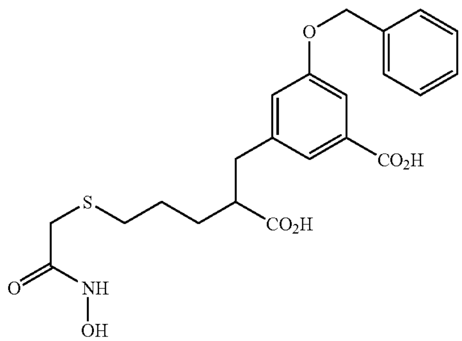 | 3-Benzyloxy-5-(2-carboxy-5-hydroxycarbamoylmethyl-sulfanylpentyl)-benzoic acid |
| 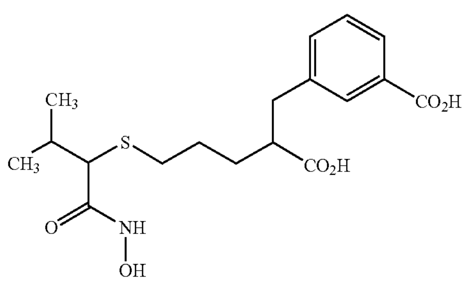 | 3-[2-Carboxy-5-(1-hydroxycarbamoyl-2-methyl-propylsulfanyl)-pentyl]-benzoic acid |
| 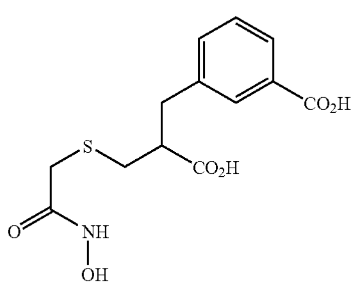 | 3-(2-Carboxy-3-hydroxycarbamoylmethyl-sulfanylpropyl)-benzoic acid |
| 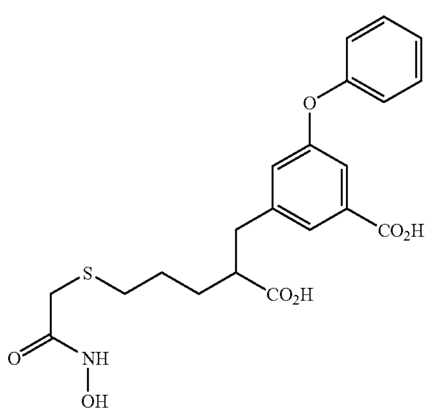 | 3-(2-Carboxy-5-hydroxycarbamoylmethyl-sulfanylpentyl)-5-phenoxy-benzoic acid |

TABLE I-continued

| Structure | Name |
|---|---|
| 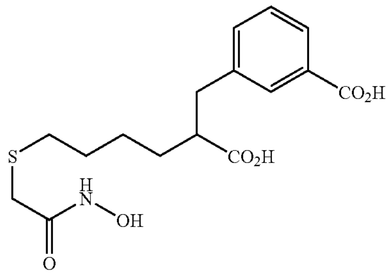 | 3-(2-Carboxy-6-hydroxycarbamoylmethyl-sulfanylhexyl)-benzoic acid |
| 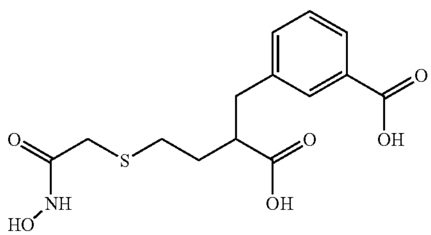 | 3-(2-Carboxy-4-hydroxycarbamoylmethyl-sulfanylbutyl)-benzoic acid |
| 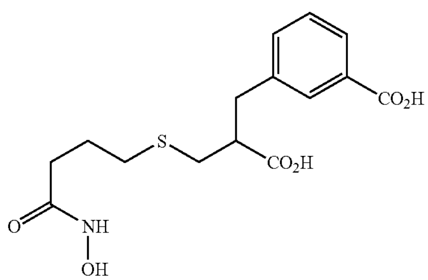 | 3-[2-Carboxy-3-(3-hydroxycarbamoyl-propylsulfanyl)-propyl]-benzoic acid |
| 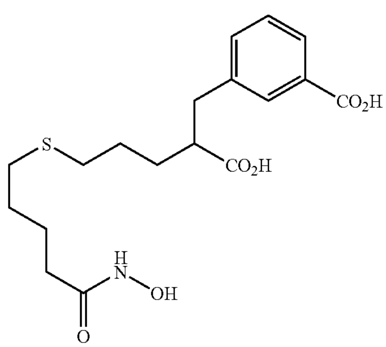 | 3-[2-Carboxy-5-(4-hydroxycarbamoyl-butylsulfanyl)-phenyl]-benzoic acid |
| 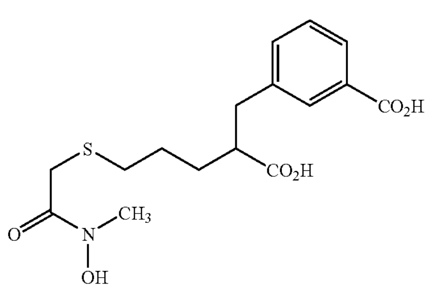 | 3-{2-Carboxy-5-[(hydroxy-methyl-carbamoyl)-methylsulfanyl]-pentyl}-benzoic acid |

TABLE I-continued

| Structure | Name |
|---|---|
| 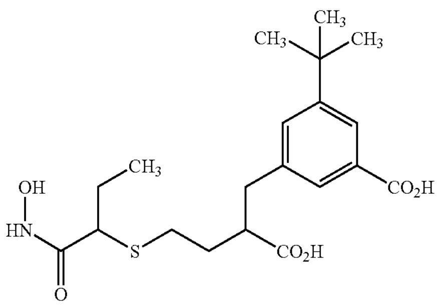 | 3-tert-Butyl-5-[2-carboxy-4-(1-hydroxycarbamoyl-propylsulfanyl)-butyl]-benzoic acid |
| 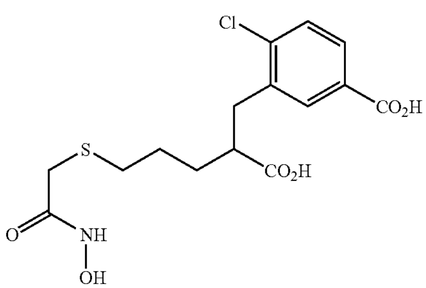 | 3-(2-Carboxy-5-hydroxycarbamoylmethyl-sulfanylpentyl)-4-chloro-benzoic acid |
| 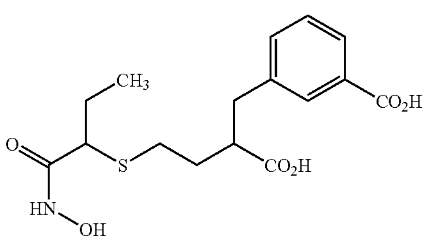 | 3-[2-Carboxy-4-(1-hydroxycarbamoyl-propylsulfanyl)-butyl]-benzoic acid |
| 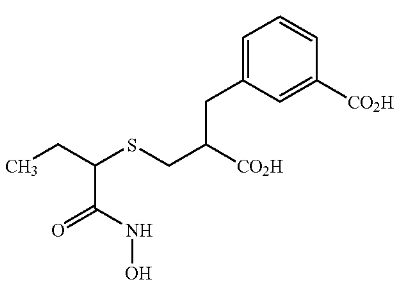 | 3-[2-Carboxy-3-(1-hydroxycarbamoyl-propylsulfanyl)-propyl]-benzoic acid |
| 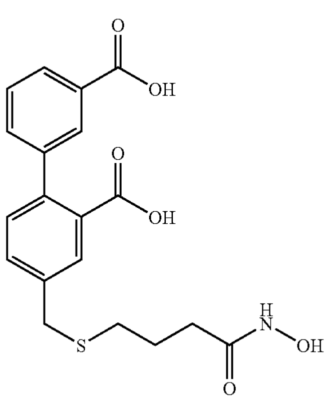 | 4-(3-Hydroxycarbamoyl-propylsulfanylmethyl)-biphenyl-2,3'-dicarboxylic acid |

TABLE I-continued

| Structure | Name |
|---|---|
| 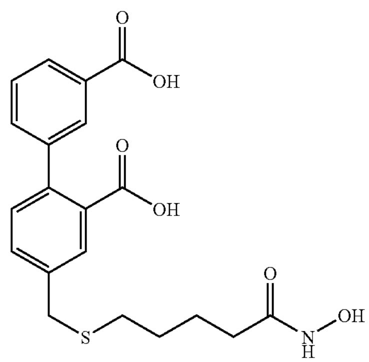 | 4-(4-Hydroxycarbamoyl-butylsulfanylmethyl)-biphenyl-2,3'-dicarboxylic acid |
| 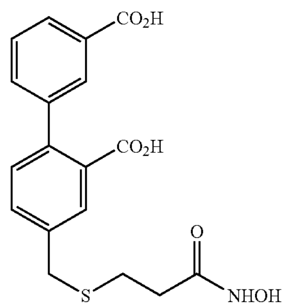 | 4-(2-Hydroxycarbamoyl-ethylsulfanylmethyl)-biphenyl-2,3'-dicarboxylic acid |
| 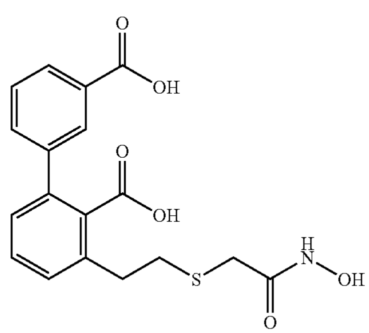 | 3-(2-Hydroxycarbamoyl-methylsulfanylethyl)-biphenyl-2,3'-dicarboxylic acid |
| | |

TABLE I-continued

| Structure | Name |
|---|---|
| 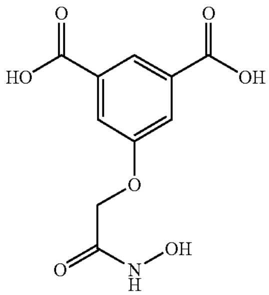 | 5-Hydroxycarbamoyl-methoxy-isophthalic acid |
| 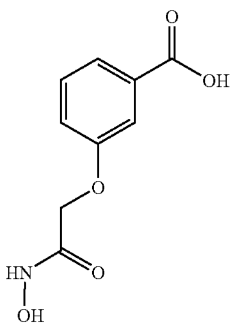 | 3-Hydroxycarbamoyl-methoxy-benzoic acid |
| | |
| | |

TABLE I-continued

| Structure | Name |
|---|---|
| | 3-(4-Hydroxycarbamoyl-butoxy)-biphenyl-2,3'-dicarboxylic acid |
| | 3-(4-Hydroxycarbamoyl-butoxy)-biphenyl-2,3'-dicarboxylic acid |
| 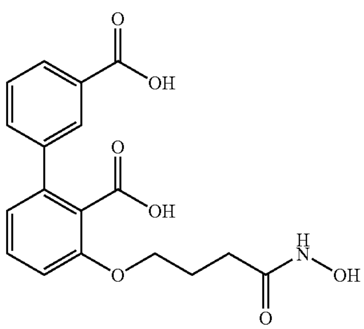 | 3-(3-Hydroxycarbamoyl-propoxy)-biphenyl-2,3'-dicarboxylic acid |
| 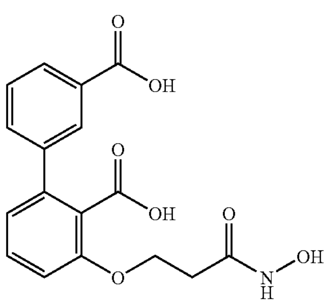 | 3-(2-Hydroxycarbamoyl-ethoxy)-biphenyl-2,3'-dicarboxylic acid |
| 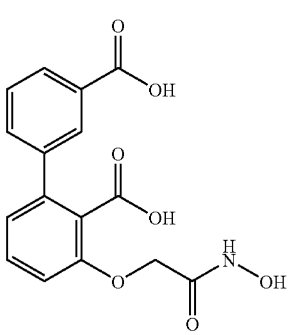 | 3-Hydroxycarbamoyl-methoxy-biphenyl-2,3'-dicarboxylic acid |

TABLE I-continued

| Structure | Name |
|---|---|
| 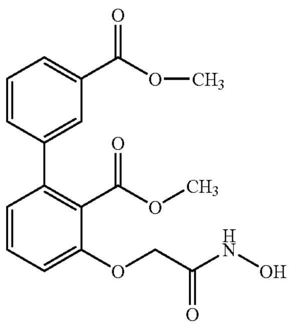 | 3-Hydroxycarbamoyl-methoxy-biphenyl-2,3'-dicarboxylic acid dimethyl ester |
| 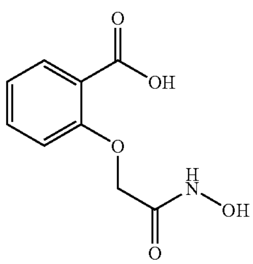 | 2-Hydroxycarbamoyl-methoxy-benzoic acid |
| 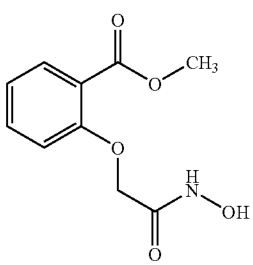 | 2-Hydroxycarbamoyl-methoxy-benzoic acid methyl ester |
| 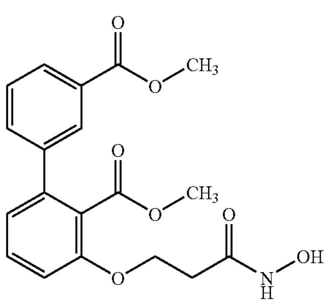 | 3-(2-Hydroxycarbamoyl-ethoxy)-biphenyl-2,3'-dicarboxylic acid dimethyl ester |
| | |

TABLE I-continued

| Structure | Name |
|---|---|
| 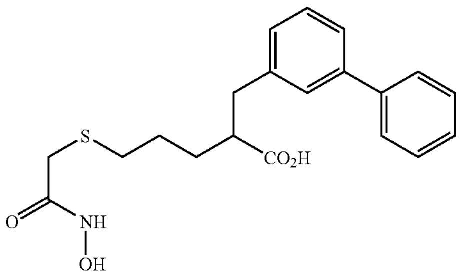 | 2-Biphenyl-3-ylmethyl-5-hydroxycarbamoylmethylsulfanyl-pentanoic acid |
| 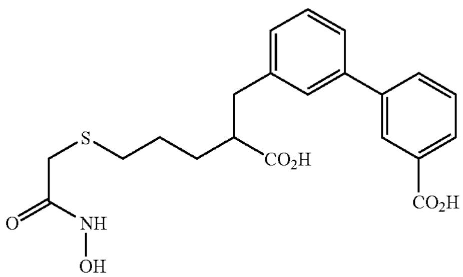 | 3'-(2-Carboxy-5-hydroxycarbamoylmethylsulfanyl-pentyl)-biphenyl-3-carboxylic acid |
| 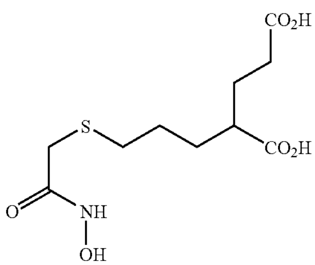 | 2-(3-Hydroxycarbamoyl-methylsulfanylpropyl)-pentanedioic acid |
| 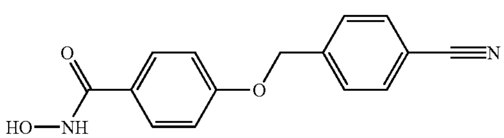 | 4-(4-Cyano-benzyloxy)-N-hydroxy-benzamide |
| 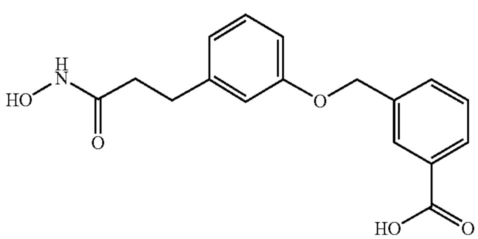 | 3-[3-(2-Hydroxycarbamoyl-ethyl)-phenoxymethyl]-benzoic acid |
| | |

TABLE I-continued

| Structure | Name |
|---|---|
| 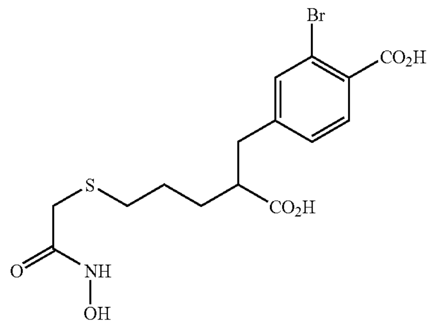 | 2-Bromo-4-(2-carboxy-5-hydroxycarbamoylmethyl-sulfanylpentyl)-benzoic acid |
| 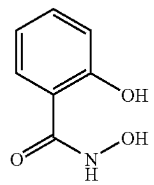 | 2,N-Dihydroxy-benzamide |
| 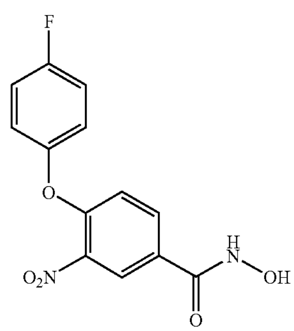 | 4-(4-Fluoro-phenoxy)-N-hydroxy-3-nitro-benzamide |
| 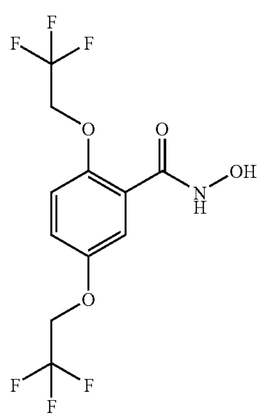 | N-Hydroxy-2,5-bis-(2,2,2-trifluoro-ethoxy)-benzamide |
| 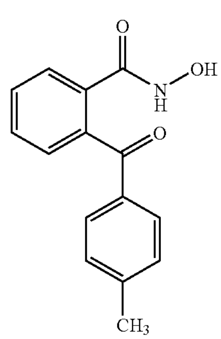 | N-Hydroxy-2-(4-methyl-benzoyl)-benzamide |

TABLE I-continued

| Structure | Name |
|---|---|

[Structure: 2-(hydroxycarbamoyl)phenyl ketone linked to terephthalamide with N-hydroxy amide]

Other NAALADase Inhibitors

Other NAALADase inhibitors are described in International Publication No. WO 01/14390 and copending U.S. Patent Application Ser. No. 09/438,970 filed Nov. 12, 1999 (corresponding to International Patent Application No. PCT/US00/30977 filed Nov. 13, 2000), the entire contents of which publication and applications are herein incorporated by reference as though set forth herein in full.

Possible substituents of the compounds of formulas I-XV include, without limitation, $C_1$-$C_6$ alkyl, $C_2$-$C_6$ alkenyl, $C_2$-$C_6$ alkynyl, $C_1$-$C_6$ alkoxy, $C_2$-$C_6$ alkenyloxy, phenoxy, benzyloxy, hydroxy, carboxy, hydroperoxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, nitro, nitroso, isonitroso, nitrosamino, imino, nitrosimino, oxo, $C_1$-$C_6$ alkylthio, sulfamino, sulfamoyl, sulfeno, sulfhydryl, sulfinyl, sulfo, sulfonyl, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene and carbocyclic and heterocyclic moieties.

Carbocyclic moieties include alicyclic and aromatic structures. Examples of carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

All variables of formulas I-XV are independently selected at each occurrence. For example, formula II may have two different $CR^{10}R^{11}$ moieties when X is a moiety of formula III and n is 2, with the first $CR^{10}R^{11}$ moiety being $CH_2$, and the second $CR^{10}R^{11}$ moiety being $CH(CH_3)$.

The compounds of formulas I-XV may possess one or more asymmetric carbon center(s) and, thus, may be capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base, and then separation of the mixture of diastereoisomers by crystallization followed by liberation of the optically active bases from these salts. Examples of optically active acids are tartaric, diacetyltartaric, dibenzoyltartaric, ditoluoyltartaric and camphorsulfonic acid. A different process for separation of optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds can likewise be obtained by utilizing optically active starting materials.

It is understood that the compounds of formulas I-XV encompass optical isomers as well as racemic and non-racemic mixtures.

Synthesis of NAALADase Inhibitors

Some of the NAALADase inhibitors used in the inventive methods and pharmaceutical compositions can be readily prepared by standard techniques of organic chemistry, utilizing the general synthetic pathways and examples depicted in U.S. Pat. Nos. 5,672,592, 5,795,877, 5,863,536, 5,880,112, 5,902,817, 5,962,521, 5,968,915, 6,025,344, 6,025,345, 6,028,216, 6,046,180, 6,054,444, 6,071,965 and 6,121,252, allowed U.S. patent application Ser. No. 09/228,391 for which the issue fee has been paid, copending U.S. patent application Ser. No. 09/438,970 filed Nov. 12, 1999 (corresponding to International Patent Application No. PCT/US00/30977 filed Nov. 13, 2000), and International Publications Nos. WO 99/33849, WO 00/01668 and WO 01/14390, the entire contents of which patents, patent application and publications are herein incorporated by reference, as though set forth herein in full.

Other NAALADase inhibitors may be available from commercial suppliers or can be readily prepared by an ordinarily skilled artisan using standard techniques such as those disclosed in U.S. Pat. No. 5,859,046, the entire contents of which reference are herein incorporated by reference as though set forth herein in full.

Yet other NAALADase inhibitors can be readily prepared by standard techniques of organic chemistry, utilizing the general synthetic pathways depicted below in SCHEMES I-XVI.

SCHEME I

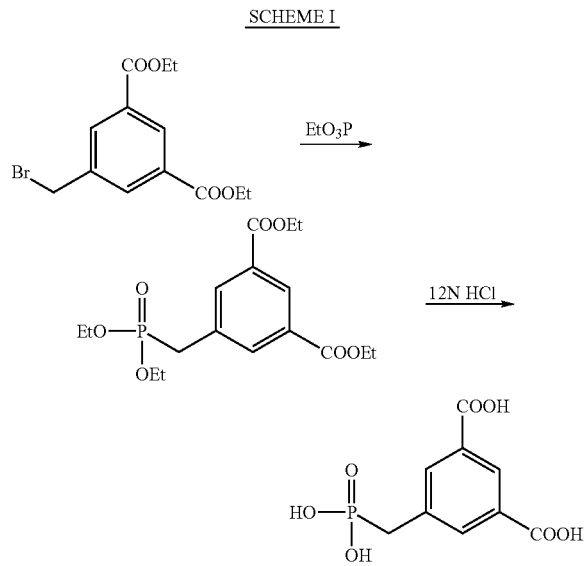

SCHEME II

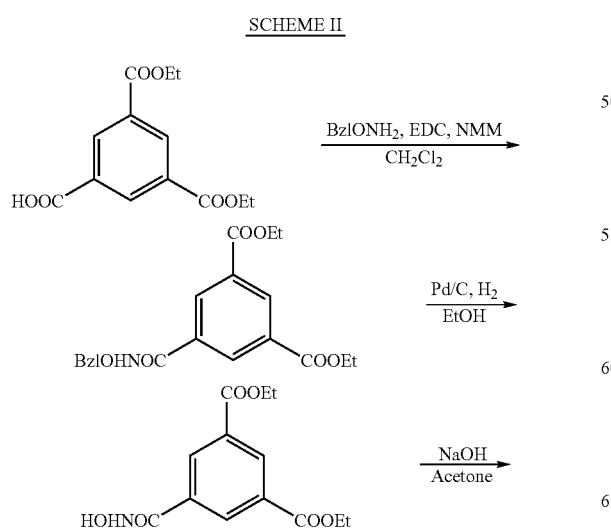

-continued

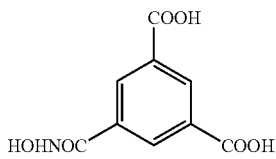

SCHEME III

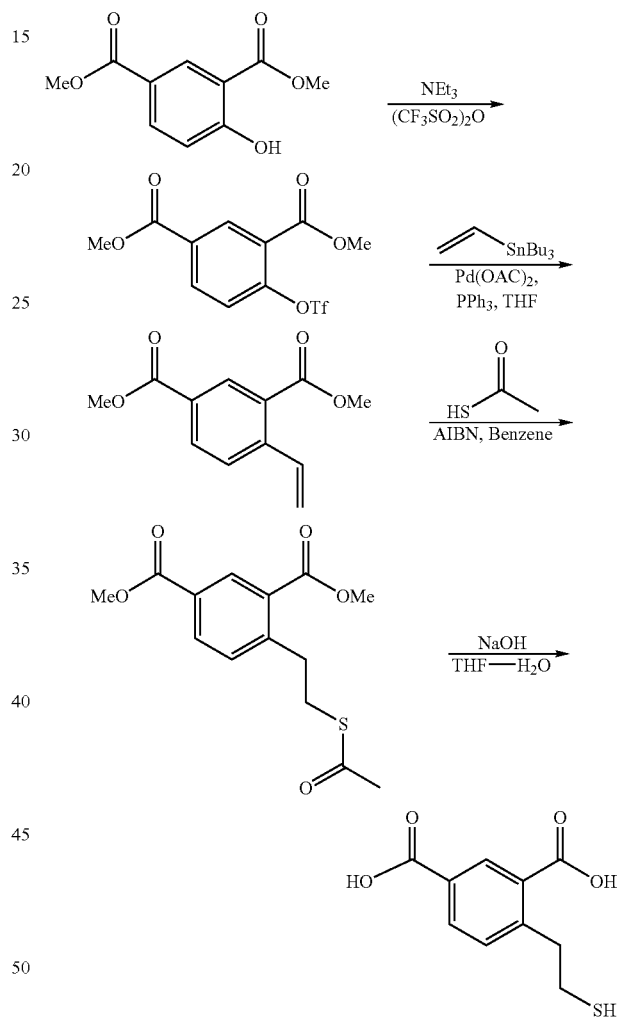

SCHEME IV

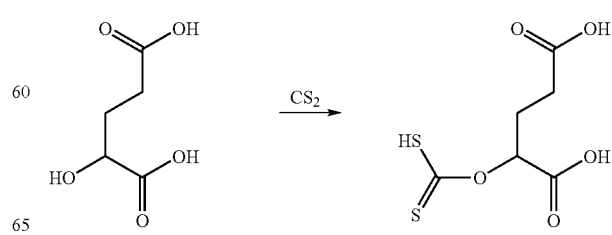

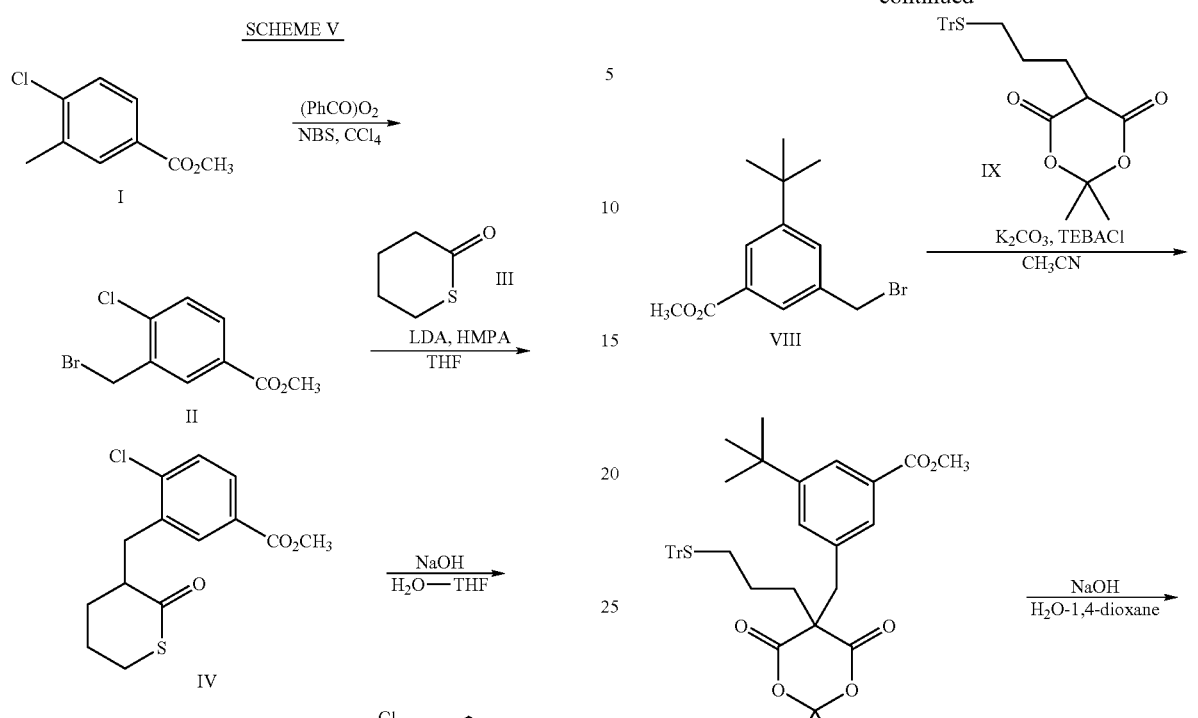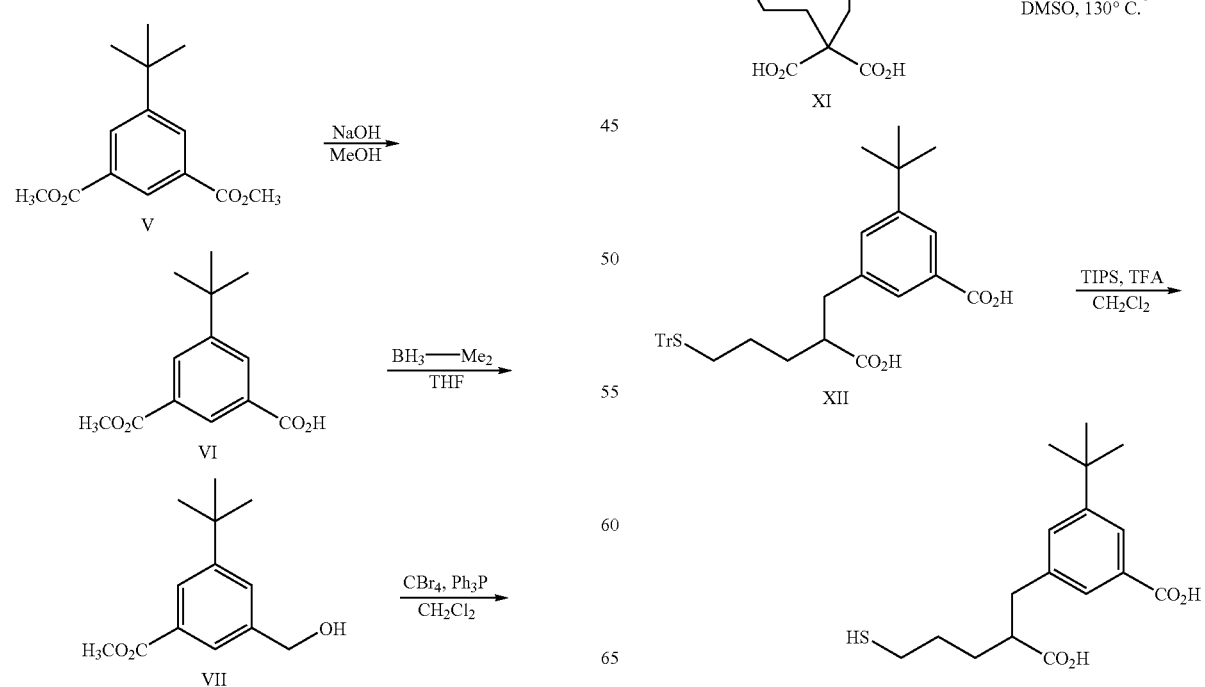

SCHEME VII
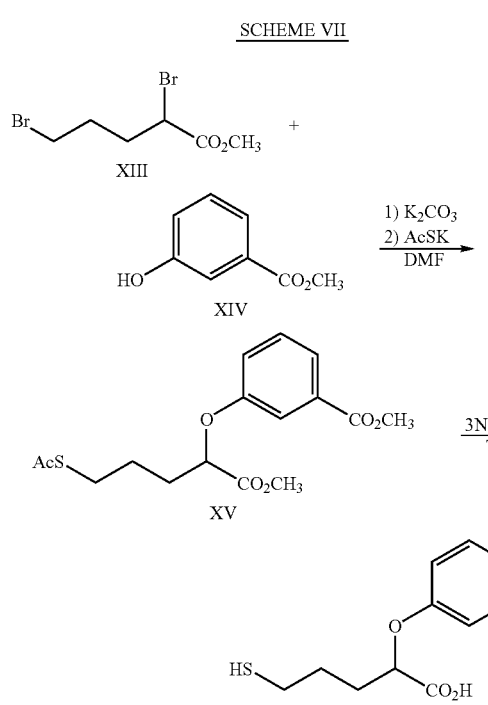
SCHEME VIII
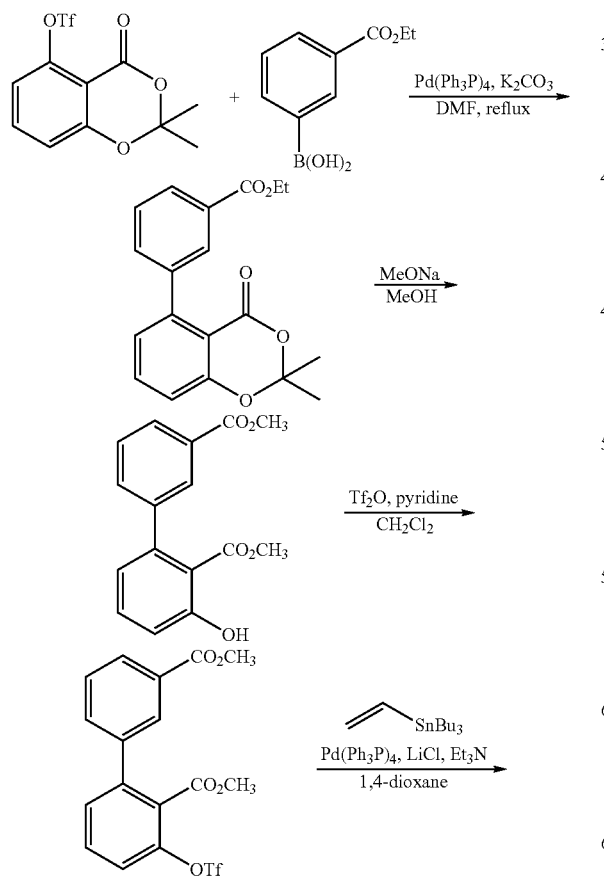
SCHEME IX
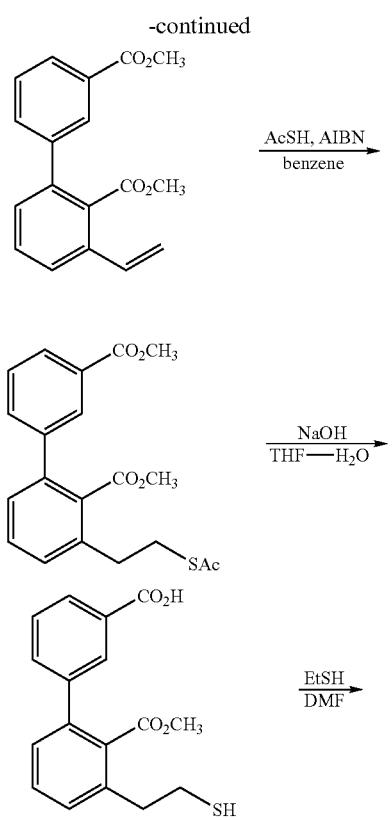

-continued
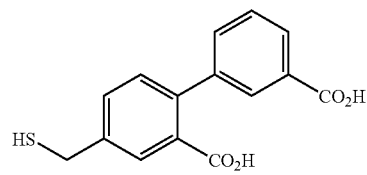
SCHEME X
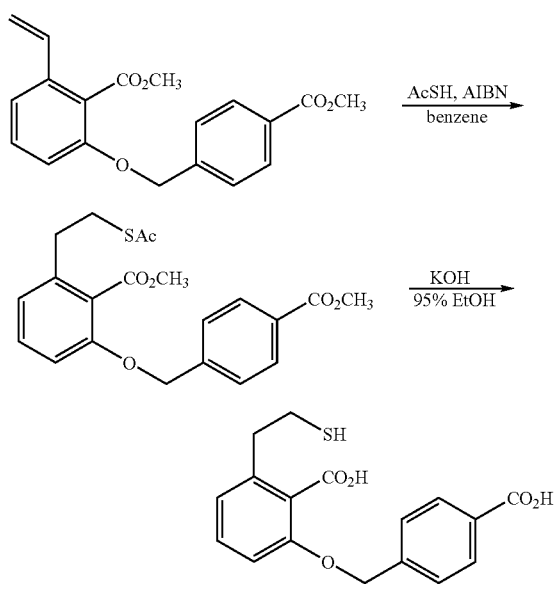
SCHEME XI
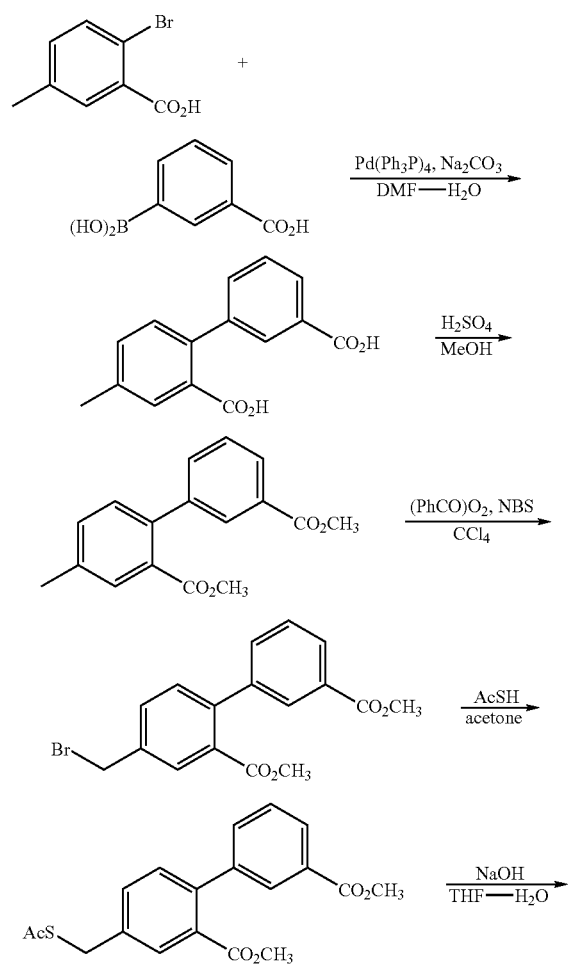
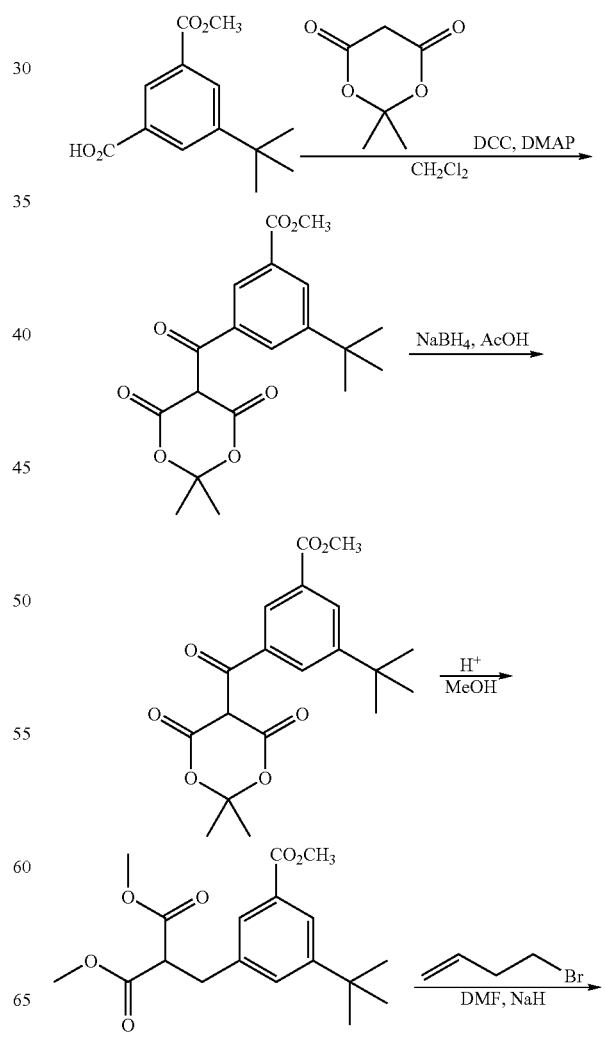

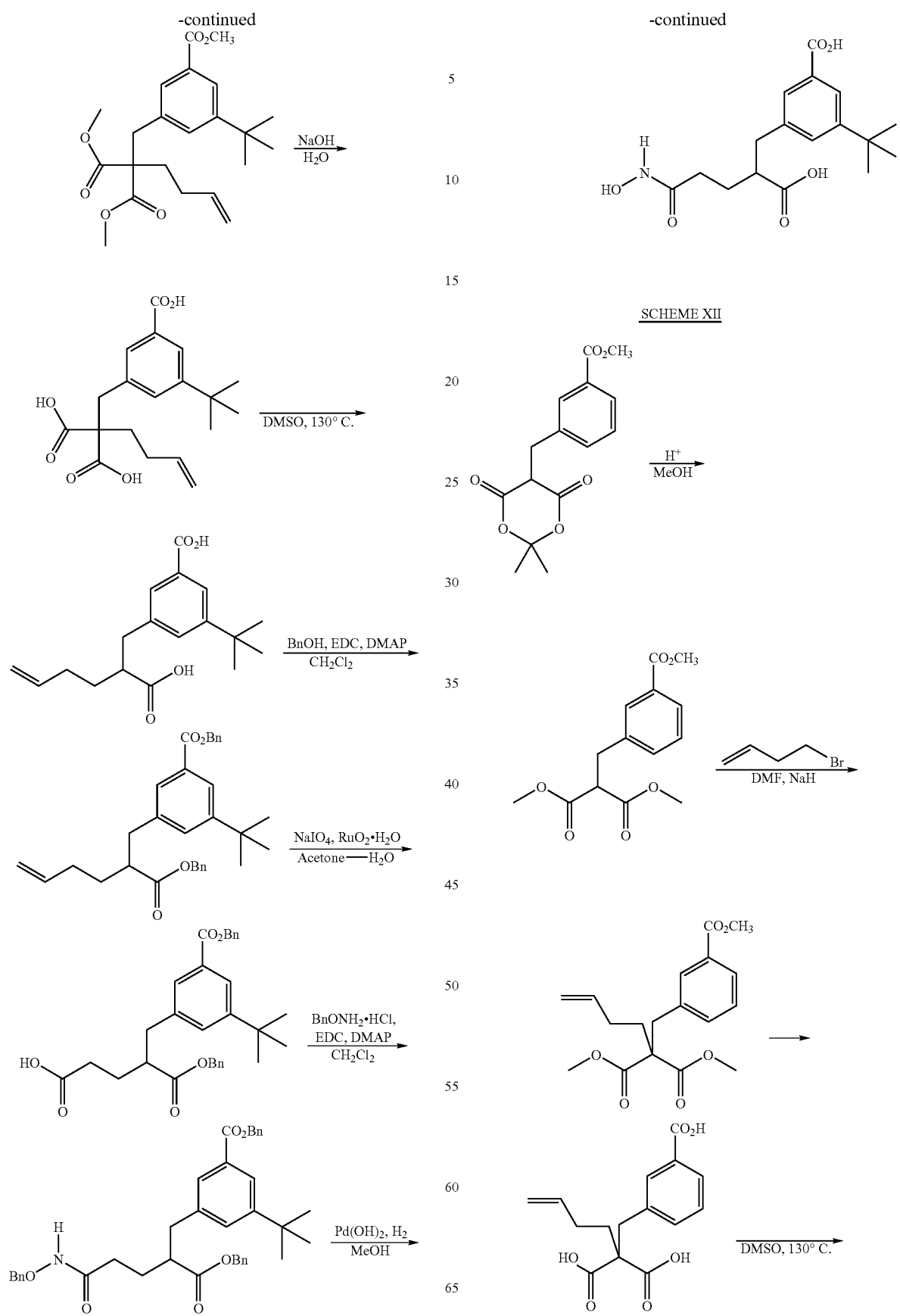

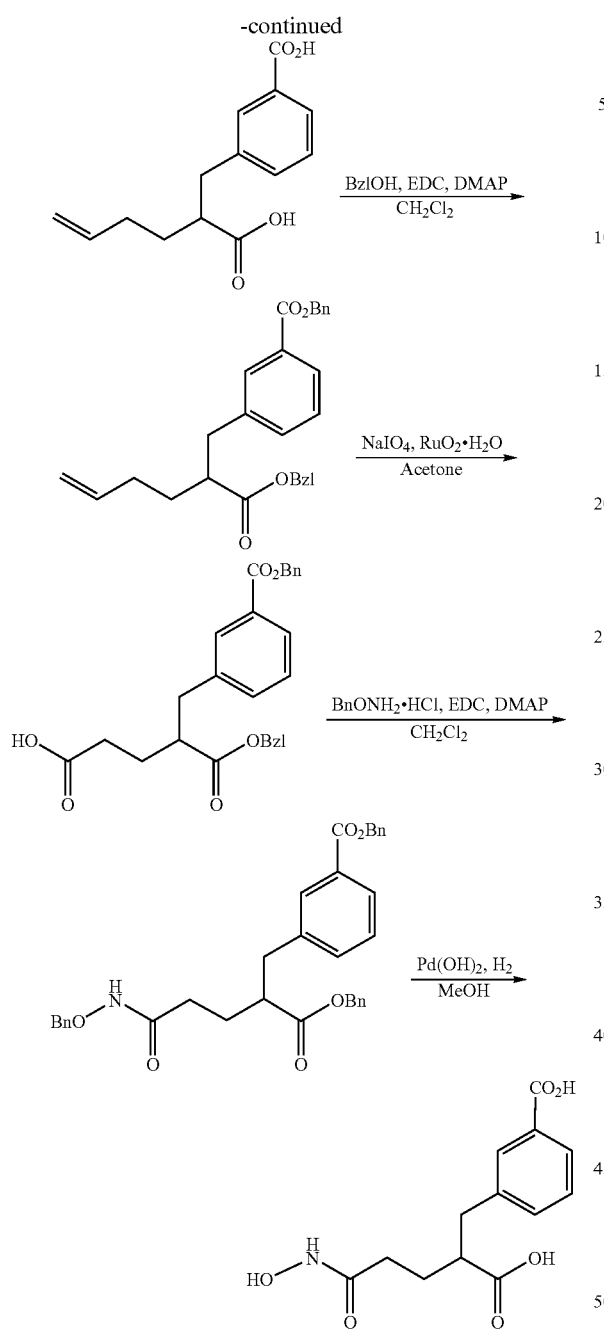
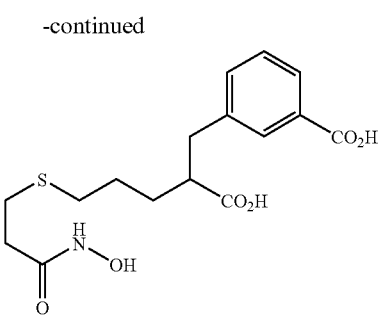
SCHEME XIV
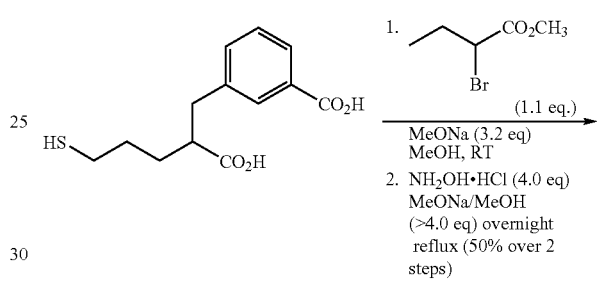
SCHEME XIII
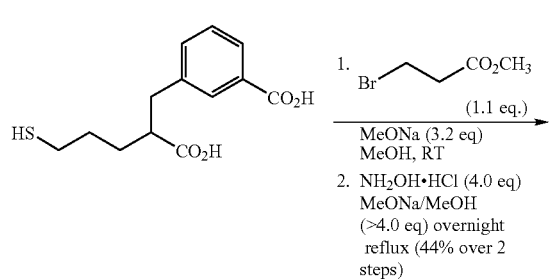
SCHEME XV
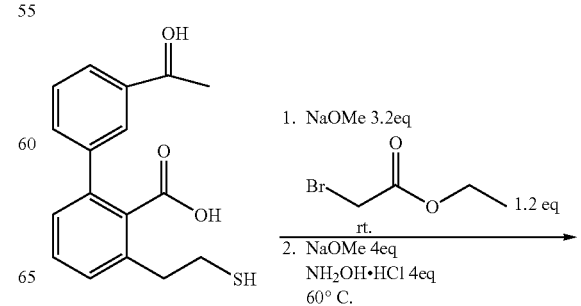

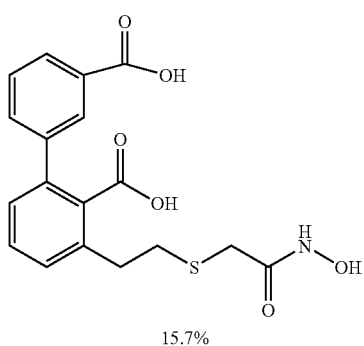
15.7%
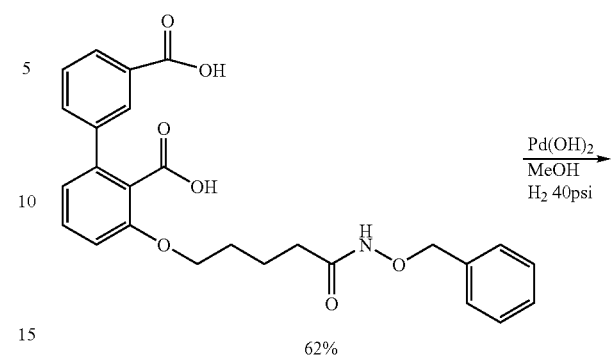
62%
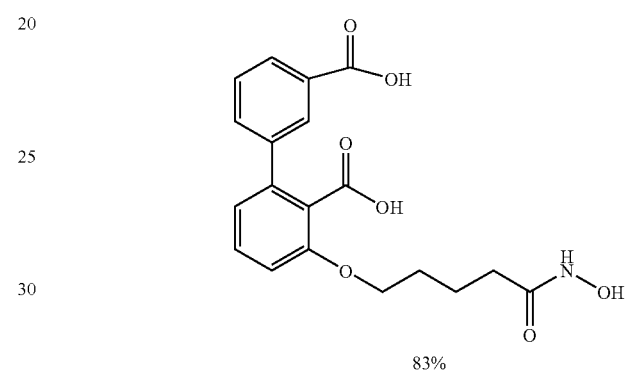
83%
Precursor compounds may be commercially available, prepared by methods known to a person of skill in the art, or prepared by SCHEMES XVII and XVIII.
SCHEME XVI
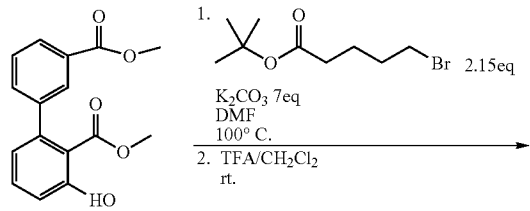
SCHEME XVII
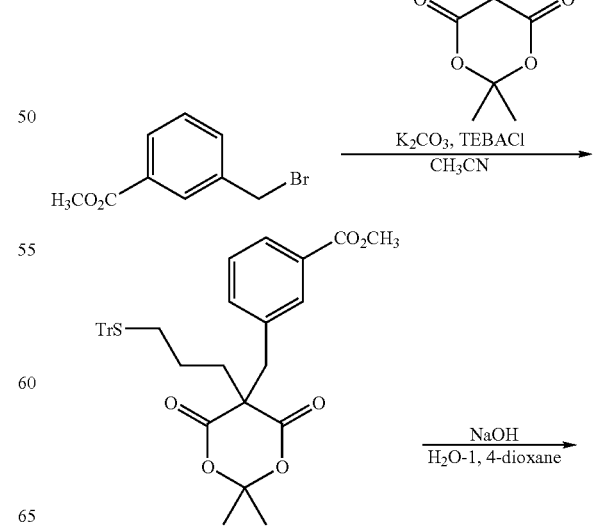
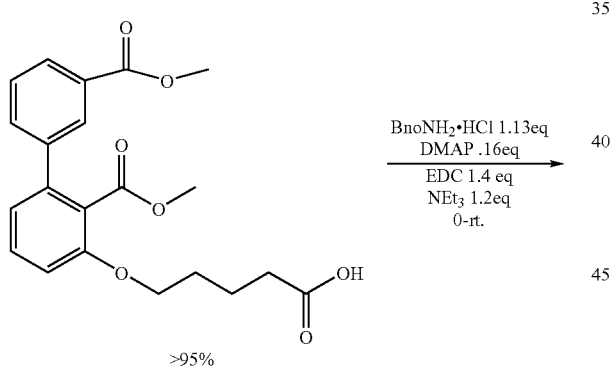
>95%
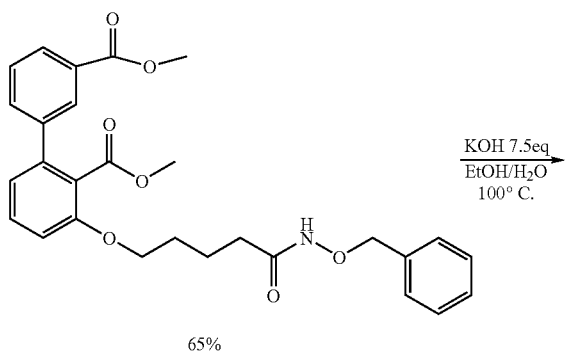
65%

-continued

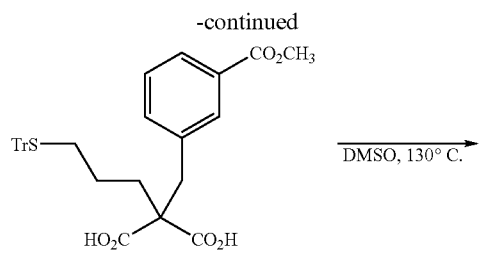

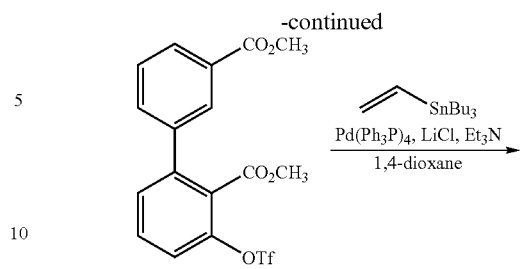

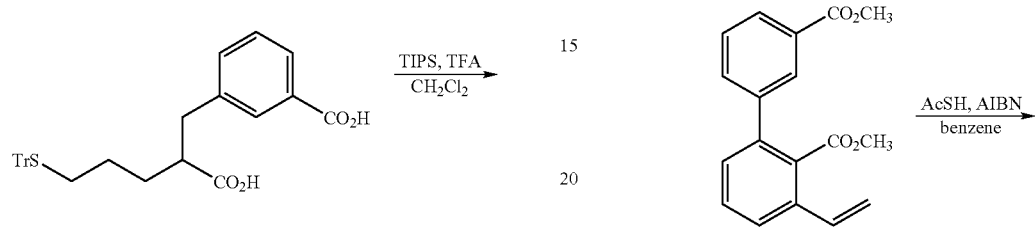

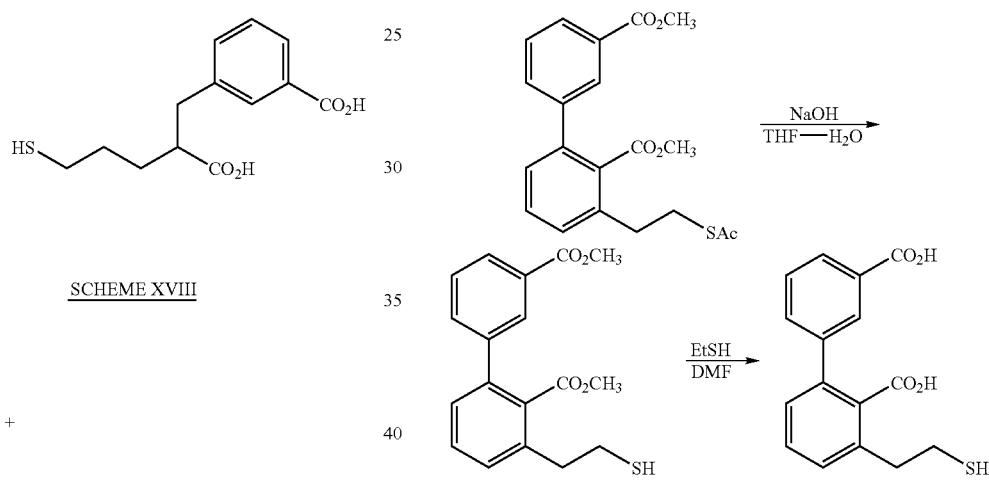

SCHEME XVIII

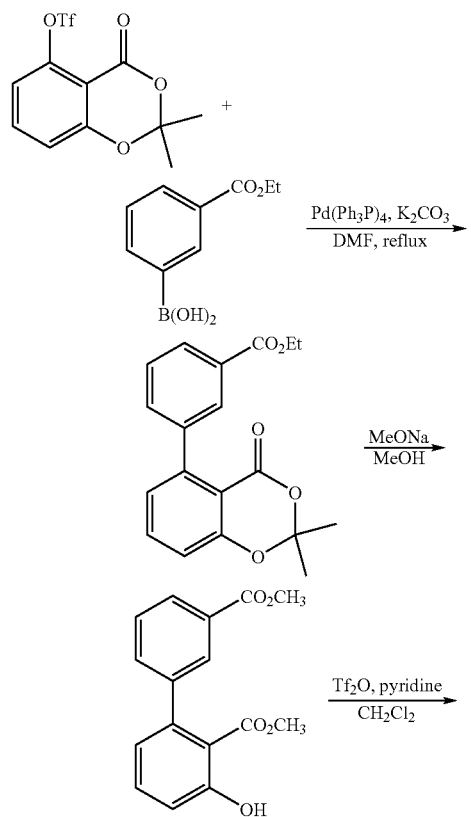

Route of Administration

In the inventive methods, the compounds will generally be administered to a patient in the form of a pharmaceutical formulation. Such formulation preferably includes, in addition to the active agent, a physiologically acceptable carrier and/or diluent. The compounds may be administered locally or systemically by any means known to an ordinarily skilled artisan. For example, the compounds may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. Topical administration includes, without limitation, administration via eyedrops. The exact administration protocol will vary depending upon various factors including the age, body weight, general health, sex and diet of the patient; the determination of specific administration procedures would be routine to an ordinarily skilled artisan. The compounds and compositions used in the inventive methods may be capable of crossing the blood-brain barrier.

Dosage

In the inventive methods, the compounds and compositions may be administered by a single dose, multiple discrete doses or continuous infusion. Pump means, particularly subcutaneous pump means, are preferred for continuous infusion.

Dose levels on the order of about 0.001 to about 10,000 mg/kg of the active ingredient compound are useful in the inventive methods, with preferred levels being about 0.1 to about 1,000 mg/kg, and more preferred levels being about 1 to 100 mg/kg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Administration Regimen

For the inventive methods, any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-administration With Other Treatments

In the inventive methods, the NAALADase inhibitors and pharmaceutical compositions may be used alone or in combination with one or more additional agent(s) for simultaneous, separate or sequential use.

The additional agent(s) may be any therapeutic agent(s) known to an ordinarily skilled artisan, including, without limitation, (an)other compound(s) of formulas I-XV.

The NAALADase inhibitors and pharmaceutical compositions may be co-administered with one or more therapeutic agent(s) either (i) together in a single formulation, or (ii) separately in individual formulations designed for optimal release rates of their respective active agent. Each formulation may contain from about 0.01% to about 99.99% by weight of a NAALADase inhibitor, as well as one or more pharmaceutically acceptable carrier(s), such as wetting, emulsifying and/or pH buffering agent(s).

In addition, the NAALADase inhibitors and pharmaceutical compositions may be administered prior to, during or following surgery or physical therapy.

EXAMPLES

The following examples are illustrative of the present invention and are not intended to be limitations thereon. Unless otherwise indicated, all percentages are based upon 100% by weight of the final composition.

Example 1

Preparation of 5-phosphonomethyl-1,3-benzenedicarboxylic acid (SCHEME I)

Diethyl 5-[(diethoxyphosphinyl)methyl]-1,3-benzenedicarboxylate

A solution of 5-bromomethyl-1,3-benzene-dicarboxylate (Collman et al., *J. Am. Chem. Soc.*, 116(14) (1994) 6245-6251; 0.315 g, 1.0 mmol) in triethylphosphite (3.0 ML) was heated at 150° C. for 5 hours. The solvent was removed under reduced pressure and the residual oil was purified by chromatography to give 0.248 g of colorless oil: $^1$H NMR (CDCl$_3$) δ 1.28 (t, 3H), 1.42 (t, 3H), 3.26 (d, 2H)$_1$ 4.06 (q, 2H) 4.41 (q, 2H), 8.17 (s, 2H), 8.58 (s, 1H). TLC: R$_f$ 0.10 (EtOAc/Hexanes 1/1).

5-Phosphonomethyl-1,3-benzenedicarboxylic acid

A solution of diethyl 5-[(diethoxyphosphinyl) methyl]-1,3-benzenedicarboxylate (0.186 g, 0.5 mmol) in 12 N HCl (2.5 mL) was heated at 100° C. for 24 hours. The resulting precipitate was washed with water and dried under vacuum to give 0.057 g of white powder: $^1$H NMR (D$_2$O) δ 3.11 (d, 2H), 7.93 (s, 2H), 8.19 (s, 1H). TLC: R$_f$ 0.20 (EtOAc/Hexanes 1/1). Elemental analysis calculated for $C_9H_7O_7P \cdot H_2O$: C, 38.86; H, 3.99. Found: C, 38.74; H, 4.08.

Example 2

Preparation of 5-[(hydroxyamino)carbonyl]-1,3-benzene-dicarboxylic acid (SCHEME II)

Diethyl 5-[[(phenylmethoxy)amino]carbonyl]-1,3-benzenedicarboxylate

To a solution of diethyl 1,3,5-benzenetricarboxylate (3.192 g, 20 mol) and O-benzylhydroxyamine hydrochloride (4.789 g, 19 mmol) in 40 mL were added N-methylmorpholine (2.2 mL, 20 mmol) and EDC (3.834 g, 20 mmol) at 0° C., and the mixture was stirred at room temperature for 20 hours. The solvent was removed by evaporator and the residue was dissolved in EtOAc (150 mL). The organic solution was washed with 1 N HCL (150 mL), washed with saturated aqueous NaHCO$_3$ (50 mL), dried over Na$_2$SO$_4$, and concentrated to give white solid. This material was recrystallized from EtOAc to give 4.154 g of white powder: $^1$H NMR (CDCl$_3$) δ 1.41 (t, 6H), 4.40 (q, 4H), 5.05 (s, 2H), 7.3-7.5 (m, 5H), 8.52 (s, 2H), 8.76 (s, 1H), 9.1 (br, 1H). TLC: R$_f$ 0.62 (EtOAc/Hexanes 1/1).

Diethyl 5-[(hydroxyamino)carbonyl]-1,3-benzenedicarboxylate

To a solution of diethyl 5-[[(phenylmethoxy)amino]carbonyl]-1,3-benzenedicarboxylate (0.742 g, 2.0 mmol) in ethanol (10 mL) was added a suspension of Pd/C in ethanol (5 mL), and the mixture was shaken under hydrogen (50 psi) for 20 hours. The catalyst was removed by filtration through a pad of celite and the filtrate was concentrated to give white powder. This material was washed with ethanol (10 mL×2) and dried under vacuum to give 0.380 g of white powder: $^1$H NMR (CD$_3$OD) δ 1.44 (t, 6H), 4.45 (q, 4H), 8.60 (s, 2H), 8.72 (s, 1H). TLC: R$_f$ 0.20 (EtOAc/Hexanes 1/1).

5-[(Hydroxyamino)carbonyl]-1,3-benzene-dicarboxylic acid

To a solution of diethyl 5-[(hydroxyamino)carbonyl]-1,3-benzenedicarboxylate (0.281 g, 1.0 mmol) in acetone (5 mL) was added 1.0 N NaOH (5 mL) at room temperature, and the mixture was stirred at room temperature for 2 hours. The solvent was removed under reduced pressure and the residue was taken up with 1 N HCl (15 mL) to give white precipitate. This material was dried under vacuum to give 0.096 g of white solid: $^1$H NMR (D$_2$O) δ 8.52 (s, 2H), 8.76 (s, 1H). Elemental analysis calculated for CH$_7$NO$_6$.H$_2$O: C, 44.45; H, 3.73; N, 5.76. Found: C, 44.47; H, 3.78; N, 5.74.

Example 3

Preparation of 4-(2-mercaptoethyl)-1,3-benzenedicarboxylic acid (SCHEME III)

Dimethyl 4-trifluoromethanesulfonyloxy-1,3-benzenedicarboxylate

To a solution of dimethyl 4-hydroxy-isophthalate (0.850 g, 4.04 mmol) in CH$_2$Cl$_2$ (15 mL) were added triethylamine (0.6 mL, 4.3 mmol) and triflic anhydride (0.8 mL, 4.76 mmol) at 0° C., and the mixture was stirred at 0° C. for 18 hours. The solvent was evaporated and the residue was diluted with ether (30 mL). The organic solution was washed with 1 N HCl (30 mL×3), dried over MgSO$_4$, and concentrated to give 1.30 g of dark yellow oil (93% yield): $^1$H NMR (CDCl$_3$) δ 3.97 (s, 3H), 4.00 (s, 3H) 7.4 (d, 1H), 8.3 (d, 1H), 8.74 (s, 1H)

Dimethyl 4-ethenyl-1,3-benzenedicarboxylate

To a solution of dimethyl 4-trifluoromethanesulfonyloxy-1,3-benzenedicarboxylate (1.5 g, 4.38 mmol) in dioxane (50 mL) were added Pd(PPh$_3$)$_4$ (510 mg, 0.44 mmol), lithium chloride (1.3 g, 30.7 mmol) and tributyl(vinyl)tin (1.5 mL, 5.13 mmol) at room temperature. The mixture was heated at 100° C. for 5 hours. The reaction mixture was filtered and the filtrate was concentrated and passed through a column of silica gel (Hexanes/EtOAc=10:1) to give 1.1 g of colorless oil (84% yield): $^1$H NMR: (CDCL$_3$) δ 3.92 (s, 3H), 3.93 (s, 3H), 5.45 (d, 1H), 5.73 (d, 1H) 7.49 (m, 1H), 7.66 (d, 1H), 8.13 (d, 1H), 8.53 (s, 1H).

Dimethyl 4-[2-(acetylthio)ethyl]-1,3-benzenedicarboxylate

To a degassed solution of dimethyl 4-ethenyl-1,3-benzenedicarboxylate (415 mg, 1.88 mmol) in benzene (6 mL) were added AIBN (33 mg, 0.21 mmol) and thioacetic acid (0.27 mL, 3.78 mmol), and the mixture was refluxed for 5 hours. The reaction mixture was diluted with aqueous NaHCO$_3$ solution (15 mL) and extracted with EtOAc (15 mL) The organic layer was dried over MgSO$_4$ and concentrated. The residual material was purified by silica gel chromatography (hexanes/EtOAc=10:1) to give 0.150 9 of colorless oil (27% yield): $^1$H NMR (CDCl$_3$) δ 2.32 (s, 3H), 3.16 (t, 2H), 3.28 (t, 2H), 3.94 (s, 6H), 7.42 (d, 1H), 8.09 (d, 1H), 8.58 (s, 1H).

4-(2-Mercaptoethyl)-1,3-benzenedicarboxylic acid

To a degassed solution of dimethyl 4-[2-(acetylthio)ethyl]-1,3-benzenedicarboxylate (0.130 g, 0.44 mmol) in THF (5 mL) was added a degassed solution of 5 N NaOH (5 mL). The reaction mixture was stirred under nitrogen overnight. The reaction mixture was diluted with H$_2$O (10 mL) and extracted with EtOAC (10 mL). The organic layer was dried over MgSO$_4$ and concentrated to give 0.045 g of white solid (45% yield): $^1$H NMR (DMSO) δ 2.67 (t, 2H) 3.21 (t, 2H), 7.37 (d, 1H), 7.98 (d, 1H), 8.46 (s, 1H). $^{13}$C NMR (DMSO) δ 26.64, 40.60, 130.87, 132.05, 133.46, 133.81, 134.13, 148.53, 169.22, 170.20. Elemental analysis calculated for C$_{10}$H$_{10}$SO$_4$: C, 53.09; H, 4.45; S, 14.47. Found: C, 53.37; H, 4.87; S, 12.84. MS(FAB): 225.

Example 4

Preparation of 5-carboxy-2-chloro-alpha-(3-mercaptopropyl)-benzenepropanoic acid (Scheme V)

Methyl 3-bromomethyl-4-chlorobenzoate II

To a suspension of methyl 4-chloro-3-methylbenzoate I (19.9 g, 108 mmol) and N-bromosuccinimide (NBS, 20.2 g, 114 mmol) in carbon tetrachloride (500 mL) was added benzoyl peroxide (1.30 g, 5.4 mmol), and the mixture was stirred at 90° C. overnight. The mixture was then cooled and the white precipitate was removed by filtration. The filtrate was concentrated and the resulting solid was re-crystallized from ethyl acetate to give methyl 3-bromomethy-4-chlorobenzoate II (15.0 g, 57 mmol, 53%) as a white solid: $^1$H NMR (CDCl$_3$) δ 3.95 (s, 3H), 4.63 (s, 2H) 7.49 (d, J=8.3 Hz, 1H), 7.94 (dd, J=2.1, 8.3 Hz, 1H), 8.15 (d, J=2.1 Hz, 1H)

3-(2-Chloro-5-methoxycarbonylbenzyl)-tetrahydrothiopyrane-2-one IV

To a solution of lithium diisopropylamide (2.0 M solution, 3.3 mL, 6.6 mmol) in THF (25 mL) was added tetrahydrothiopyran-2-one III (0.731 g, 6.3 mmol) at −40° C., and the mixture was stirred at −40° C. for 45 minutes. A solution of methyl 3-bromomethy-4-chlorobenzoate II (1.67 g, 6.3 mmol) in THF (10 mL) was then dropwise added to the mixture at −40° C. Subsequently, hexamethylphosphoramide (0.20 g, 1.4 mmol) was added to the mixture at −40° C., and the reaction mixture was stirred at −40° C. for 4 hours. A saturated ammonium chloride solution (30 mL) was added to the reaction mixture, and the organic solvent was removed under reduced pressure. The mixture was then partitioned between ether (150 mL) and H$_2$O (150 mL). The organic layer was washed with brine, dried over MgSO$_4$, and concentrated. The crude material was chromatographed on silica gel using EtOAc/hexanes to afford 3-(2-chloro-5-methoxycarbonylbenzyl)-tetrahydrothio-pyrane-2-one IV (0.60 g, 2.0 mmol, 32%) as a white solid: $^1$H NMR (CDCl$_3$) δ 1.65-1.75 (m, 1H), 1.90-2.05 (m, 2H), 2.05-2.15 (m, 2H), 2.74 (dd, J=9.4, 13.9 Hz, 1H), 2.85-3.00 (m, 1H), 3.10-3.20 (m, 2H), 3.58 (dd, J=4.7, 13.9 Hz, 1H), 3.92 (s, 3H), 7.44 (d, J=8.3 Hz, 1H), 7.85 (dd, J=8.3, 2.1 Hz, 1H), 7.91 (d, J=2.1 Hz, 1H)

5-Carboxy-2-chloro-alpha-(3-mercaptopropyl) benzenepropanoic acid

A solution of 3-(2-Chloro-5-methoxycarbonyl-benzyl)tetrahydrothiopyrane-2-one IV (9.26 g, 31.0 mmol) in THF (70 mL) was purged for 15 minutes with nitrogen. A degassed aqueous sodium hydroxide solution (2.2 M, 70 mL, 154 mmol) was added to the solution and the mixture was stirred at room temperature under nitrogen overnight. The reaction mixture was washed with ether, acidified by 3N HCl at 0° C., and extracted with ether. The extract was dried over MgSO$_4$ and concentrated to afford 5-carboxy-2-chloro-alpha-(3-mercaptopropyl) benzenepropanoic acid (8.42 g, 27.8 mmol, 90%) as a white solid: $^1$H NMR (CD$_3$OD) δ 1.50-1.80 (m, 4H), 2.35-2.50 (m, 2H), 2.65-2.75 (m, 1H), 2.91 (dd, J=6.2, 13.8 Hz, 1H), 2.96 (dd, J=8.8, 13.8 Hz, 1 H), 7.39 (d, J=8.3 Hz, 1H), 7.76 (dd, J=2.0, 8.3 Hz, 1H), 7.86 (d, J=2.0 Hz, 1H); $^{13}$C NMR (CD$_3$OD) δ25.1, 32.5, 33.2, 37.4, 46.8, 130.8, 131.2, 134.0, 139.1, 140.5, 169.2, 178.9. Elemental analysis calculated for C$_{13}$H$_{15}$ClO$_4$S: C, 51.57; H, 4.99; S, 10.59; Cl, 11.71. Found: C, 51.59; H, 4.94; S, 10.43; Cl, 11.80.

Example 5

Preparation of 3-carboxy-5-(1,1-dimethylethyl)-alpha-(3-mercaptopropyl)-benzenepropanoic acid (Scheme VI)

Methyl 5-tert-butylhydrogenisophthalate VI

To a solution of dimethyl 5-tert-butylisophthalate V (23.0 9, 92 mmol) in methanol (150 mL) was added a solution of sodium hydroxide (3.68 g, 92 mmol) in H$_2$O (10 mL) at 25° C., and the mixture was stirred at 25° C. for 3 hours. The organic solvent was removed under reduced pressure and the residual solid was suspended in an aqueous sulfuric acid solution (1.0 M). The suspension was filtered and the precipitate was washed with H$_2$O, dried under vacuum, and crystallized from hexanes/ethyl acetate to afford methyl 5-tert-butylhydrogenisophthalate VI (16.3 g, 69.0 mmol, 75%) as a white solid: $^1$H NMR (CDCl$_3$) δ1.45 (s, 9H), 3.9 (s, 3H), 8.5 (s, 1H), 8.7 (s, 1H), 8.8 (s, 1H); $^{13}$C NMR (CDCl$_3$) δ31.3 (3C), 35.2, 52.5, 128.8, 129.7, 130.7, 131.1, 131.6, 132.0, 166.7, 171.5.

Methyl 3-tert-butyl-5-hydroxymethylbenzoate VII

Borane-dimethyl sulfide complex (7.23 mL, 76.2 mmol) was slowly added to a solution of methyl 5-tert-butylhydrogenisophthalate VI (12.0 g, 50.8 mmol) in THF (100 ml) over the period of 20 minutes at room temperature. The mixture was stirred for 1.5 hours at room temperature and then refluxed for 1 additional hour. The reaction mixture was then cooled and the unreacted borane was decomposed with methanol (10 mL). The solvents were removed under reduced pressure and the residue was dissolved in ethyl acetate. The organic solution was washed with a saturated NaHCO$_3$ solution, dried over MgSO$_4$, and purified by a silica gel column chromatography (hexane/ethyl acetate) to afford methyl 3-tert-butyl-5-hydroxymethylbenzoate VII (10.0 g, 45.0 mmol, 90%) as a white solid: $^1$H NMR (CDCl$_3$) δ1.45 (s, 9H), 3.9 (s, 3H), 4.7 (s, 2H), 7.6 (s, 1H), 7.8 (s, 1H), 8.0 (s, 1H); $^{13}$C NMR (CDCl$_3$) δ31.4 (3C), 35.0, 52.3, 65.3, 125.5, 126.1, 128.8, 130.3, 141.0, 152.1, 167.5.

Methyl 3-bromomethyl-5-tert-butylbenzoate VIII

To a solution of methyl 3-tert-butyl-5-hydroxymethylbenzoate VII (9.50 g, 42.7 mmol) and carbon tetrabromide (17.25 g, 52.0 mmol) in dichloromethane (50 mL) was slowly added triphenylphosphine (13.6 g, 52.0 mmol) over the period of 20 minutes, and the mixture was stirred at room temperature for 25 minutes. The reaction mixture was concentrated under reduced pressure and the residue was suspended in ethyl acetate. The precipitate was removed by filtration and the filtrate was concentrated. The crude material was purified by a silica gel chromatography (hexanes/ethyl acetate, 4:1), and the product was re-crystallized form ethyl acetate/hexanes to afford methyl 3-bromomethyl-5-tert-butylbenzoate VIII (12.0 g, 42.1 mmol, 99%) as a white solid: $^1$H NMR (CDCl$_3$) δ 1.45 (s, 9H), 3.7 (s, 3H), 4.4 (s, 2H), 7.6 (s, 1H), 7.8 (s, 1H), 8.0 (s, 1H); $^{13}$C NMR (CDCl$_3$) δ 31.3 (3C), 33.2, 36.0, 52.3, 126.9, 127.5, 130.6, 130.7, 137.9, 152.4, 167.0.

5-(3-Tert-butyl-5-methoxycarbonyl-benzyl)-2,2-dimethyl-5-[3-[(triphenylmethyl)thio]propyl]-[1,3]dioxane-4,6-dione A solution of methyl 3-bromomethyl-5-tert-butylbenzoate (10.3 g, 36.1 mmol), 2,2-dimethyl-5-[3-[(triphenylmethyl)-thio]propyl]-[1,3]dioxane-4,6-dione IX (13.8 g, 30.0 mmol), and benzyltriethylammonium chloride (6.38 g, 30 mmol) in acetonitrile (90 mL) was added potassium carbonate (4.35 g, 30 mmol) at 25° C., and the reaction mixture was stirred at 60° C. overnight (the synthesis of compound IX was previously described in International Publication No. WO 00/01668). The solvent was removed under reduced pressure and the residue was partitioned between ethyl acetate and a 10% aqueous KHSO$_4$ solution. The organic layer was dried over MgSO$_4$, concentrated. The crude material was recrystallized from ethyl acetate/hexane mixture to afford 5-(3-tert-butyl-5-methoxycarbonyl-benzyl)-2,2-dimethyl-5-[3-[(triphenyl-methyl)thio]propyl]-[1,3]dioxane-4,6-dione X (14.0 g, 79%) as a white solid: $^1$H NMR (CDCl$_3$) δ0.7 (s, 3H), 1.3 (s, 9H), 1.2-1.3 (m, 2H), 1.5 (s, 3H), 2.0 (m, 2H), 2.2 (m, 2H), 3.3 (s, 2H), 3.8 (s, 3H), 7.2-7.4 (m, 16H), 7.6 (s, 1H), 7.8 (s, 1H); $^{13}$C NMR (CDCl$_3$) δ24.8, 29.1, 29.4, 31.2, 31.4, 34.9, 40.3, 43.7, 52.3, 57.3, 66.8, 105.8, 126.0, 126.8, 128.0, 128.5, 129.6, 130.5, 132.3, 135.3, 144.8, 152.4, 167.1, 168.5.

2-(3-tert-Butyl-5-methoxycarbonyl-benzyl)-2-[3-[(triphenylmethyl)thio]propyl]-malonic acid XI To a solution of 5-(3-tert-butyl-5-methoxycarbonylbenzyl)-2,2-dimethyl-5-[3-[(triphenylmethyl)thio]propyl]-[1,3]dioxane-4,6-dione x (11 g, 16.5 mmol) in 1,4-dioxane (15 ml) was added a solution of sodium hydroxide (4.63 g, 115.5 mmol) in H$_2$O (15 mL) at 25° C., and the mixture was stirred at 100° C. for 1 hour. The solvent was removed under reduced pressure and the residue was partitioned between ethyl acetate and a 10% aqueous KHSO$_4$ solution. The organic layer was dried over MgSO$_4$, concentrated. The crude material was recrystallized from ethyl acetate/hexane mixture to afford 2-(3-tert-butyl-5-methoxycarbonyl-benzyl)-2-[3-[(triphenyl-methyl)thio]-propyl]malonic acid XI (9.0 g, 90%) as a white solid: $^1$H NMR (CD$_3$OD) δ1.4 (s, 9H), 1.4 (m, 2H), 1.6 (m, 2H), 2.1 (t, J=8.0 Hz, 2H), 3.2 (s, 2H), 7.1-7.4 (m, 16H), 7.7 (s, 1H), 7.9 (s, 1H); $^{13}$C NMR (CD$_3$OD) δ24.8, 31.8 (3C), 32.4, 33.3, 35.6, 39.0, 59.5, 67.7, 126.2, 127.7, 128.9, 129.6, 130.7, 131.5, 132.9, 137.8, 146.2, 152.6, 170.1, 174.5.

2-(3-Tert-Butyl-5-methoxycarbonyl-benzyl)-5-[(triphenylmethyl)thio]pentanoic acid XII A solution of 2-(3-tert-butyl-5-methoxycarbonyl-benzyl)-2-[3-[(triphenylmethyl)thio]propyl]-malonic acid XI (6.71 g, 11 mmol) in DMSO (10 ml) was stirred at 130° C. for 1.5 hours. The solvent was removed under reduced pressure and water was added to the residual oil. The precipitate was filtered off, washed with water, and dried under vacuum to afford 2-(3-tert-butyl-5-methoxycarbonyl-benzyl)-5-[(triphenylmethyl)thio]-pentanoic acid XII (5.86 g, 10.3 mmol, 94%) as a white solid: $^1$H NMR (CD$_3$OD) δ1.3 (s, 9H), 1.3-1.5 (m, 4H), 2.1 (m, 2H), 2.4 (m, 1H), 2.7 (m, 1H), 2.8 (m, 1H), 7.1-7.4 (m, 16H), 7.7 (s, 1H), 7.9 (s, 1H); $^{13}$C NMR (CD$_3$OD) δ27.4, 31.7 (3C), 32.3, 32.7, 35.6, 39.2, 48.4, 67.7, 125.7, 127.7, 128.6, 128.9, 130.8, 131.6, 132.0, 140.8, 146.3, 152.7, 170.3, 178.8.

3-Carboxy-5-(1,1-dimethylethyl)-alpha-(3-mercaptopropyl)-benzenepropanoic acid To a solution of 2-(3-tert-butyl-5-methoxycarbonyl-benzyl)-5-[(triphenylmethyl)thio]pentanoic acid XII (5.5 g, 9.7 mmol) in dichloromethane (30 mL) were added triisopropylsilane (2.4 mL, 11.6 mmol) and trifluoroacetic acid (10 mL), and the mixture was stirred at room temperature for 10 minutes. The solvent was removed under reduced pressure and the crude material was purified by silica gel chromatography (1% AcOH in Hexanes/EtOAc, 4:1) to afford 3-carboxy-5-(1,1-dimethylethyl)-alpha-(3-mercaptopropyl)-benzenepropanoic acid (1.7 g, 5.3 mmol, 55%) as a white solid: $^1$H NMR (CD$_3$OD) δ1.3 (s, 9H), 1.5-1.8 (m, 4H), 2.4 (m, 2H), 2.6-2.7 (m, 1H), 2.8-2.9 (m, 1H), 2.9-3.0 (m, 1H), 7.5 (s, 1H), 7.7 (s, 1H), 7.8 (s, 1H); $^{13}$C NMR (CD$_3$OD) δ24.8, 31.7 (3C), 31.9, 32.9, 35.6, 39.5, 48.6, 125.7, 128.5, 131.6, 132.0, 140.9, 152.8, 170.3, 179.0. Elemental analysis calculated for C$_{17}$H$_{24}$O$_4$S: C, 62.93; H, 7.46; S, 9.88. Found: C, 63.02; H, 7.36; S, 9.82.

Example 6

Preparation of 3-(1-Carboxy-4-mercaptobutoxy)-benzoic Acid (Scheme VII)

Methyl 3-(4-acetylthio-1-methoxycarbonyl-butoxy)-benzoate XV

To a solution of methyl 2,5-dibromopentanoate XIII (22.00 g, 80.3 mmol) and methyl 3-hydroxybenzoate XIV (10.18 g, 66.9 mmol) in DMF (80 mL) was added K$_2$CO$_3$ (12.94 g, 93.7 mmol) at room temperature. The mixture was stirred at room temperature under N$_2$ for 12 hours, then heated at 70° C. for 1 hour. Potassium thioacetate (22.93 g, 200.8 mmol) was added to the mixture, which was heated at 70° C. for 2 hours. The mixture was allowed to cool to room temperature and was diluted with EtOAc (1000 mL). The mixture was washed with H$_2$O (3×300 mL) and brine (2×300 mL). The organic layer was dried over MgSO$_4$, filtered and concentrated. The crude product was purified by flash chromatography (gradient elution: 10% to 20% EtOAc/hexanes) to afford methyl 3-(4-acetylthio-1-methoxycarbonyl-butoxy)-benzoate XV (8.40 g, 24.7 mmol, 37%) as a yellow oil: R$_f$ 0.26 (hexanes/EtOAc, 4:1): $^1$H NMR (CDCl$_3$) δ1.73-1.88 (m, 2H), 2.01-2.08 (m, 2H), 2.32 (s, 3H), 2.93 (t, J=7.2 Hz, 2H), 3.75 (s, 3H), 3.89 (s, 3H), 4.69 (t, J=6.2 Hz, 1H), 7.07 (dm, J=8.0 Hz, 1H), 7.33 (t, J=7.9 Hz, 1H) 7.50 (m, 1H), 7.65 (dm, J=7.7 Hz, 1H); $^{13}$C NMR (CDCl$_3$) δ25.3, 28.3, 30.5, 31.4, 52.1, 52.2, 75.8, 115.4, 120.0, 122.8, 129.5, 131.4, 157.5, 166.4, 171.3, 195.4.

3-(1-Carboxy-4-mercaptobutoxy)-benzoic acid

A solution of methyl 3-(4-acetylthio-1-methoxycarbonyl-butoxy)benzoate XV (8.00 g, 23.5 mmol) in THF (60 mL) was deoxygenated by bubbling N$_2$ through the solution for 1 hour. To the solution was added deoxygenated 3 N NaOH (47 mL, 141 mmol) and the mixture was stirred for 24 hours at room temperature under N$_2$. The mixture was acidified with 1 N HCl and extracted with EtOAc (3×300 mL). The organic extracts were washed with water (300 mL) and brine (300 mL), dried over MGSO$_4$, filtered, and concentrated. The residual oil was dissolved in ether and the solution was concentrated to afford 3-(1-carboxy-4-mercaptobutoxy)-benzoic acid (4.40 g, 16.3 mmol, 69%) as a white solid: $^1$H NMR (CDCl$_3$) δ1.40 (t, J=7.9 Hz, 1H), 1.83-1.99 (m, 2H), 2.11-2.22 (m, 2H), 2.63 (m, 2H), 4.76 (dd, J=7.3, 5.0 Hz, 1H), 7.23 (m, 1H), 7.38 (t, J=7.8 Hz, 1H), 7.49 (m, 1H), 7.72 (d, J=7.7 Hz, 1H); $^{13}$C NMR (CDCl$_3$) δ24.1, 29.6, 31.2, 75.5, 114.8, 122.1, 123.9, 129.9, 130.5, 157.6, 171.8, 177.1. Elemental analysis calculated for C$_{12}$H$_{14}$O$_5$S: C, 53.32; H, 5.22; S, 11.86. Found: C, 53.04; H, 5.38; S, 11.58.

Example 7

Preparation of (+)-3-carboxy-α-(3-mercaptopropyl)-benzenepropanoic acid 53 and (−)-3-carboxy-α-(3-mercaptopropyl)-benzenepropanoic acid A solution of racemic 3-carboxy-α-(3-mercaptopropyl) benzenepropanoic acid (2.70 g, 10.1 mmol) was divided into multiple samples of equal volume, and each of them was passed through a CHIRAPAK AD column (250 mm×21 mm id) using carbon dioxide/methanol (77/23, v/v) as eluent at a flow rate of 25 mL/min, at 25° C. The first eluting peak (detected by UV at 290 nm) from each run was combined and concentrated to afford (+)-3-carboxy-α-(3-mercaptopropyl)-benzenepropanoic acid (1.02 g, 38%) as a colorless oil: [α]$^{25}$D=+15.5 (c=1.1, CH3CN). (−)-3-carboxy-α-(3-mercaptopropyl)-benzenepropanoic acid (1.08 g. 40%) was obtained likewise from the second peaks as a colorless oil: [α]$^{25}$D=−13.4 (c=1.1, CH$_3$CN)

Example 8

Preparation 3-(2-Mercaptoethyl)-[1,1'-biphenyl]-2,3'-dicarboxylic Acid (Scheme VIII)

3-(2,2-Dimethyl-4-oxo-4H-1,3-benzodioxin-5-yl)-benzoic acid, ethyl ester

To a solution of 2,2-dimethyl-5-trifluoro-methanesulfonyloxy-4H-1,3-benzodioxin-4-one (2.0 g, 5.8 mmol), 3-ethoxycarbonylphenylboronic acid (1.34 g, 6.9 mmol) and anhydrous K$_2$CO$_3$ powder (2.61 g, 18.9 mmol) in DMF (30 mL) was added tetrakis(triphenylphosphine) palladium (0.202 g, 0.175 mmol). The mixture was heated at reflux for 2 hours. The reaction mixture was allowed to cool to room temperature and 1 N HCl (25 mL) was added. The mixture was extracted with EtOAc (3×25 mL). The combined extracts were washed with water and brine, then dried over MgSO$_4$, filtered, and concentrated. The crude material was purified by flash chromatography (1:15 EtOAc/hexanes) to afford 3-(2,2-dimethyl-4-oxo-4H-1,3-benzodioxin-5-yl)-benzoic acid, ethyl ester (1.2 g, 63%) as a white solid: $^1$H NMR (CDCl$_3$) δ 1.39 (t, J=7.1 Hz, 3H), 1.80 (s, 6H), 4.39 (q, J=7.0 Hz, 2H), 7.01 (d, J=8.0 Hz, 2H), 7.47-7.57 (m, 3H), 8.00 (t, J=1.5 Hz, 1H) 8.07 (dt, J=7.5, 1.5 Hz, 1H).

3-Hydroxy-[1,1'-biphenyl]-2,3'-dicarboxylic acid, dimethyl ester

To a solution of 3-(2,2-dimethyl-4-oxo-4H-1,3-benzodioxin-5-yl)benzoic acid, ethyl ester (1.4 g, 4.3 mmol) in methanol (10 mL) was added sodium methoxide (0.5 M in methanol, 25 mL) at 0° C. The solution was stirred at room temperature for 15 minutes. The reaction was quenched by addition of 1 N HCl (30 mL) and extracted with EtOAc (3×30 mL). The combined organic extracts were dried over $MgSO_4$ and concentrated to afford 3-hydroxy-[1,1'-biphenyl]-2,3'-dicarboxylic acid, dimethyl ester (1.2 g, 95%) as a yellow solid: $^1$H NMR (CDCl$_3$) δ 3.43 (s, 3H), 3.93 (s, 3H), 6.79 (dd, J=7.5, 0.9 Hz, 1H), 7.04 (dd, J=7.5, 0.9 Hz, 1H), 7.43 (m, 3H), 7.93 (m, 1H) 8.02 (dm, J=7.0 Hz, 1H), 10.8 (s, 1H).

3-Trifluoromethanesulfonyloxy-[1,1'-biphenyl]-2,3'-dicarboxylic acid, dimethyl ester To a solution of 3-hydroxy-[1,1'-biphenyl]-2,3'-dicarboxylic acid, dimethyl ester (1.1 g, 3.8 mmol) in dichloromethane (15 mL) were added pyridine (1.00 mL, 12.3 mmol) and trifluromethanesulfonic anhydride (0.90 mL, 5.4 mmol) at 0° C. The solution was stirred at 0° C. for 2 hours. Aqueous 1 N HCl (20 mL) was added, and the mixture was extracted with dichloromethane (3×20 mL). The combined organic extracts were washed with water and brine, dried over $MgSO_4$, filtered, and concentrated to give 3-trifluoromethanesulfonyloxy-[1,1'-biphenyl]-2,3'-dicarboxylic acid, dimethyl ester (1.4 g, 87%) as a yellow solid: $^1$H NMR (CDCl$_3$) δ3.72 (s, 3H), 3.94 (s, 3H), 7.38-7.62 (m, 5H), 8.08 (m, 2H).

3-Ethenyl-[1,1'-biphenyl]-2,3'-dicarboxylic acid, dimethyl ester

A mixture of 3-trifluoromethanesulfonyloxy-[1,1'-biphenyl]-2,3'-dicarboxylic acid, dimethyl ester (1.3 g, 3.1 mmol), tetrakis (triphenylphosphine) palladium (0.36 g, 0.31 mmol), LiCl (0.94 g, 22.2 mmol), triethylamine (0.6 mL, 4.3 mmol) and tri-n-butyl(vinyl)tin (1.0 mL, 3.4 mmol) in 1,4-dioxane (30 mL) was heated at reflux under $N_2$ for 4 hours. After cooling to room temperature, the mixture was filtered through a plug of silica gel and the filtrate was concentrated. Purification by flash chromatography (1:10 EtOAc/hexanes) provided 3-ethenyl-[1,1'-biphenyl]-2,3'-dicarboxylic acid, dimethyl ester (0.91 g, 99%) as a white solid: $^1$H NMR (CDCl$_3$) δ3.61 (s, 3H), 3.92 (s, 3H), 5.40 (d, J=11.1 Hz, 1H), 5.79 (d, J=17.5 Hz, 1H), 6.87 (dd, J=17.4, 11.0 Hz, 1H), 7.31 (d, J=7.5 Hz, 1H), 7.44-7.49 (m, 2H), 7.56 (dm, J=7.5 Hz, 1H), 7.62 (d, J=8.0 Hz, 1H), 8.03 (dm, J=7.5 Hz, 1H), 8.08 (t, 1, J=1.5 Hz, 1H).

3-[2-(Acetylthio)ethyl]-[1,1'-biphenyl]-2,3'-dicarboxylic acid, dimethyl ester To a solution of 3-ethenyl-[1,1'-biphenyl]-2,3'-dicarboxylic acid, dimethyl ester (0.85 g, 2.9 mmol) in benzene (10 mL) was added thioacetic acid (2.1 mL, 29.4 mmol) followed by AIBN (0.053 g, 0.32 mmol). The solution was deoxygenated for 30 minutes by bubbling nitrogen through the solution and then heated at reflux for 4 hours. Saturated aqueous $NaHCO_3$ (20 mL) was added to the solution and the mixture was extracted with EtOAc (2×20 mL). The combined organic extracts were washed with water and brine, dried over $MgSO_4$, filtered, and concentrated. The residue was purified by flash chromatography (1:12 EtOAc/hexanes) to give 3-[2-(acetylthio)ethyl]-[1,1'-biphenyl]-2,3'-dicarboxylic acid, dimethyl ester (0.51 g, 48%) as an off white solid: $^1$H NMR (CDCl$_3$) δ2.35 (s, 3H), 2.93 (m, 2H), 3.14 (m, 2H), 3.62 (s, 3H), 3.93 (s, 3H), 7.29 (dd, J=7.6, 0.9 Hz, 1H), 7.35 (dd, J=7.5, 0.8 Hz, 1H), 7.44 (d, J=7.6 Hz, 1H), 7.48 (d, J=7.5 Hz, 1H), 7.55 (dt, J=8.0, 1.5 Hz, 1H), 8.03 (dt, J=7.9, 1.5 Hz, 1H), 8.07 (t, J=1.5 Hz, 1H).

3-(2-Mercaptoethyl)-[1,1'-biphenyl]-2,3'-dicarboxylic acid, 2-methyl ester

To a deoxygenated solution of 3-[2-(acetylthio) ethyl]-[1,1'-biphenyl]-2,3'-dicarboxylic acid, dimethyl ester (0.50 g, 1.34 mmol) in THF (3.5 mL) was added a deoxygenated solution of NaOH (0.38 g, 9.4 mmol) in water (3.5 mL). The mixture was stirred overnight, and 1 N HCl (20 mL) was added. The mixture was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid, 2-methyl ester (0.35 g, 83%) as an off white solid: $^1$H NMR (CDCl$_3$) δ1.46 (t, J=8.0 Hz, 1H), 2.83 (m, 2H), 3.00 (m, 2H), 3.60 (s, 3H), 7.33-7.31 (m, 2H), 7.46 (t, J=7.7 Hz, 1H), 7.52 (t, J=7.7 Hz, 1H), 7.61 (dm, J=7.9 Hz, 1H), 8.10 (dm, J=7.9 Hz, 1H), 8.14 (m, 1H).

3-(2-Mercaptoethyl)-[1,1'-biphenyl]-2,3'-dicarboxylic acid

To a deoxygenated suspension of sodium ethanethiolate (0.135 g, 1.60 mmol) in DMF (0.5 mL) was added a solution of 3-(2-mercaptoethyl)-[1,1'-biphenyl]-2,3'-dicarboxylic acid, 2-methyl ester (0.10 g, 0.32 mmol) in DMF (0.5 mL). Argon was bubbled through the mixture for 10 minutes. The reaction was heated at 100° C. for 1 hour and 200° C. for another hour. After the mixture cooled to room temperature, the reaction was quenched with 1 N HCl (20 mL) and was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid (0.055 g, 57%) as a white solid: $^1$H NMR (CDCl$_3$) δ1.51 (t, J=8.0 Hz, 1H), 2.87-2.93 (m, 2H), 3.12-3.08 (m, 2H), 7.37 (m, 2H), 7.57-7.47 (m, 2H), 7.70 (dm, J=7.9 Hz, 1H), 7.98 (dm, J=7.8 Hz, 1H), 8.30 (m, 1H); $^{13}$C NMR (CDCl$_3$) δ26.2, 38.8, 128.1, 129.3, 129.7, 129.8, 129.9 (2C), 130.5, 133.3, 134.4, 137.7, 139.1, 141.2, 172.3, 176.9. Elemental analysis calculated for $C_{16}H_{14}O_4S$: C, 63.56; H, 4.67; S, 10.61. Found: C, 63.65; H, 4.88; S, 10.33.

Example 9

Preparation of 2-[(4-carboxyphenyl)methoxy]-6-(2-mercaptoethyl)-benzoic Acid (Scheme IX)

5-Ethenyl-2,2-dimethyl-4H-1,3-benzodioxin-4-one

A mixture of 2,2-dimethyl-5-trifluoromethanesulfonyloxy-4H-1,3-benzodioxin-4-one (9.90 g, 30.3 mmol), tributyl(vinyl)tin (10.10 g, 31.9 mmol), lithium chloride (8.70 g, 205 mmol), and triethylamine (5.0 mL, 36.0 mmol) in 1,4-dioxane (300 mL) was deoxygenated by bubbling nitrogen through the mixture for 1 hour. To the mixture was added tetrakis(triphenylphosphine)palladium (3.40 g, 2.90 mmol) and the mixture was heated at 100° C. for 3 hours.

The mixture was allowed to cool to room temperature and was filtered. The filtrate was concentrated and purified by flash chromatography (1:12, EtOAc/hexanes) to provide 5-ethenyl-2,2-dimethyl-4H-1,3-benzodioxin-4-one (5.00 g, 81%) as a yellow oil: H NMR: (CDCl$_3$) δ1.72 (s, 6H), 5.43 (dd, J=11.0, 1.3 Hz, 1H), 5.72 (dd, J=17.5, 1.3 Hz, 1H), 6.89 (d, J=8.0 Hz, 1H), 7.27 (d, J=8.0 Hz, 1H), 7.47 (t, J=8.0 Hz, 1H), 7.73 (dd, J=17.5, 11.0 Hz, 1H).

2-Ethenyl-6-hydroxybenzoic acid, methyl ester

To 5-ethenyl-2,2-dimethyl-4H-1,3-benzodioxin-4-one (4.01 9, 19.6 mmol) was added 0.5 M sodium methoxide in methanol (85 mL, 42.5 mmol) at room temperature. Aqueous 1 N HCl (100 mL) was added to the solution after 15 minutes. The cloudy solution was extracted with ether (2×100 mL). The combined organic extracts were washed with H$_2$O (50 mL) and brine (50 mL), dried over Na$_2$SO$_4$, filtered, and concentrated to afford 2-ethenyl-6-hydroxybenzoic acid, methyl ester (2.0 g, 57%) as a yellow oil. This material was used without further purification in the next step: $^1$H NMR (CDCl$_3$) δ 3.96 (s, 3H), 5.26 (dd, J=10.8, 1.5 Hz, 1H), 5.49 (dd, J=17.3, 1.5 Hz, 1H), 6.95 (m, 2H), 7.23-7.39 (m, 2H), 11.12 (s, 1H).

2-Ethenyl-6-[4-(methoxycarbonyl)phenyl]methoxy-benzoic acid, methyl ester

To a stirred solution of the above material (0.500 g, 2.8 mmol) in acetone (10 mL) were added K$_2$CO$_3$ (1.50 g, 10.9 mmol) and methyl 4-(bromomethyl)benzoate (0.71 g, 3.10 mmol) at room temperature. The mixture was stirred under nitrogen for 3 hours and filtered. The filtrate was concentrated and residue was purified by flash chromatography (1:10 EtOAc/hexanes) to provide 2-ethenyl-6-[4-(methoxycarbonyl)phenyl]methoxy-benzoic acid, methyl ester (0.73 g, 80%) as a white solid: $^1$H NMR (CDCl$_3$) δ3.92 (s, 6H), 5.17 (s, 2H), 5.37 (dd, J=11.1, 1.0 Hz, 1H), 5.78 (dd, J=17.6, 0.9 Hz, 1H), 6.70 (dd, 1, J=17.4, 11.1 Hz, 1H), 6.83 (d, J=7.8 Hz, 1H), 7.20 (d, J=8.0 Hz, 1H) 7.29 (t, J=8.0 Hz, 1H), 7.46 (d, J=8.4 Hz, 2H), 8.04 (d, J=8.3 Hz, 2H).

2-[2-(Acetylthio)ethyl]-6-[4-(methoxycarbonyl)phenyl]-methoxy-benzoic acid, methyl ester To a solution of 2-ethenyl-6-[4-(methoxycarbonyl)phenyl]methoxy-benzoic acid, methyl ester (0.71 g, 2.18 mmol) in benzene (10 mL) was added thioacetic acid (1.80 mL, 25.2 mmol) followed by AIBN (37 mg, 0.23 mmol). After nitrogen was bubbled through the solution for 30 minutes, the solution was heated at reflux for 4 hours. The reaction was allowed to cool to room temperature and saturated NaHCO$_3$ (20 mL) was added. The mixture was extracted with EtOAc (3×20 mL). The combined organic extracts were washed with water and brine, dried over MgSO$_4$, filtered and concentrated in vacuo. The residue was purified by flash chromatography (1:10 EtOAc/hexanes) to give 2-[2-(acetylthio)ethyl]-6-[4-(methoxycarbonyl)-phenyl] methoxy-benzoic acid, methyl ester (0.50 g, 60%) as a clear oil: $^1$H NMR (CDCl$_3$) δ2.34 (s, 3H), 2.85-2.82 (m, 2H), 3.07-3.10 (m, 2H), 3.92 (s, 3H), 3.94 (s, 3H), 5.16 (s, 2H), 6.81 (d, J=8.2 Hz, 1H), 6.92 (d, J=7.7 Hz, 1H), 7.28 (t, J=8.2 Hz, 1H), 7.46 (d, J=8.3 Hz, 2H), 8.04 (d, J=8.3 Hz, 2H).

2-[(4-Carboxyphenyl)methoxy]-6-(2-mercaptoethyl)-benzoic acid

To a deoxygenated solution of 2-[2-(acetylthio)ethyl]-6-[4-(methoxycarbonyl)phenyl]methoxy-benzoic acid, methyl ester (0.20 g, 0.50 mmol) in 95% EtOH (3 mL) was added a deoxygenated solution of KOH (0.463 g, 8.3 mmol) in 95% EtOH (3 mL) under nitrogen. The solution was heated at reflux overnight and quenched by addition of 1 N HCl (20 mL). The mixture was extracted with EtOAc (3×20 mL) and the combined organic extracts were washed with water and brine, then dried over MgSO$_4$, filtered, and concentrated. Purification by flash chromatography (1:1 dichloromathane/hexanes with 1% acetic acid) provided 2-[(4-carboxyphenyl)methoxy]-6-(2-mercaptoethyl)-benzoic acid (0.077 g, 46%) as a white solid: $^1$H NMR (CD$_3$OD) δ2.75 (m, 2H), 2.92 (m, 2H), 5.22 (s, 2H), 6.93 (d, J=7.5 Hz, 1H), 6.98 (d, J=8.2 Hz, 1H), 7.30 (t, J=8.3 Hz, 1H), 7.55 (d, J=7.9 Hz, 2H), 8.02 (d, J=8.0 Hz, 2H); $^{13}$C NMR (CD$_3$OD) δ26.5, 39.8, 71.1, 112.4, 123.9, 126.9, 128.3, 131.3, 131.7, 131.8, 139.9, 144.2, 156.7, 170.0, 172.3. Elemental analysis calculated for C$_{17}$H$_{16}$O$_5$S: C, 61.43; H, 4.85; S, 9.65. Found: C, 61.16; H, 4.95; S, 9.44.

Example 10

Preparation of 4-mercaptomethyl-[1,1'-biphenyl]-2,3'-dicarboxylic acid (Scheme X)

4-Methyl-[1,1'-biphenyl]-2,3'-dicarboxylic acid

To a solution of 2-bromo-5-methylbenzoic acid (5.00 g, 23.3 mmol) in DME (100 mL) were added 3-carboxyphenylboronic acid (3.86 g; 23.3 mmol), a solution of Na$_2$CO$_3$ (9.90 g, 93 mmol) in H$_2$O and tetrakis(triphenylphosphine) palladium. The mixture was stirred at 90° C. for 4 days. The mixture was allowed to cool to room temperature, diluted with EtOAc (50 mL), and washed with a saturated NaHCO$_3$ solution. The aqueous layer was separated, acidified with 10% HCl, and extracted with EtOAc (3×20 mL). The combined extracts were dried over MgSO$_4$ and concentrated. The crude material was purified by column chromatography (9:1 hexanes/EtOAc 1% acetic acid) to afford 4-methyl-[1,1'-biphenyl]-2,3'-dicarboxylic acid (2.20 g, 37%) as a solid: H NMR (DMSO-d$_6$) δ 2.40 (s, 3H), 7.30 (m, 1H), 7.42 (m, 1H), 7.52-7.57 (m, 2H), 7.60 (s, 1H), 7.85 (s, 1H), 7.91-7.92 (m, 1H).

4-Methyl-[1,1'-biphenyl]-2,3'-dicarboxylic acid, dimethyl ester

To a solution of 4-methyl-[1,1'-biphenyl]-2,3'-dicarboxylic acid (2.20 g, 8.6 mmol) in methanol (150 mL) was added conc. H$_2$SO$_4$ (1.6 mL) and the mixture was heated at reflux overnight. The solvent was removed under a reduced pressure and the residue was partitioned between saturated aqueous NaHCO$_3$ solution and EtOAc (20 mL). The organic layer was dried over MgSO$_4$ and concentrated to give 4-methyl-[1,1'-biphenyl]-2,3'-dicarboxylic acid, dimethyl ester (2.26 g, 92%) as a crude material. This product was used for the next reaction without further purification: $^1$H NMR (DMSO-d$_6$) δ 2.41 (s, 3H), 3.58 (s, 3H), 3.88 (s, 3H), 7.36-7.38 (m, 1H), 7.47-7.48 (m, 1H), 7.56-7.58 (m, 2H), 7.62 (s, 1H), 7.82 (s, 1H), 7.94-7.96 (m, 1H).

4-Bromomethyl-[1,1'-biphenyl]-2,3'-dicarboxylic acid, dimethyl ester

To a solution of 4-methyl-[1,1'-biphenyl]-2,3'-dicarboxylic acid, dimethyl ester (2.26 g, 7.9 mmol) in $CCl_4$ (50 mL) were added benzoyl peroxide (0.010 g, 0.04 mmol) and NBS (1.42 g, 8.0 mmol), and the mixture was refluxed for 3 days. The reaction mixture was allowed to cool to room temperature, filtered, and concentrated. The residue was purified by column chromatography (95:5 to 90:10 hexanes/EtOAc) to afford 4-bromomethyl-[1,1'-biphenyl]-2,3'-dicarboxylic acid, dimethyl ester (1.71 g, 60%): $^1$H NMR (DMSO-$d_6$) δ 3.61(s, 3H), 3.88 (s, 3H), 4.84 (s, 2H), 7.48-7.50 (d, J=8.0 Hz, 1H), 7.59-7.60 (m, 2H), 7.72-7.75 (m, 1H), 7.85 (s, 1H), 7.90 (m, 1H), 7.97-7.99 (m, 1H).

4-Acetylthiomethyl-[1,1'-biphenyl]-2,3'-dicarboxylic acid, dimethyl ester

To a solution of 4-bromomethyl-[1,1'-biphenyl]-2,3'-dicarboxylic acid, dimethyl ester (1.59 g, 4.4 mmol) in acetone (75 mL) was added potassium thioacetate (0.60 g, 5.3 mmol), and the mixture was ref luxed for 1 hour. The mixture was allowed to cool to room temperature, filtered, and concentrated. The residual product was purified by column chromatography (hexanes/EtOAc, 9/1) to afford 4-acetylthiomethyl-[1,1'-biphenyl]-2,3'-dicarboxylic acid, dimethyl ester (1.21 9, 76%): $^1$H NMR (DMSO-$d_6$) δ 2.39 (s, 3H), 3.60 (s, 3H), 3.88 (s, 3H), 4.23 (s, 2H), 7.42-7.44 (d, J=8.0 Hz, 1H), 7.57-7.60 (m, 3H), 7.74 (s 1H), 7.83 (s, 1H), 7.96-7.99 (m, 1H).

4-Mercaptomethyl-[1,1'-biphenyl]-2,3'-dicarboxylic acid

To a solution of 4-acetylthiomethyl-[1,1'-biphenyl]-2,3'-dicarboxylic acid, dimethyl ester (0.27 g, 0.75 mmol) in deoxygenated THF was added a degassed solution of sodium hydroxide (0.12 g, 3.0 mmol) in $H_2O$ (5 mL) at room temperature. After 24 hours, additional solution of sodium hydroxide (0.09 g) in $H_2O$ (2 mL) was added to the reaction mixture and the mixture was stirred for 24 hours. The mixture was acidified with 10% HCl and extracted with EtOAc. The extract was dried over $MgSO_4$ and concentrated. The crude material was purified by column chromatography with (9:1 dichloromethane/EtOAc with 1% acetic acid) to afford 4-mercaptomethyl-[1,1'-biphenyl]-2,3'-dicarboxylic acid (0.20 g, 92%) as a white solid: $^1$H NMR (DMSO-$d_6$) δ 3.10 (t, J=8.03 Hz, 1H), 3.89 (d, J=8.03 Hz, 2H), 7.43 (d, J=7.53 Hz, 1H), 7.58-7.65 (m, 3H), 7.83 (d, J=2.01 Hz, 1H), 7.92 (s, 1H), 7.97-8.00 (m, 1H). Elemental analysis calculated for $C_{15}H_{12}O_4S \cdot 0.5$ AcOH: C, 60.37; H, 4.43; O, 25.13; S, 10.07. Found: C, 60.28; H, 4.45; S, 10.15.

Example 11

Preparation of Precursor Compound 3-(2-Mercaptoethyl)-[1,1'-biphenyl]-2,3'-dicarboxylic Acid (Scheme XVIII)

3-(2,2-Dimethyl-4-oxo-4H-1,3-benzodioxin-5-yl)-benzoic acid, ethyl ester

To a solution of 2,2-dimethyl-5-trifluoromethanesulfonyloxy-4H-1,3-benzodioxin-4-one (2.0 g, 5.8 mmol), 3-ethoxycarbonylphenylboronic acid (1.34 g, 6.9 mmol) and anhydrous $K_2CO_3$ powder (2.61 g, 18.9 mmol) in DMF (30 mL) was added tetrakis(triphenylphosphine)palladium (0.202 g, 0.175 mmol). The mixture was heated at reflux for 2 h. The reaction mixture was allowed to cool to room temperature ("rt") and 1 N HCl (25 mL) was added. The mixture was extracted with EtOAc (3×25 mL). The combined extracts were washed with water and brine, then dried over $MgSO_4$, filtered, and concentrated. The crude material was purified by flash chromatography (1:15 EtOAc/hexanes) to afford 3-(2,2-dimethyl-4-oxo-4H-1,3-benzodioxin-5-yl)-benzoic acid, ethyl ester (1.2 g, 63%) as a white solid: $^1$H NMR (CDCl$_3$) 1.39 (t, J=7.1 Hz, 3H), 1.80 (s, 6H), 4.39 (q, J=7.0 Hz, 2H), 7.01 (d, J=8.0 Hz, 2H), 7.47-7.57 (m, 3H), 8.00 (t, J=1.5 Hz, 1H), 8.07 (dt, J=7.5, 1.5 Hz, 1H).

3-Hydroxy-[1,1'-biphenyl]-2,3'-dicarboxylic acid, dimethyl ester

To a solution of 3-(2,2-dimethyl-4-oxo-4H-1,3-benzodioxin-5-yl)benzoic acid, ethyl ester (1.4 g, 4.3 mmol) in methanol (10 mL) was added sodium methoxide (0.5 M in methanol, 25 mL) at 0° C. The solution was stirred at rt for 15 min. The reaction was quenched by addition of 1 N HCl (30 mL) and extracted with EtOAc (3×30 mL). The combined organic extracts were dried over $MgSO_4$ and concentrated to afford 3-hydroxy-[1,1'-biphenyl]-2,3'-dicarboxylic acid, dimethyl ester (1.2 g, 95%) as a yellow solid: H NMR (CDCl$_3$) 3.43 (s, 3H), 3.93 (s, 3H), 6.79 (dd, J=7.5, 0.9 Hz, 1H), 7.04 (dd, J=7.5, 0.9 Hz, 1H), 7.43 (m, 3H), 7.93 (m, 1H), 8.02 (dm, J=7.0 Hz, 1H), 10.8 (s, 1H).

3-Trifluoromethanesulfonyloxy-[1,1'-biphenyl]-2,3'-dicarboxylic acid, dimethyl ester To a solution of 3-hydroxy-[1,1'-biphenyl]-2,3'-dicarboxylic acid, dimethyl ester (1.1 g, 3.8 mmol) in dichloromethane (15 mL) were added pyridine (1.00 mL, 12.3 mmol) and trifluoromethanesulfonic anhydride (0.90 mL, 5.4 mmol) at 0° C. The solution was stirred at 0° C. for 2 h. Aqueous 1 N HCl (20 mL) was added, and the mixture was extracted with dichloromethane (3×20 mL). The combined organic extracts were washed with water and brine, dried over $MgSO_4$, filtered, and concentrated to give 3-trifluoromethanesulfonyloxy-[1,1'-biphenyl]-2,3'-dicarboxylic acid, dimethyl ester (1.4 g, 87%) as a yellow solid: $^1$H NMR (CDCl$_3$) 3.72 (s, 3H), 3.94 (s, 3H), 7.38-7.62 (m, 5H), 8.08 (m, 2H).

3-Ethenyl-[1,1'-biphenyl]-2,3'-dicarboxylic acid, dimethyl ester

A mixture of 3-trifluoromethanesulfonyloxy-[1,1'-biphenyl]-2,3'-dicarboxylic acid, dimethyl ester (1.3 g, 3.1 mmol), tetrakis(triphenylphosphine)palladium (0.36 g, 0.31 mmol), LiCl (0.94 g, 22.2 mmol), triethylamine (0.6 mL, 4.3 mmol) and tri-n-butyl(vinyl)tin (1.0 mL, 3.4 mmol) in 1,4-dioxane (30 mL) was heated at reflux under $N_2$ for 4 h. After cooling to rt, the mixture was filtered through a plug of silica gel and the filtrate was concentrated. Purification by flash chromatography (1:10 EtOAc/hexanes) provided 3-ethenyl-[1,1'-biphenyl]-2,3'-dicarboxylic acid, dimethyl ester (0.91 g, 99%) as a white solid: $^1$H NMR (CDCl$_3$) 3.61 (s, 3H), 3.92 (s, 3H), 5.40 (d, J=11.1 Hz, 1H), 5.79 (d, J=17.5 Hz, 1H), 6.87 (dd, J=17.4, 11.0 Hz, 1H), 7.31 (d, J=7.5 Hz, 1H), 7.44-7.49 (m, 2H), 7.56 (dm, J=7.5 Hz, 1H), 7.62 (d, J=8.0 Hz, 1H), 8.03 (dm, J=7.5 Hz, 1H), 8.08 (t, 1, J=1.5 Hz, 1H).

3-[2-(Acetylthio)ethyl]-[1,1'-biphenyl]-2,3'-dicarboxylic acid, dimethyl ester To a solution of 3-ethenyl-[1,1'-biphenyl]-2,3'-dicarboxylic acid, dimethyl ester (0.85 g, 2.9 mmol) in benzene (10 mL) was added thioacetic acid (2.1 mL, 29.4 mmol) followed by AIBN (0.053 g, 0.32 mmol). The solution was deoxygenated for 30 min by bubbling nitrogen through the solution and then heated at reflux for 4 h. Saturated aqueous $NaHCO_3$ (20 mL) was added to the solution and the mixture was extracted with EtOAc (2×20 mL). The combined organic extracts were washed with water and brine, dried over $MgSO_4$, filtered, and concentrated. The residue was purified by flash chromatography (1:12 EtOAc/hexanes) to give 3-[2-(acetylthio)ethyl]-[1,1'-biphenyl]-2,3'-dicarboxylic acid, dimethyl ester (0.51 g, 48%) as an off white solid: $^1H$ NMR ($CDCl_3$) 2.35 (s, 3H), 2.93 (m, 2H), 3.14 (m, 2H), 3.62 (s, 3H), 3.93 (s, 3H), 7.29 (dd, J=7.6, 0.9 Hz, 1H), 7.35 (dd, J=7.5, 0.8 Hz, 1H), 7.44 (d, J=7.6 Hz, 1H), 7.48 (d, J=7.5 Hz, 1H), 7.55 (dt, J=8.0, 1.5 Hz, 1H), 8.03 (dt, J=7.9, 1.5 Hz, 1H), 8.07 (t, J=1.5 Hz, 1H).

3-(2-Mercaptoethyl)-[1,1'-biphenyl]-2,3'-dicarboxylic acid, 2-methyl ester

To a deoxygenated solution of 3-[2-(acetylthio)ethyl]-[1,1'-biphenyl]-2,3'-dicarboxylic acid, dimethyl ester (0.50 g, 1.34 mmol) in THF (3.5 mL) was added a deoxygenated solution of NaOH (0.38 g, 9.4 mmol) in water (3.5 mL). The mixture was stirred overnight, and 1 N HCl (20 mL) was added. The mixture was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid, 2-methyl ester (0.35 g, 83%) as an off white solid: $^1H$ NMR ($CDCl_3$) 1.46 (t, J=8.0 Hz, 1H), 2.83 (m, 2H), 3.00 (m, 2H), 3.60 (s, 3H), 7.33-7.31 (m, 2H), 7.46 (t, J=7.7 Hz, 1H), 7.52 (t, J=7.7 Hz, 1H), 7.61 (dm, J=7.9 Hz, 1H), 8.10 (dm, J=7.9 Hz, 1H), 8.14 (m, 1H).

3-(2-Mercaptoethyl)-[1,1'-biphenyl]-2,3'-dicarboxylic acid

To a deoxygenated suspension of sodium ethanethiolate (0.135 g, 1.60 mmol) in DMF (0.5 mL) was added a solution of 3-(2-mercaptoethyl)-[1,1'-biphenyl]-2,3'-dicarboxylic acid, 2-methyl ester (0.10 g, 0.32 mmol) in DMF (0.5 mL) Argon was bubbled through the mixture for 10 min. The reaction was heated at 100° C. for 1 h and 200° C. for another hour. After the mixture cooled to rt, the reaction was quenched with 1 N HCl (20 mL) and was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid (0.055 g, 57%) as a white solid: $^1H$ NMR ($CDCl_3$) 1.51 (t, J=8.0 Hz, 1H), 2.87-2.93 (m, 2H), 3.12-3.08 (m, 2H), 7.37 (m, 2H), 7.57-7.47 (m, 2H), 7.70 (dm, J=7.9 Hz, 1H), 7.98 (dm, J=7.8 Hz, 1H), 8.30 (m, 1H); $^{13}C$ NMR ($CDCl_3$) 26.2, 38.8, 128.1, 129.3, 129.7, 129.8, 129.9 (2C), 130.5, 133.3, 134.4, 137.7, 139.1, 141.2, 172.3, 176.9. Anal. Calcd for $C_{16}H_{14}O_4S$: C, 63.56; H, 4.67; S, 10.61. Found: C, 63.65; H, 4.88; S, 10.33.

Example 12

In Vitro Inhibition of NAALADase Activity

Various compounds used in the inventive methods and pharmaceutical compositions have been tested for in vitro inhibition of NAALADase activity. The experimental protocol and some of the results are set forth in U.S. Pat. Nos. 5,672,592, 5,795,877, 5,863,536, 5,880,112, 5,902,817, 5,962,521, 5,968,915, 6,025,344, 6,025,345, 6,028,216, 6,046,180, 6,054,444, 6,071,965 and 6,121,252, allowed U.S. patent application Ser. No. 09/228,391 for which the issue fee has been paid, copending U.S. patent application Ser. No. 09/438,970 filed Nov. 12, 1999 (corresponding to International Patent Application No. PCT/US00/30977 filed Nov. 13, 2000), and International Publications Nos. WO 99/33849, WO 00/01668 and WO 01/14390, the entire contents of which patents, patent application and publications are herein incorporated by reference, as though set forth herein in full.

Other exemplary results are provided below in TABLES II and III).

TABLE II

IN VITRO INHIBITION OF NAALADASE ACTIVITY

| Compound | $K_i$ (nM) |
|---|---|
| 4-[4-(2,4-dicarboxybenzoyl)phenoxy]-1,2-benzenedicarboxylic acid | 1170 |
| 2-[(4-carboxyphenyl)sulfonyl]-1,4-benzenedicarboxylic acid | 2370 |
| 2-[(2,5-dicarboxyphenyl)sulfonyl]-1,4-benzenedicarboxylic acid | 1870 |
| 4-[(2-carboxyphenyl)thio]-1,3-benzenedicarboxylic acid | 3980 |
| 2-[(2-carboxyphenyl)thio]-1,4-benzenedicarboxylic acid | 572 |
| 4-[3-[[3-(2,4-dicarboxyphenoxy)-propyl]-dithio]propoxy]-1,3-benzenedicarboxylic acid | 3750 |
| 5-(3-mercaptopropoxy)-1,3-benzenedicarboxylic acid | 3300 |
| 5-(2-mercaptoethoxy)-1,3-benzenedicarboxylic acid | 14500 |
| 5-[(hydroxyamino)-carbonyl]-1,3-benzenedicarboxylic acid | 1000 |
| 5-phosphono-1,3-benzenedicarboxylic acid | 14000 |
| 5-mercaptomethyl-1,3-benzenedicarboxylic acid | 6500 |
| 5-phosphonomethyl-1,3-benzenedicarboxylic acid | 3100 |
| 5-[(carboxymethyl)amino]-1,3-benzenedicarboxylic acid | 100000 |
| 5-[[(2-furanylmethyl)amino]methyl]-1,3-benzenedicarboxylic acid | 50000 |
| 2-carboxymethyl-1,4-benzenedicarboxylic acid | 9000 |
| 5-[2-(hydroxyamino)-2-oxoethyl]-1,3-benzenedicarboxylic acid | 12000 |
| 4-(2-mercaptoethyl)-1,3-benzenedicarboxylic acid | 116 |
| 5-(2-mercaptoethyl)-1,3-benzenedicarboxylic acid | 5100 |

TABLE III

IN VITRO INHIBITION OF NAALADASE ACTIVITY

| Compound | $IC_{50}$ |
|---|---|
| alpha-(3-mercaptopropyl)-3-(trifluoromethyl)-benzenepropanoic acid | 4000 |

TABLE III-continued

IN VITRO INHIBITION OF NAALADASE ACTIVITY

| Compound | IC$_{50}$ |
|---|---|
| alpha(3-mercaptopropyl)-benzenepropanoic acid | 2270 |
| 4-hydroxy-alpha-(3-mercaptopropyl)-benzenepropanoic acid | 2140 |
| 2,3,4,5,6-pentafluoro-alpha-(3-mercaptopropyl)-benzenepropanoic acid | 1000 |
| 3-carboxy-alpha-(3-mercaptopropyl)-benzenepropanoic acid | 17 |
| 4-carboxy-alpha-(3-mercaptopropyl)-benzenepropanoic acid | 59 |
| alpha-(3-mercaptopropyl)-4-(methylsulfonyl)-benzenepropanoic acid | 211 |
| 2-cyano-alpha-(3-mercaptopropyl)-benzenepropanoic acid | 450 |
| 5-(2-carboxy-5-mercaptopentyl)-1,3-benzenedicarboxylic acid | 2.55 |
| 5-carboxy-2-chloro-alpha-(3-mercaptopropyl)-benzenepropanoic acid | 2.09 |
| 3-carboxy-4-fluoro-alpha-(3-mercaptopropyl)-benzenepropanoic acid | 12 |
| 4-(2-cyanoethyl)-alpha(3-mercaptopropyl)-benzenepropanoic acid | 316 |
| 2-(aminocarbonyl)-alpha-(3-mercaptopropyl)-benzenepropanoic acid | 3950 |
| 3-(1-carboxy-4-mercaptobutoxy)-benzoic acid | 16.3 |
| 5-mercapto-2-phenoxy-pentanoic acid | 555 |
| 2-(3,5-dimethoxyphenoxy)-5-mercapto-pentanoic acid | 16,100 |
| alpha-(3-mercaptopropyl)-2,5-dimethoxy-benzenepropanoic acid | 566 |
| alpha-(3-mercaptopropyl)-3-phenoxy-benzenepropanoic acid | 308 |
| 2-(3-hydroxyphenoxy)-5-mercapto-pentanoic acid | 846 |
| 3-(1-carboxy-4-mercaptobutoxy)-benzeneacetic acid | 64 |
| 4-(1-carboxy-4-mercaptobutoxy)-benzeneacetic acid | 82 |
| alpha-(3-mercaptopropyl)-4-phenyl-benzenepropanoic acid | 229 |
| 2-(3-acetylphenoxy-5-mercapto-pentanoic acid | 2900 |
| 2-[3-(acetylamino)phenoxy]-5-mercapto-pentanoic acid | 27700 |
| 2-(4-acetylphenoxy)-5-mercaptopentanoic acid | 29.8 |
| 4-(acetylamino)-alpha-(3-mercaptopropyl)-benzenepropanoic acid | 2200 |
| 3-(1-carboxy-4-mercaptobutoxy)-4-methoxy-benzoic acid | 287 |
| 4-(carboxymethyl)-alpha-(3-mercaptopropyl)-benzenepropanoic acid | 809 |
| 2-(1-carboxy-4-mercaptobutoxy)-benzoic acid | 4600 |
| 4-(1-carboxy-4-mercaptobutyoxy)-benzoic acid | 192 |
| 3-carboxy-2-chloro-alpha-(3-mercaptopropyl)-benzenepropanoic acid | 1200 |
| 3-carboxy-4-chloro-alpha-(3-mercaptopropyl)-benzenepropanoic acid | 175 |
| 3-(1-carboxy-4-mercaptobutoxy)-4-chloro-benzoic acid | 118 |
| 3-(1-carboxy-4-mercaptobutoxy)-4-fluoro-benzoic acid | 400 |
| 5-carboxy-2-fluoro-alpha-(3-mercaptopropyl)-benzenepropanoic acid | 6.33 |
| 5-carboxy-alpha-(3-mercaptopropyl)-2-methoxy-benzenepropanoic acid | 26 |
| 4-carboxy-alpha-(3-mercaptopropyl)-1-naphthalenepropanoic acid | 316 |
| 2-carboxy-alpha-(3-mercaptopropyl)-benzenepropanoic acid | 1700 |
| 4-carboxy-2,3,5,6-tetrafluoro-alpha-(3-mercaptopropyl)-benzenepropanoic acid | 660 |
| 5-mercapto-2-(phenylthio)-pentanoic acid | 297 |
| 3-[1-carboxy-4-mercaptobutyl)thio]-benzoic acid | 24 |
| alpha-(3-mercaptopropyl)-2-naphthalenepropanoic acid | 1130 |
| 2-chloro-alpha-(3-mercaptopropyl)-benzenepropanoic acid | 1350 |
| alpha-(3-mercaptopropyl)-3-[[(phenylmethyl)amino]carbonyl]-benzenepropanoic acid | 1130 |
| 3-bromo-5-carboxy-alpha-(3-mercaptopropyl)-benzenepropanoic acid | 2.5 |
| 3-[[(carboxymethyl)amino]carbonyl]-alpha-(3-mercaptopropyl)-benzenepropanoic acid | 286 |
| 3-bromo-4-carboxy-alpha-(3-mercaptopropyl)-benzenepropanoic acid | 146 |
| 3-carboxy-alpha-(3-mercaptopropyl)-5-nitro-benzenepropanoic acid | 3 |
| 3-carboxy-5-(1,1-dimethylethyl)-alpha-(3-mercaptopropyl)-benzenepropanoic acid | 0.05 |
| 5-carboxy-alpha-(3-mercaptopropyl)-2-nitro-benzenepropanoic acid | 8.25 |
| 3'-(2-carboxy-5-mercaptopentyl)-[1,1'-biphenyl]-3-carboxylic acid | 1.83 |
| 2-bromo-5-carboxy-alpha-(3-mercaptopropyl)-benzenepropanoic acid | 3.33 |
| (+)-3-carboxy-alpha-(3-mercaptopropyl)-benzenepropanoic acid | 7 |
| (−)-3-carboxy-alpha-(3-mercaptopropyl)-benzenepropanoic acid | 33.3 |
| 2-(2-carboxy-5-mercaptopentyl)-[1,1'-biphenyl]-4-carboxylic acid | 19 |
| 6-(2-carboxy-5-mercaptopentyl)-[1,1'-biphenyl]-2-carboxylic acid | 70 |
| 4-(2-carboxy-5-mercaptopentyl)-[1,1'-biphenyl]-2-carboxylic acid | 18 |
| 3-carboxy-alpha-(3-mercaptopropyl)-5-methoxy-benzenepropanoic acid | 13 |
| 3'-(2-carboxy-5-mercaptopentyl)-[1,1'-biphenyl]-2-carboxylic acid | 184 |
| 3-(2-carboxyphenoxy)-alpha-(3-mercaptopropyl)-benzenepropanoic acid | 49 |
| 4-(2-carboxyphenoxy)-alpha-(3-mercaptopropyl)-benzenepropanoic acid | 3590 |
| 3-carboxy-alpha-(3-mercaptobutyl)-benzenepropanoic acid | 30 |
| 4'-(2-carboxy-5-mercaptopropyl)-[1,1'-biphenyl]-2-carboxylic acid | 87 |
| alpha-(3-mercaptopropyl)-3-phenyl-benzenepropanoic acid | 181 |
| 3-carboxy-alpha-(3-mercaptopropyl)-5-phenoxy-benzenepropanoic acid | 5 |
| 3-carboxy-5-(1,1-dimethylethyl)-alpha-(3-mercaptobutyl)-benzenepropanoic acid | 1 |
| 2-(2-mercaptoethyl)-benzoic acid | 613 |
| 5-hydroxy-2-(2-mercaptoethyl)-benzoic acid | 9170 |

TABLE III-continued

IN VITRO INHIBITION OF NAALADASE ACTIVITY

| Compound | IC$_{50}$ |
|---|---|
| 5-[(4-carboxyphenyl)methoxy]-2-(2-mercaptoethyl)-benzoic acid | 71.5 |
| 2-(2-mercaptoethyl)-5-(phenylmethoxy)-benzoic acid, | 380 |
| 2-(carboxymethyl)-6-(2-mercaptoethyl)-benzoic acid | 215 |
| 5-[(3-carboxyphenyl)methoxy]-2-(2-mercaptoethyl)-benzoic acid | 84.5 |
| 2-(2-mercaptoethyl)-6-(phenylmethoxy)-benzoic acid | 11.5 |
| 2-[(2-carboxyphenyl)methoxy]-6-(2-mercaptoethyl)-benzoic acid | 11.5 |
| 2-[(4-carboxyphenyl)methoxy]-6-(2-mercaptoethyl)-benzoic acid | 4 |
| 3-(2-mercaptoethyl)-[1,1'-biphenyl]-2,3'-dicarboxylic acid | 3.46 |
| 5-(mercaptomethyl)-2-(2-phenylethoxy)-benzoic acid | 188 |
| 2-(3,3-dimethylbutoxy)-6-(2-mercaptoethyl)-benzoic acid | 2580 |
| 2-(2-mercaptoethyl)-6-(2-phenylethoxy)-benzoic acid | 266 |
| 2-[(2-chlorophenyl)methoxy]-6-(2-mercaptoethyl)-benzoic acid | 160 |
| 2-[[3-carboxy-5-(1,1-dimethylethyl)phenyl]methoxy]-6-(2-mercaptoethyl)-benzoic acid | 23.7 |
| 3-(2-mercaptoethyl)-[1,1'-biphenyl]-2,4'-dicarboxylic acid | 4.28 |
| 2-[(4-carboxy-2-methoxyphenyl)methoxy]-6-(2-mercaptoethyl)-benzoic acid | 7 |
| 2-[(4-carboxy-3-methoxyphenyl)methoxy]-6-(2-mercaptoethyl)-benzoic acid | 10.5 |
| 2-[(2-bromo-4-carboxyphenyl)methoxy]-6-(2-mercaptoethyl)-benzoic acid | 2.65 |
| 2-[(3-bromo-4-carboxyphenyl)methoxy]-6-(2-mercaptoethyl)-benzoic acid | 0.098 |
| 2-(2-mercaptoethyl)-6-phenoxy-benzoic acid | 1150 |
| 4-(mercaptomethyl)-[1,1'-biphenyl]-2,3'-dicarboxylic acid | 76 |
| 5-(mercaptomethyl)-2-(phenylmethoxy)-benzoic acid | 85 |
| 4-bromo-3-(mercaptomethyl)-benzoic acid | 3200 |
| 3-(2-mercaptoethyl)-benzoic acid | 6050 |
| 3-(mercaptomethyl)-benzoic acid | 3780 |
| 2-(mercaptomethyl)-benzoic acid | 100000 |
|  | 296.3 |

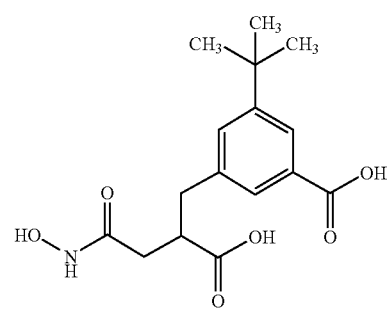

3-tert-Butyl-5-(2-carboxy-3-hydroxycarbamoyl-propyl)-benzoic acid

| Compound | IC$_{50}$ |
|---|---|
| 3-tert-Butyl-5-(2-carboxy-4-hydroxycarbamoyl-butyl)-benzoic acid | 0.2 |
| 3-(2-Carboxy-4-hydroxycarbamoyl-butyl)-benzoic acid | 47.8 |
| 3-(2-Carboxy-5-hydroxycarbamoyl-pentyl)-benzoic acid | 66.3 |
| 3-(2-Carboxy-3-hydroxycarbamoyl-propyl)-benzoic acid | 693 |
| 3-(2-Carboxy-2-hydroxycarbamoyl-ethyl)-benzoic acid | 4530 |

TABLE III-continued

IN VITRO INHIBITION OF NAALADASE ACTIVITY

| Compound | IC$_{50}$ |
|---|---|
| 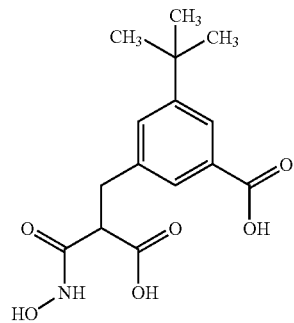<br>3-tert-Butyl-5-(2-carboxy-2-hydroxycarbamoyl-ethyl)-benzoic acid | 11900 |
| 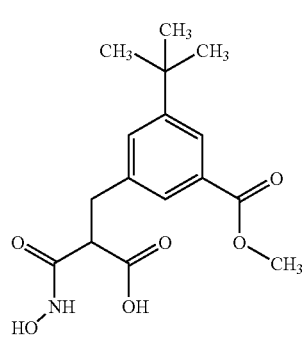<br>3-tert-Butyl-5-(2-carboxy-2-hydroxycarbamoyl-ethyl)-benzoic acid methyl ester | 38600 |
| 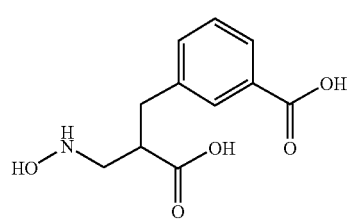<br>3-(2-Carboxy-3-hydroxyamino-propyl)-benzoic acid | 44000 |
| 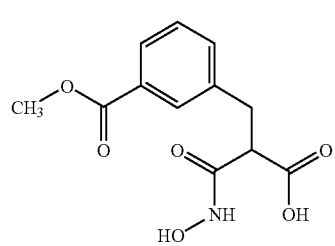<br>3-(2-Carboxy-2-hydroxycarbamoyl-ethyl)-benzoic acid methyl ester | 100000 |
| 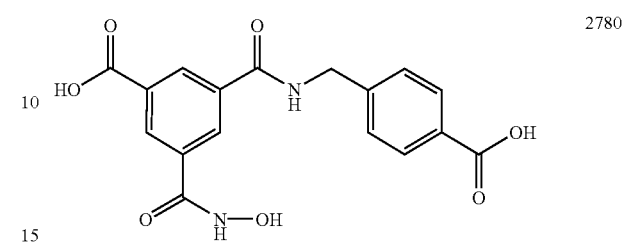 | 2780 |
| 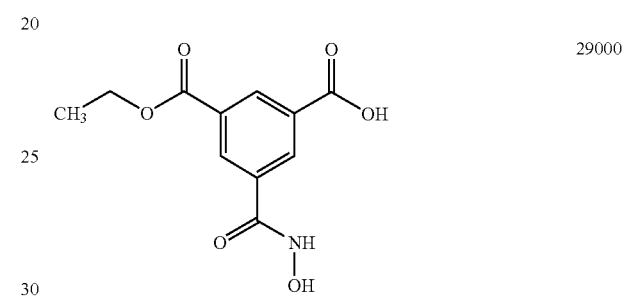<br>5-Hydroxycarbamoyl-isophthalic acid monoethyl ester | 29000 |
| 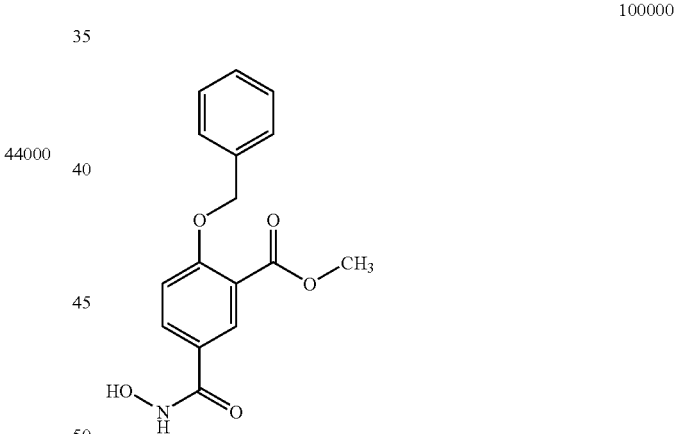<br>6-Benzyloxy-N-hydroxy-isophthalamic acid methyl ester | 100000 |
| 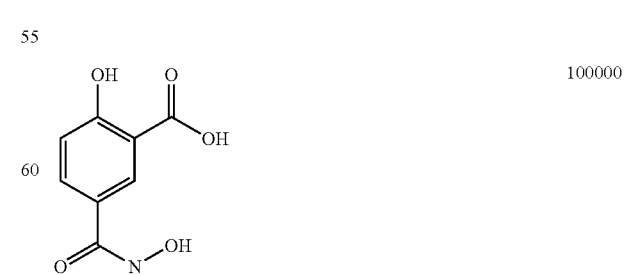<br>6,N-Dihydroxy-isophthalamic acid | 100000 |

TABLE III-continued

IN VITRO INHIBITION OF NAALADASE ACTIVITY

| Compound | IC$_{50}$ |
|---|---|
| 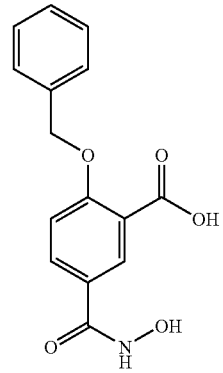 6-Benzyloxy-N-hydroxy-isophthalamic acid | 100000 |
| 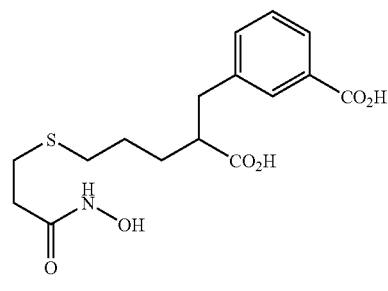 3-[2-Carboxy-5-(2-hydroxycarbamoyl-ethylsulfanyl)-pentyl]-benzoic acid | 113 |
| 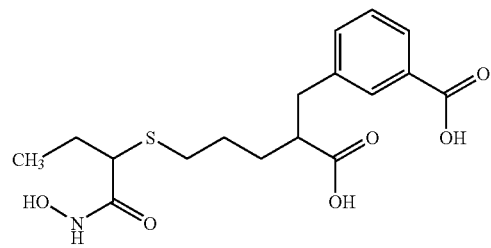 3-[2-Carboxy-5-(1-hydroxycarbamoyl-propylsulfanyl)-pentyl]-benzoic acid | 3291 |
| 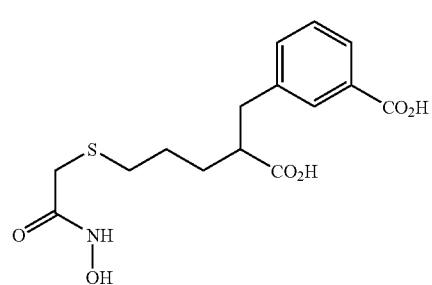 3-(2-Carboxy-5-hydroxycarbamoylmethyl-sulfanylpentyl)-benzoic acid | 384 |
| 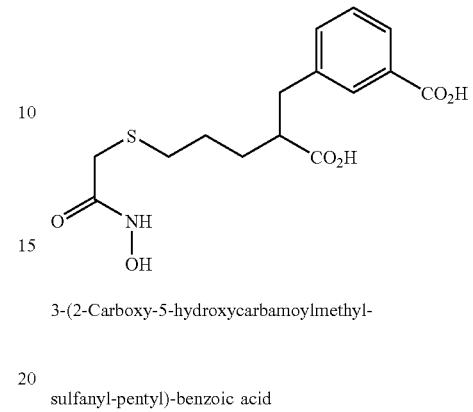 3-(2-Carboxy-5-hydroxycarbamoylmethyl-sulfanyl-pentyl)-benzoic acid | 394 |
| 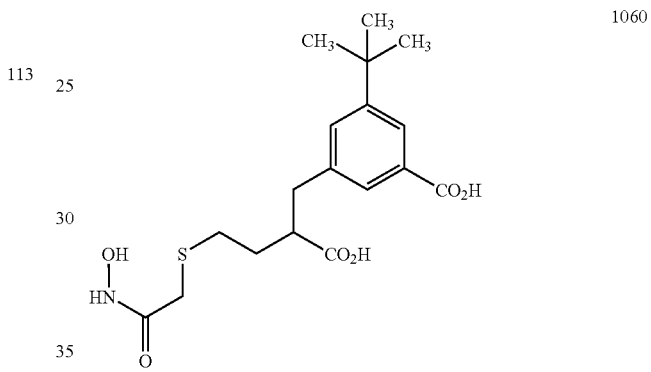 3-tert-Butyl-5-(2-carboxy-4-hydroxycarbamoylmethyl-sulfanylbutyl)-benzoic acid | 1060 |
| 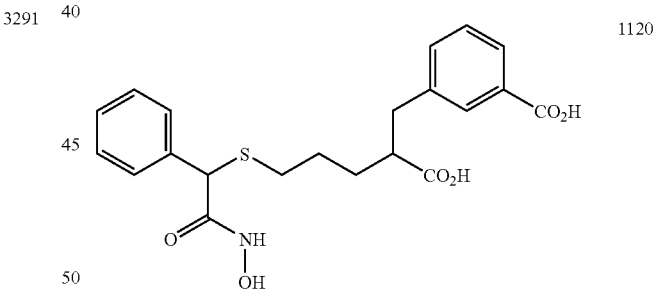 3-[2-Carboxy-5-(hydroxycarbamoyl-phenyl-methylsulfanyl)-pentyl]-benzoic acid | 1120 |
| 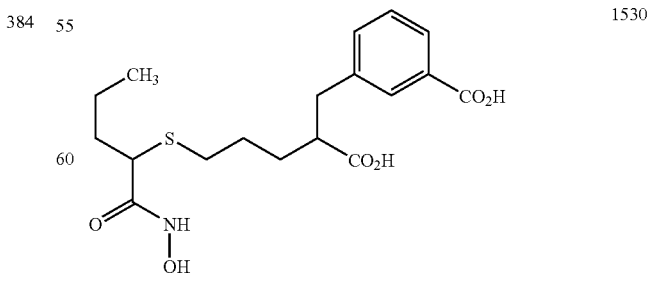 3-[2-Carboxy-5-(1-hydroxycarbamoyl-butylsulfanyl)-pentyl]-benzoic acid | 1530 |

TABLE III-continued

IN VITRO INHIBITION OF NAALADASE ACTIVITY

| Compound | $IC_{50}$ |
|---|---|
| 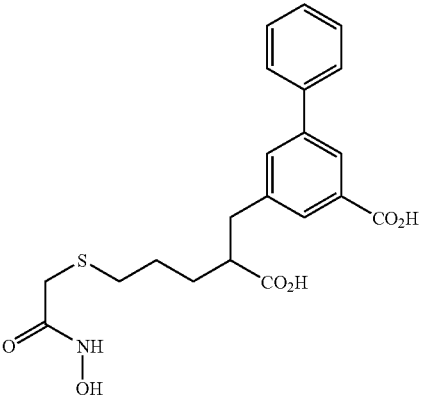<br>5-(2-Carboxy-5-hydroxycarbamoylmethyl-sulfanylpentyl)-biphenyl-3-carboxylic acid | 1690 |
| 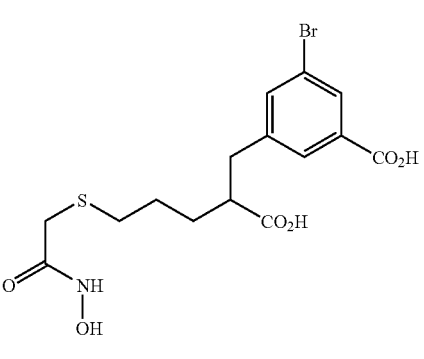<br>3-Bromo-5-(2-carboxy-5-hydroxycarbamoyl-methylsulfanylpentyl)-benzoic acid | 2460 |
| 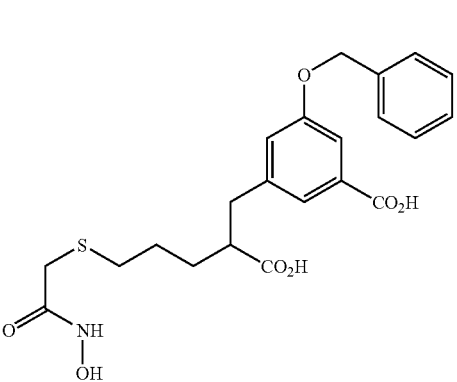<br>3-Benzyloxy-5-(2-carboxy-5-hydroxycarbamoylmethyl-sulfanylpentyl)-benzoic acid | 2570 |
| 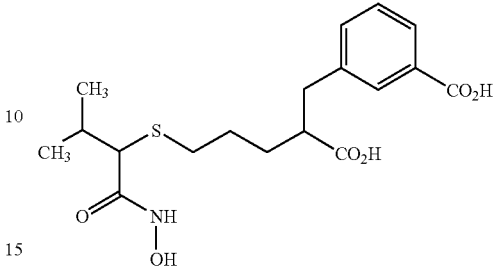<br>3-[2-Carboxy-5-(1-hydroxycarbamoyl-2-methyl-propylsulfanyl)-pentyl]-benzoic acid | 2800 |
| 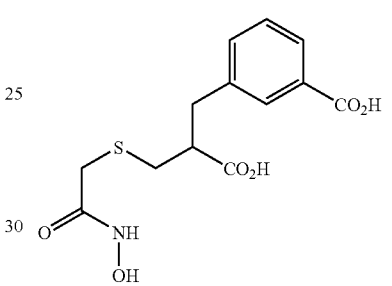<br>3-(2-Carboxy-3-hydroxycarbamoylmethyl-sulfanylpropyl)-benzoic acid | 3070 |
| 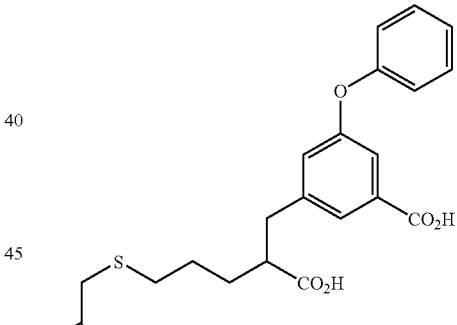<br>3-(2-Carboxy-5-hydroxycarbamoylmethyl-sulfanylpentyl)-5-phenoxy-benzoic acid | 3250 |
| 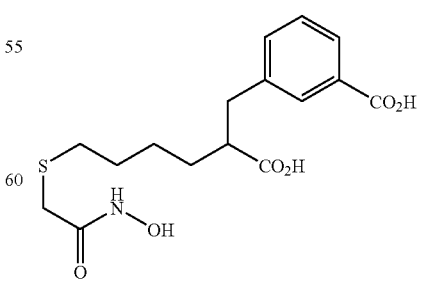<br>3-(2-Carboxy-6-hydroxycarbamoylmethyl-sulfanylhexyl)-benzoic acid | 3330 |

TABLE III-continued

IN VITRO INHIBITION OF NAALADASE ACTIVITY

| Compound | IC$_{50}$ |
|---|---|
| 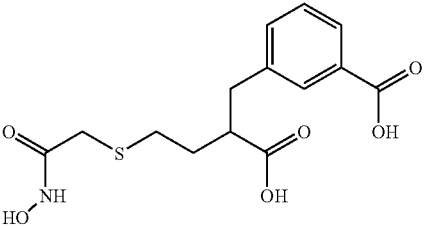 3-(2-Carboxy-4-hydroxycarbamoylmethyl-sulfanylbutyl)-benzoic acid | 4900 |
| 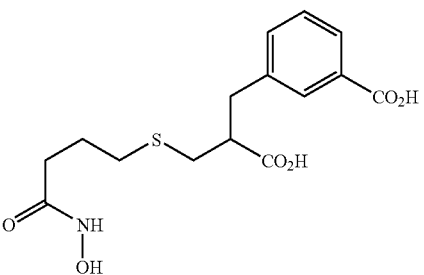 3-[2-Carboxy-3-(3-hydroxycarbamoyl-propylsulfanyl)-propyl]-benzoic acid | 6050 |
| 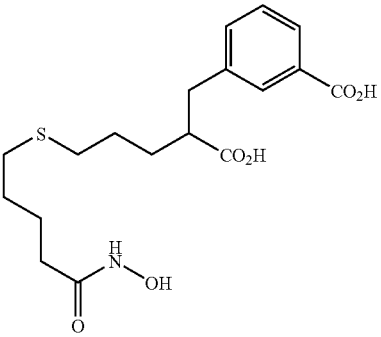 3-[2-Carboxy-5-(4-hydroxycarbamoyl-butylsulfanyl)-pentyl]-benzoic acid | 7580 |
| 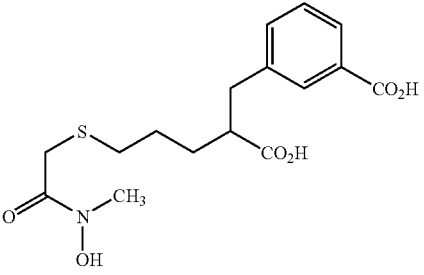 3-{2-Carboxy-5-[(hydroxy-methyl-carbamoyl)-methylsulfanyl]-pentyl}-benzoic acid | 14900 |
| 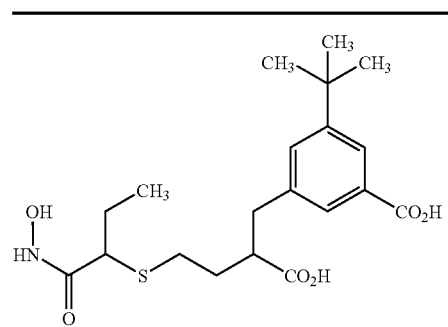 3-tert-Butyl-5-[2-carboxy-4-(1-hydroxycarbamoyl-propylsulfanyl)-butyl]-benzoic acid | 16000 |
| 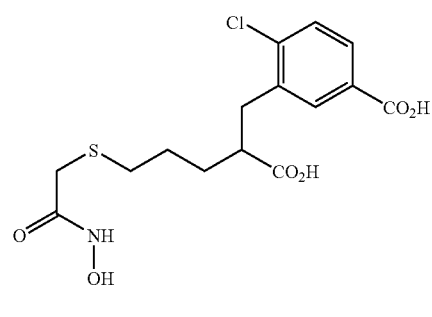 3-(2-Carboxy-5-hydroxycarbamoylmethyl-sulfanylpentyl)-4-chloro-benzoic acid | 16000 |
| 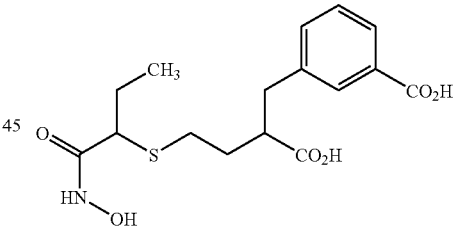 3-[2-Carboxy-4-(1-hydroxycarbamoyl-propylsulfanyl)-butyl]-benzoic acid | 19000 |
| 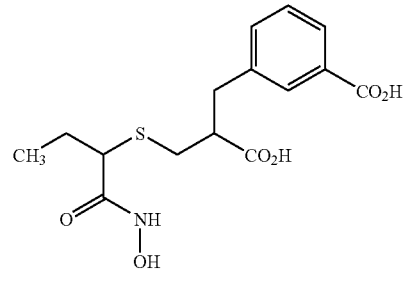 3-[2-Carboxy-3-(1-hydroxycarbamoyl-propylsulfanyl)-propyl]-benzoic acid | 41500 |

TABLE III-continued

IN VITRO INHIBITION OF NAALADASE ACTIVITY

| Compound | IC$_{50}$ |
|---|---|
| 4-(3-Hydroxycarbamoyl-propylsulfanylmethyl)-biphenyl-2,3'-dicarboxylic acid | 10820 |
| 3-(2-Hydroxycarbamoyl-methylsulfanyl-ethyl)-biphenyl-2,3'-dicarboxylic acid | 255 |
| | 1330 |
| 5-Hydroxycarbamoylmethoxy-isophthalic acid | 14800 |
| 3-Hydroxycarbamoylmethoxy-benzoic acid | 40800 |
| 3-(4-Hydroxycarbamoyl-butoxy)-biphenyl-2,3'-dicarboxylic acid | 55.9 |
| 3-(4-Hydroxycarbamoyl-butyoxy)-biphenyl-2,3'-dicarboxylic acid | 4800 |

TABLE III-continued

IN VITRO INHIBITION OF NAALADASE ACTIVITY

| Compound | IC$_{50}$ |
|---|---|
| 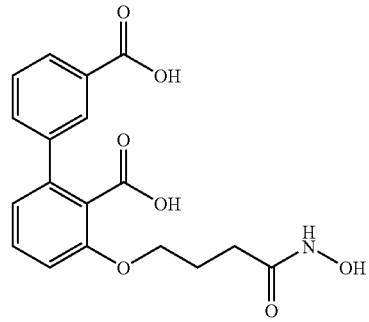 3-(3-Hydroxycarbamoyl-propoxy)-biphenyl-2,3'-dicarboxylic acid | 9100 |
| 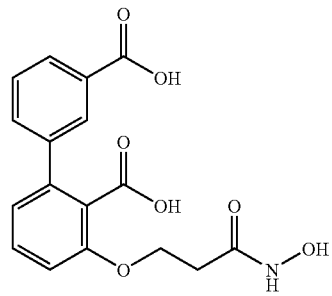 3-(2-Hydroxycarbamoyl-ethoxy)-biphenyl-2,3'-dicarboxylic acid | 14900 |
| 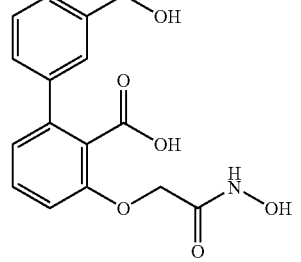 3-Hydroxycarbamoylmethoxy-biphenyl-2,3'-dicarboxylic acid | 27600 |
| 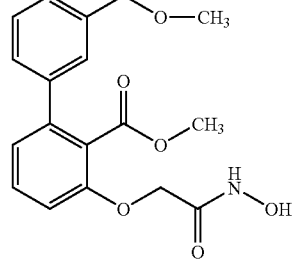 3-Hydroxycarbamoylmethoxy-biphenyl-2,3'-dicarboxylic acid dimethyl ester | 100000 |
| 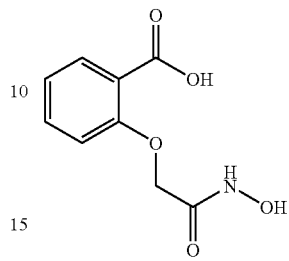 2-Hydroxycarbamoylmethoxy-benzoic acid | 100000 |
| 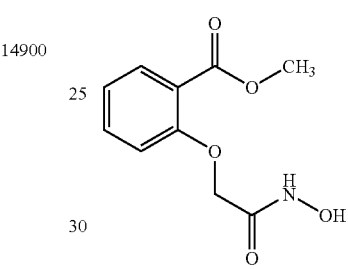 2-Hydroxycarbamoylmethoxy-benzoic acid methyl ester | 100000 |
| 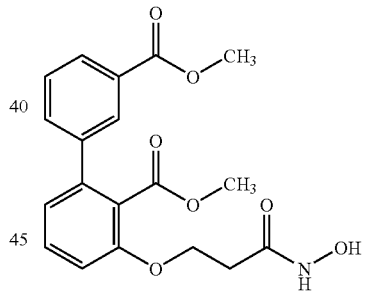 3-(2-Hydroxycarbamoyl-ethoxy)-biphenyl-2,3'-dicarboxylic acid dimethyl ester | 100000 |
| 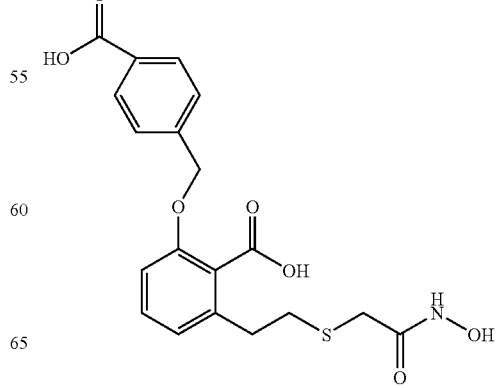 | 14000 |

TABLE III-continued
IN VITRO INHIBITION OF NAALADASE ACTIVITY

| Compound | IC$_{50}$ |
|---|---|
| 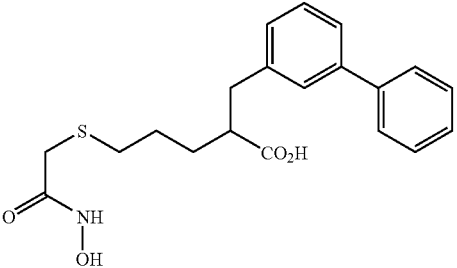 2-Biphenyl-3-ylmethyl-5-hydroxy-carbamoylmethylsulfanyl-pentanoic acid | 4210 |
| 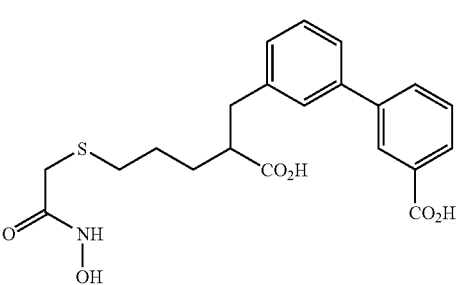 3'-(2-Carboxy-5-hydroxycarbamoylmethylsulfanyl-pentyl)-biphenyl-3-carboxylic acid | 23500 |
| 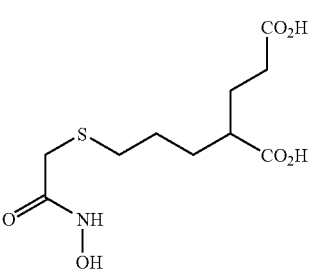 2-(3-Hydroxycarbamoyl-methylsulfanylpropyl)-pentanedioic acid | 3000 |
| 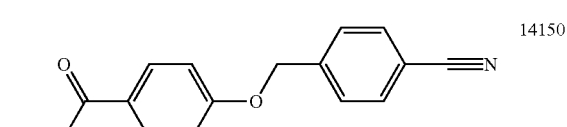 4-(4-Cyano-benzyloxy)-N-hydroxy-benzamide | 14150 |
| 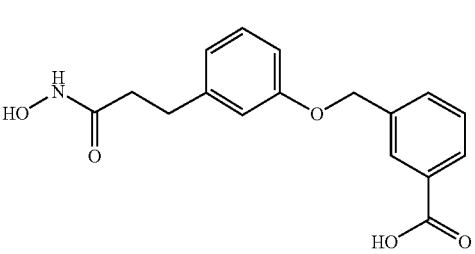 3-[3-(2-Hydroxycarbamoyl-ethyl)-phenoxymethyl]-benzoic acid | 92675 |

TABLE III-continued
IN VITRO INHIBITION OF NAALADASE ACTIVITY

| Compound | IC$_{50}$ |
|---|---|
| 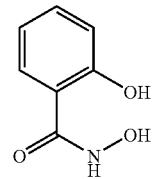 2,N-Dihydroxy-benzamide | 100000 |
| 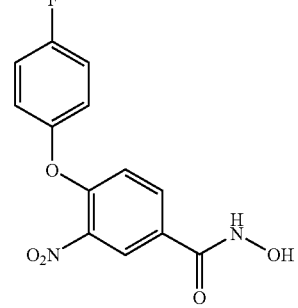 4-(4-Fluoro-phenoxy)-N-hydroxy-3-nitro-benzamide | 100000 |
| N-Hydroxy-2,5-bis-(2,2,2-trifluoro-ethoxy)-benzamide | |
| 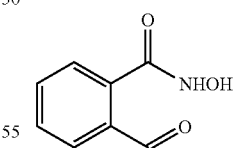 N-Hydroxy-2-(4-methyl-benzoyl)-benzamide | 100000 |
| 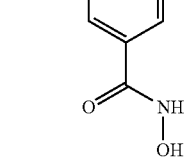 | 100000 |

Example 13

Protective Effect of NAALADase Inhibitors in Experimental Rat Glaucoma

Experimental Protocol

All experiments complied with the Association for Research in Vision and Ophthalmology Statement for the Use of Animals in Ophthalmic and Vision Research. 82 male Brown Norway rats (*Rattus norvegicus*), each weighing approximately 250 gm, were treated using procedures approved by the Animal Care Committee of the Johns Hopkins University School of Medicine. The rats were housed with a 12 hour light/12 hour dark cycle and fed ad libitum.

EXPERIMENTAL GLAUCOMA: Unilateral elevation of IOP was produced in 56 rats by microinjection of hypertonic saline into episcleral veins, following procedures described in Morrison, J. et al., *IOVS* (March 1998) 39:526-531. Beginning on the day of IOP elevation, the rats were treated daily with intraperitoneal injections of either a vehicle (23 rats with 50 mM HEPES-buffered saline) or a NAALADase inhibitor (11 rats with 10 mg/kg of 2-[[(2,3,4,5,6-pentafluorobenzyl)hydroxyphosphinyl]-methyl]pentanedioic acid ("Compound A") and 22 rats with 10 mg/kg of 2-(3-sulfanylpropyl)pentanedioic acid ("Compound B")). 11 saline treated rats, 11 Compound A treated rats and 11 Compound B treated rats were sacrificed at 8 weeks, and the remaining rats at 12 weeks, after initial IOP elevation.

OPTIC NERVE TRANSECTION: The optic nerve was transected unilaterally in 26 rats under intraperitoneal pentobarbital anesthesia. The conjunctiva was opened with scissors and the optic nerve exposed by traction on extraocular muscles. The transection was performed with microscissors 5 mm posterior to the globe, with specific attention to avoidance of injury to major ocular blood vessels. Immediately after transection, the retina was examined ophthalmoscopically to assure that the retinal arterial blood supply was not disrupted. The conjunctiva was closed with absorbable suture and the eye dressed with antibiotic ointment. Beginning on the day of transection, the rats were treated daily with intraperitoneal injections of either a vehicle (9 rats with 50 mM HEPES-buffered saline) or a NAALADase inhibitor (8 rats with 10 mg/kg of Compound A and 9 rats with 10 mg/kg of Compound B). 5 saline treated rats, 3 Compound A treated rats and 4 Compound B treated rats were sacrificed at 2 weeks, and the remaining rats at 4 weeks, after transection.

OPTIC NERVE COUNTING: The rats were sacrificed by exsanguination under deep pentobarbital anesthesia. They were perfused through the heart with 2% paraformaldehyde/2% glutaraldehyde in 0.1 M phosphate buffer, pH 7.2, and the eyes with attached optic nerves were removed. A cross-section of the optic nerve from both experimental (glaucoma or transection) and control eyes was removed 1.5 mm posterior to the globe, 1 mm in thickness, and post-fixed in 2% osmium tetroxide in buffer. These were processed into epoxy resin, sectioned at 1 micron and stained with toluidine blue.

The area of the optic nerve cross-section was measured by outlining its outer border at 10× magnification on an image analysis system (Universal Imaging Corp., Westchester, Pa.) with Synsys digital camera and Metamorph software. Three area measurements were taken and the mean value was determined. To measure the density and fiber diameter distributions, images were captured with a 100× phase contrast objective from 10 different areas of each nerve. These were edited to eliminate non-neural objects and the size of each axon internal to the myelin sheath (its minimum diameter) and the density of axons/square mm were calculated for each image and nerve. The mean density was multiplied by total nerve area to yield fiber number for each nerve. The total fiber number in glaucoma or transection nerves was compared to the normal, fellow eye of each rat to yield a percent loss value. The number of axons counted among the 10 images was an approximately 20% sample of the 80-90,000 axons in normal rat nerves. The person measuring axon number was masked to the protocol conducted on the nerves.

Results

EXPERIMENTAL GLAUCOMA: The mean fiber percent difference in the saline-treated, control rats was significantly lower in their glaucoma eyes compared to their normal eyes, with a mean±standard errors from the mean (SEM) fiber loss of 14.44±5.75% (n=11 rats; Table V) in the 8 week follow-up group, and 8.15±7.84% in the 12 week follow-up group (n=12 rats; Table VI).

By contrast, there was no significant loss of fibers in either the 8 week or 12 week NAALADase inhibitor-treated rats. The mean percent fiber loss in each NAALADase inhibitor-treated group was statistically less than the loss in the saline-treated, control groups (at 8 weeks, p=0.05 for Compound A and p=0.02 for Compound B).

TABLE V

EXPERIMENTAL GLAUCOMA RESULTS

| 8 WEEK GROUP | N | IOP INTEGRAL DIFFERENCE ± SEM | FIBER NUMBER ± SEM | PERCENT DIFFERENCE ± SEM |
|---|---|---|---|---|
| Compound A | 11 | 85 ± 37.5 | 79156 ± 2436* | −1.82 ± 2.92 |
| Compound B | 11 | 116 ± 33.2 | 80785 ± 2121** | −0.82 ± 2.97 |
| Control | 11 | 104 ± 26.4 | 68295 ± 4617 | 14.44 ± 5.75 |

TABLE VI

EXPERIMENTAL GLAUCOMA RESULTS

| 12 WEEK GROUP | N | IOP INTEGRAL DIFFERENCE | FIBER NUMBER | PERCENT DIFFERENCE |
|---|---|---|---|---|
| Compound B | 11 | 109 ± 45.2 | 90504 ± 1718 | −3.21 ± 2.86 |
| Control | 12 | 158 ± 66.5 | 79827 ± 6783 | 8.15 ± 7.84 |

IOP Integral Difference=difference in intraocular pressure (IOP) exposure between glaucoma eye and normal eye in each rat (mm Hg—days).

Percent Difference=mean percent difference in fiber number between glaucoma and normal eye in each rat (positive value indicates fewer fibers in the glaucoma eye).

Differences in IOP Integral Difference are not significant (p>0.05).

Differences in Percent Difference between drug-treated and saline-treated, control rats at 8 weeks post insult are significant (p=0.05* and p=0.02**).

OPTIC NERVE TRANSECTION: The experimental transection data suggest a slowing or rescue of ultimate RGC death in rats treated with NAALADase inhibitors at 2 weeks after transection. At 2 weeks after transection, both drug-treated groups had more remaining RGC axons than did the saline-treated, control group, judged either by absolute number of fibers or percent difference between transected eye and normal eye in each rat (TABLE VII). Rats treated with Compound A and Compound B had, respectively, 3 times and twice as many remaining axons as the saline-treated rats. All or nearly all RGC die within the first 2 months after transection, regardless of any pharmacological treatment. Thus, by 4 weeks after transection, more than 80% of RGC axons were gone in all groups (TABLE VIII). At 4 weeks after transection, there were no significant differences between the drug-treated rats and the saline-treated rats.

TABLE VII

OPTIC NERVE TRANSECTION

| 2 WEEKS SURVIVAL | N | FIBER NUMBER ± SEM | PERCENT DIFFERENCE ± SEM |
|---|---|---|---|
| Compound A | 3 | 26,426 ± 13,293 | 65.3 ± 17.8 |
| Compound B | 4 | 19,550 ± 5,091 | 75.3 ± 6.6 |
| Control | 5 | 8,220 ± 4,668 | 90.2 ± 5.35 |

TABLE VIII

OPTIC NERVE TRANSECTION

| 4 WEEKS SURVIVAL | N | FIBER NUMBER ± SEM | PERCENT DIFFERENCE ± SEM |
|---|---|---|---|
| Compound A | 5 | 13,599 ± 3,519 | 82.4 ± 4.0 |
| Compound B | 5 | 5,162 ± 2,509 | 93.4 ± 3.1 |
| Control | 4 | 10,449 ± 3,648 | 86.9 ± 4.7 |

Percent Difference=mean percent difference in fiber number between glaucoma and normal eye in each rat (positive value indicates fewer fibers in the glaucoma eye).

Differences in Percent Difference between drug-treated and saline-treated, control rats are not statistically significant ($p=0.05$).

Example 14

Efficacy of NAALADase Inhibitors in Treating Retinal Disorders

Four (4) groups of rats received daily insulin injections to maintain their glucose levels at about 350 mg/dl. Starting at the onset of hyperglycemia, NAALADase inhibitor 2-(3-sulfanylpropyl)-pentanedioic acid was administered daily for 6 months to one group of BB/W rats at a dose of 10 mg/kg and to a second group of BB/W rats at a dose of 30 mg/kg. A third group of BB/W rats and a fourth group of non-diabetic rats received daily vehicle treatment (50 mM Hepes buffered saline).

After six (6) months of NAALADase inhibitor or vehicle treatment, the rats were sacrificed and their eyes were removed. From each rat, one eye was processed for elastase digest while the other eye was processed for transmission electron microscopy (TEM) and basement membrane (BM) thickness.

Elastase Digests

Retinal digests were prepared using elastase on retinas as described in Layer, N., *Invest Ophthalmol Vis Sci* (1993) 34:2097. Eyes were removed from recently killed BB/W rats (n=25) and age-matched transgenic controls (n=10). The retinas (n=35) were fixed at room temperature by immersing the whole eye (slit at limbus) in 4% (w/v) paraformaldehyde in 50 mmol/L Na-K phosphate buffer with 8% sucrose. The fixed retinas were rinsed in deionized water and were incubated for 3 minutes in a 37° C. agitating water bath in 40 units/mL elastase in Na-K phosphate buffer with 150 mmol/L NaCl and 5 mmol/L ethylenediamine tetraacetic acid (EDTA), pH 6.5. The tissues were washed overnight in 100 mmol/L Tris-HCL (pH 8.5) and then transferred to deionized water for removal of the loosened vitreous and digested neural elements by gentle agitation using the sides of closed forceps and the sides and ends of very fine brushes. After all loose tissues were removed, the retinas were incubated once more in fresh enzyme for 3 minutes and then subjected to a second overnight wash at room temperature in Tns-HCl buffer. On the third day, the retinas were again transferred to deionized water for additional removal of digested neural elements. The vascular network that was completely free of nonvascular elements was mounted flat by flotation in $Ca^{2+}$ and $Mg^{2+}$ free Dulbecco's PBS on siliconized slides (#S1308, Oncor, Gaithersburg, Md.). After air drying in a dust free environment, the mounts of the retinal microvasculature were stained using periodic acid Schiff reaction and hematoxylin counterstaining, as described in Luna, L., ed. *Manual of Histologic Staining Methods of the Armed Forces Institute of Pathology* (1968) McGraw-Hill, New York, N.Y. The preparations were then examined by light microscopy and photographed.

Endothelial/Pericyte (E/P) Ratios

The stained and intact retinal whole mounts were coded and subsequent counting was done masked, as described in Cuthbertson, R., *Invest Ophthalmol Vis Sci*. (1986) 27:1659-1664).

Ten fields at ×100 magnification were counted for endothelial and pericyte cells using previously described morphologic criteria (see Kuwabara, T., *Arch Ophthalmol*. (1960) 64:904-911). In every sample, at least 200 cells were counted from the mid zone of the retina. Mean values for endothelial cell/pericyte (E/P) ratios were initially calculated in 3 retinas from each of the four (4) groups of rats.

Evaluation of BM Thickness

Each eye was fixed in 4% glutaraldehyde and dissected free of sclera and choroids, then trimmed and postfixed in 1% osmium tetroxide. After dehydration and embedding, thin sections were stained with uranyl acetate and lead citrate. Initially, EM thickness of retinal capillaries from 3 non-diabetic rats receiving vehicle, 3 diabetic animals receiving 10 mg/kg 2-(3-sulfanylpropyl)-pentanedioic acid, and 3 diabetic rats receiving 30 mg/kg 2-(3-sulfanylpropyl)-pentanedioic acid were compared with 3 diabetic rats receiving a vehicle. At least 10 capillaries per eye from the inner nuclear and plexiform layers were photographed at a magnification of 10,000×. Exact magnification was determined for each set of negatives with a 28,800 line/inch calibration grid. Negatives were enlarged 3×. Measurements, to the nearest 0.25 mm, were made of the basement membrane surrounding the endothelial cell and were taken perpendicular to the plane of the basement membrane, as described in Bendayan, M., *J. Electron Microsc Techn* (1984) 1:243-270; and Gunderson, *J. Microscopy* (1980) 121:65-73). At least 20 measurements were taken for each capillary and the BM thickness was expressed as an average of 20 measurements.

Statistical Analysis

Statistical analysis for comparison among groups was performed using one way analysis of variance (ANOVA)

and Student's t test. Significance was defined as a value of p<0.05. Values were reported as mean±standard errors from the mean (SEM), unless otherwise noted.

Results of Elastase Digest Preparations and E/P Ratios

Figure 2:
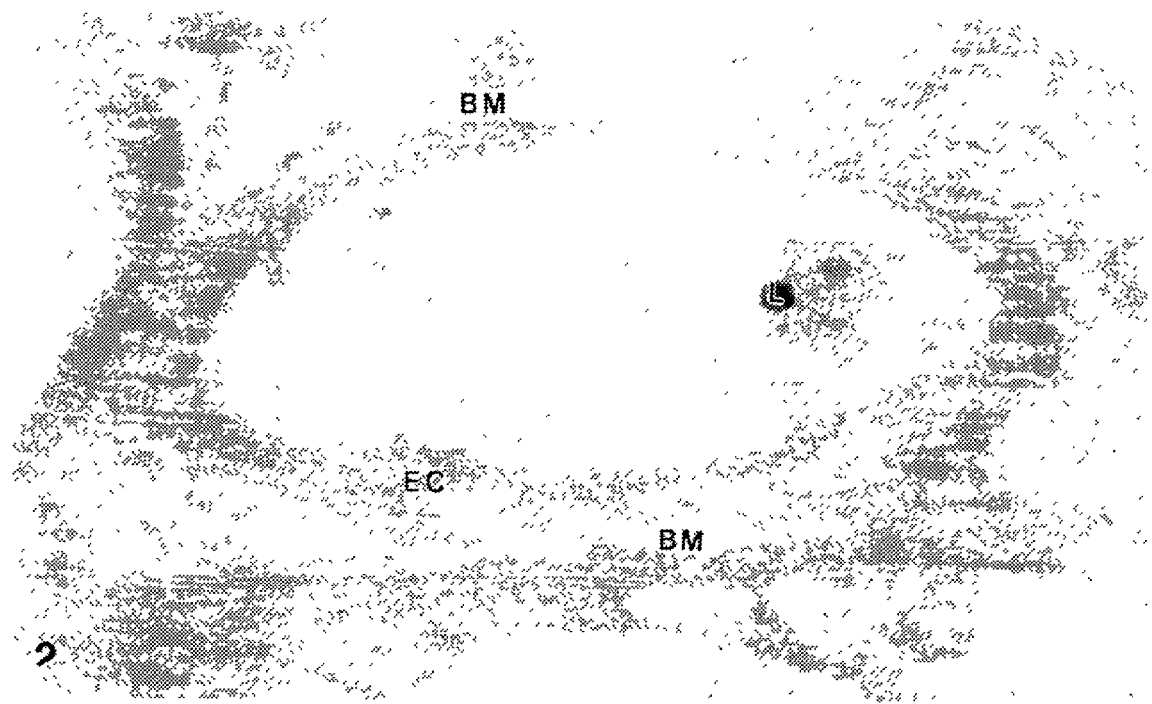
FIG. 2 is a 27,000× magnified photograph of a retinal blood vessel from a diabetic rat after six months of treatment with a vehicle.
Figure 3:
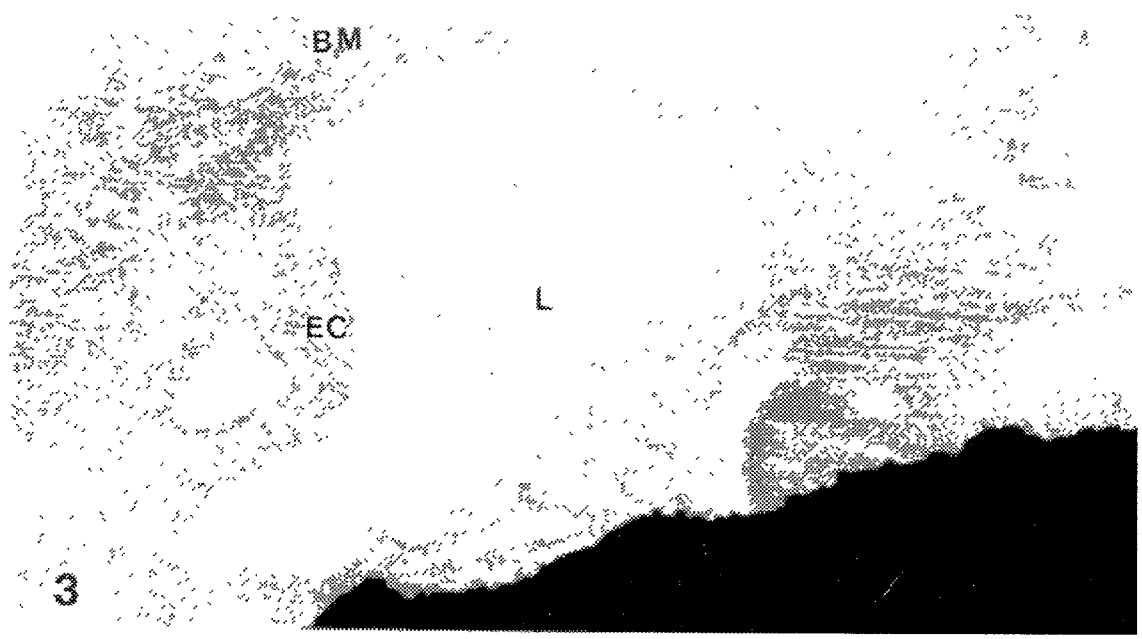
FIG. 3 is a 27,000× magnified photograph of a retinal blood vessel from a diabetic rat after six months of treatment with NAALADase inhibitor 2-(3-sulfanylpropyl)pentanedioic acid.

In intact whole mounts of retinal digests the endothelial cell nuclei, seen medially within the vessel wall, were large, oval, pale staining and protruded lumenally. Pericyte nuclei, seen more laterally, were dark staining, small, round and protruded prominently away from the vessel wall. F/P counts were taken from mid zones of the retinas. The attached figures show 27,000× magnified photographs of retinal blood vessels from a control, non-diabetic rat (FIG. 1), from a control, diabetic rat after six (6) months of treatment with a vehicle (FIG. 2), and from a diabetic rat after six (6) months of treatment with NAALADase inhibitor 2-(3-sulfanylpropyl)-pentanedioic acid (FIG. 3). In the figures, "BM" refers to basement membrane, "EC" refers to endothelial cell, and "L" refers to vessel lumen.

NAALADase inhibition had no effect on blood glucose or body weight. Six month high dose (30 mg/kg) treatment with 2-(3-sulfanylpropyl)-pentanedioic acid resulted in a 29.0% reduction in BM thickness (diabetic vehicle=101.0±14.81 nm and diabetic NAALADase$_{30}$=71.7±4.07 nm), while treatment with the low dose resulted in an 18.5% decrease in BM thickness (NAALADase$_{10}$=82.3±4.07 nm). This was accompanied by a 37% reduction of E/P ratios in rats treated with the high dose 2-(3-sulfanylpropyl)-pentanedioic acid (diabetic vehicle=3.0±0.3 and NAALADase$_{30}$=1.9±0.4), while treatment with low dose resulted in a 20% reduction of the same cell ratios (NAALADase$_{10}$=2.4±0.5). See TABLE III.

TABLE III

| RAT GROUP | BM THICKNESS (nm) ± SD (n = 3) | E/P RATIO (n = 8–10) |
|---|---|---|
| NON-DIABETIC CONTROLS | 56.3 ± 4.78 | 1.7 ± 0.07 |
| DIABETIC VEHICLE | 101 ± 14.81 | 3.0 ± 0.3 |
| DIABETIC 30 MG/KG NAAALADASE INHIBITOR | 71.7 ± 4.07 | 1.9 ± 0.4 |
| DIABETIC 10 MG/KG NAALADASE INHIBITOR | 82.3 ± 4.07 | 2.4 ± 0.5 |

Conclusions

The BB/W rats demonstrated an early change typically associated with diabetic retinopathy (pericyte loss and basement membrane thickening) but did not show significant numbers of microanuerysms also typical of diabetic retinopathy or areas of acellular capillaries usually seen in more advanced disease. The retinopathy observed in BB/W has been previously characterized in Chakrabarti, *Diabetes* (1989) 38:1181-1186.

The results show that treatment with a NAALADase inhibitor causes improvement in retinal pathology of diabetic rats. Specifically, the NAALADase inhibitor prevented pericyte loss and basement membrane thickening in retinal vessels.

All publications, patents and patent applications identified above are herein incorporated by reference, as though set forth herein in full.

The invention being thus described, it will be apparent to those skilled in the art that the same may be varied in many ways without departing from the spirit and scope of the invention. Such variations are included within the scope of the following claims.

What is claimed is:

1. A method for treating retinopathy, age-related macular degeneration or glaucoma comprising administering to a mammal in need of such treatment an effective amount of a compound of formula X

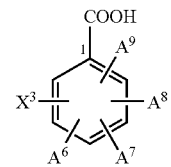

or an enantiomer or a pharmaceutically acceptable equivalent of said compound, wherein:
X$^3$ is —(CR$^{36}$R$^{37}$)$_n$SH, —O(CR$^{36}$R$^{37}$)$_2$SH, —S(CR$^{36}$R$^{37}$)$_2$SH or —NR(CR$^{36}$R$^{37}$)$_2$SH;
n is 1-3; and
R, R$^{36}$, R$^{37}$, A$^6$, A$^7$, A$^8$ and A$^9$ are independently hydrogen, C$_1$-C$_9$ alkyl, C$_2$-C$_9$ alkenyl, C$_2$-C$_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, C$_1$-C$_9$ alkylsulfonyl, C$_1$-C$_9$ alkoxy, C$_2$-C$_9$ alkenoxy, phenoxy and benzyloxy, wherein said alkyl, alkenyl, alkynyl, aryl, heteroaryl, carbocycle, heterocycle, alkoxy, alkenoxy, phenoxy and benzyloxy are independently unsubstituted or substituted with one or more substituent(s).

2. The method of claim 1, wherein the compound of formula X is selected from the group consisting of:
3-(2-mercaptoethyl)-benzoic acid;
3-(mercaptomethyl)-benzoic acid;
2-(mercaptomethyl)-benzoic acid;
5-hydroxy-2-(2-mercaptoethyl)-benzoic acid;
2-(2-mercaptoethyl)-benzoic acid;
5-[(4-carboxyphenyl)methoxy]-2-(2-mercaptoethyl)-benzoic acid;
2-(2-mercaptoethyl)-5-(phenylmethoxy)-benzoic acid;
2-(carboxymethoxy)-6-(2-mercaptoethyl)-benzoic acid;
5-[(3-carboxyphenyl)methoxy]-2-(2-mercaptoethyl)-benzoic acid;
2-(2-mercaptoethyl)-6-(phenylmethoxy)-benzoic acid;
2-[(2-carboxyphenyl)methoxy]-6-(2-mercaptoethyl)-benzoic acid;
2-[(4-carboxyphenyl)methoxy]-6-(2-mercaptoethyl)-benzoic acid;
3-(2-mercaptoethyl)-[1,1'-biphenyl]-2,3'-dicarboxylic acid;
2-(3,3-dimethylbutoxy)-6-(2-mercaptoethyl)-benzoic acid;
2-(2-mercaptoethyl)-6-(2-phenylethoxy)-benzoic acid;
2-[(2-chlorophenyl)methoxy]-6-(2-mercaptoethyl)-benzoic acid;
2-[[3-carboxy-5-(1,1-dimethylethyl)phenyl]methoxy]-6-(2-mercaptoethyl)-benzoic acid;
2-(2-mercaptoethyl)-6-phenoxy-benzoic acid;
2-(2-mercaptoethyl)-6-phenylamino-benzoic acid;
2-(2-mercaptoethyl)-6-(phenylthio)-benzoic acid;
5'-(1,1-dimethylethyl)-3-(2-mercaptoethyl)-[1,1'-biphenyl]-2,3'-dicarboxylic acid;
3-(2-mercaptoethyl)-[1,1'-biphenyl]-2,4'-dicarboxylic acid;
2-[(4-carboxy-2-methoxyphenyl)methoxy]-6-(2-mercaptoethyl)-benzoic acid;

2-[(4-carboxy-3-methoxyphenyl)methoxy]-6-(2-mercaptoethyl)-benzoic acid;
2-[(2-bromo-4-carboxyphenyl)methoxy]-6-(2-mercaptoethyl)-benzoic acid;
2-[(3-bromo-4-carboxyphenyl)methoxy]-6-(2-mercaptoethyl)-benzoic acid;
2-[(4-chlorophenyl)methoxy]-6-(2-mercaptoethyl)-benzoic acid;
2-(biphenyl-2-ylmethoxy)-6-(2-mercaptoethyl)-benzoic acid;
2-[(3-bromo-5-carboxyphenyl)methoxy]-6-(2-mercaptoethyl)-benzoic acid;
2-[(2-bromo-5-carboxyphenyl)methoxy]-6-(2-mercaptoethyl)-benzoic acid;
2-(2-mercaptoethyl)-6-[(4-methoxyphenyl)methoxy]-benzoic acid;
2-(2-mercaptoethyl)-6-[(4-methylphenyl)methoxy]-benzoic acid;
2-[(4-bromo-3-carboxyphenyl)methoxy]-6-(2-mercaptoethyl)-benzoic acid;
2-[(2-carboxy-5-methoxyphenyl)methoxy]-6-(2-mercaptoethyl)-benzoic acid;
5-(mercaptomethyl)-2-(2-phenylethoxy)-benzoic acid;
2-bromo-5-(mercaptomethyl)-benzoic acid;
4-(mercaptomethyl)-[1,1'-biphenyl]-2,3'-dicarboxylic acid;
5-(mercaptomethyl)-2-(phenylmethoxy)-benzoic acid; and
4-bromo-3-(mercaptomethyl)-benzoic acid; and
enantiomers and pharmaceutically acceptable equivalents.

3. The method of claim 1, wherein the method is for treating retinopathy.

4. The method of claim 3, wherein the retinopathy is diabetic retinopathy.

5. The method of claim 1, wherein the method is for treating age-related macular degeneration.

6. The method of claim 1, wherein the method is for treating glaucoma.

7. The method of claim 2, wherein the method is for treating retinopathy.

8. The method of claim 7, wherein the retinopathy is diabetic retinopathy.

9. The method of claim 2, wherein the method is for treating age-related macular degeneration.

10. The method of claim 2, wherein the method is for treating glaucoma.

* * * * *